US009000189B2

(12) United States Patent
Bretschneider et al.

(10) Patent No.: US 9,000,189 B2
(45) Date of Patent: Apr. 7, 2015

(54) BIPHENYL-SUBSTITUTED SPIROCYCLIC KETOENOLS

(75) Inventors: Thomas Bretschneider, Lohmar (DE); Reiner Fischer, Monheim (DE); Rolf Pontzen, Leichlingen (DE); Christian Arnold, Langenfeld (DE); Ulrich Görgens, Ratingen (DE); Olga Malsam, Rösrath (DE); Udo Reckmann, Köln (DE); Erich Sanwald, Holländer (DE); Stefan Lehr, Liederbach (DE); Jan Dittgen, Frankfurt (DE); Dieter Feucht, Eschborn (DE); Martin Hills, Idstein (DE); Christopher Rosinger, Hofheim (DE)

(73) Assignee: Bayer CropScience AG, Monheim (DE)

( * ) Notice: Subject to any disclaimer, the term of this patent is extended or adjusted under 35 U.S.C. 154(b) by 497 days.

(21) Appl. No.: 12/517,419

(22) PCT Filed: Nov. 22, 2007

(86) PCT No.: PCT/EP2007/010103

§ 371 (c)(1),
(2), (4) Date: Dec. 15, 2009

(87) PCT Pub. No.: WO2008/067911

PCT Pub. Date: Jun. 12, 2008

(65) Prior Publication Data

US 2011/0306499 A1 Dec. 15, 2011

(30) Foreign Application Priority Data

Dec. 4, 2006 (DE) ......................... 10 2006 057 036

(51) Int. Cl.

| | |
|---|---|
| ***C07D 487/10*** | (2006.01) |
| ***A01N 43/90*** | (2006.01) |
| ***C07D 209/54*** | (2006.01) |
| ***A01N 43/12*** | (2006.01) |
| ***A01N 43/38*** | (2006.01) |
| ***C07C 69/65*** | (2006.01) |
| ***C07C 69/757*** | (2006.01) |
| ***C07C 233/52*** | (2006.01) |
| ***C07C 255/46*** | (2006.01) |
| ***C07D 307/94*** | (2006.01) |
| ***C07D 309/28*** | (2006.01) |
| ***C07D 317/72*** | (2006.01) |
| ***C07D 319/08*** | (2006.01) |
| ***C07D 491/107*** | (2006.01) |
| ***C07D 491/113*** | (2006.01) |

(Continued)

(52) U.S. Cl.

CPC ............ *C07D 209/54* (2013.01); *C07D 487/10* (2013.01); *A01N 43/12* (2013.01); *A01N 43/38* (2013.01); *A01N 43/90* (2013.01); *C07C 69/65* (2013.01); *C07C 69/757* (2013.01); *C07C 233/52* (2013.01); *C07C 255/46* (2013.01); *C07C 2101/08* (2013.01); *C07C 2101/14* (2013.01); *C07D 307/94* (2013.01); *C07D 309/28* (2013.01); *C07D 317/72* (2013.01); *C07D 319/08* (2013.01); *C07D 491/107* (2013.01); *C07D 491/113* (2013.01); *C07D 493/10* (2013.01); *C07D 495/10* (2013.01)

(58) Field of Classification Search

CPC .............................. C07D 487/10; A01N 43/90
USPC .......................................... 548/410; 514/409
See application file for complete search history.

(56) References Cited

U.S. PATENT DOCUMENTS

| | | | |
|---|---|---|---|
| 2,842,476 | A | 7/1958 | Schreiber |
| 3,928,330 | A | 12/1975 | Ramey et al. |
| 4,021,224 | A | 5/1977 | Pallos et al. |

(Continued)

FOREIGN PATENT DOCUMENTS

| | | | |
|---|---|---|---|
| CA | 1 162 071 | A1 | 2/1984 |
| CA | 2 627 240 | A1 | 5/2007 |

(Continued)

OTHER PUBLICATIONS

Fischer et al. (CAPLUS Abstract of WO 2003059065).*

(Continued)

*Primary Examiner* — Robert Havlin
(74) *Attorney, Agent, or Firm* — Sterne, Kessler, Goldstein & Fox P.L.L.C.

(57) ABSTRACT

The invention relates to novel compounds of the formula (I)

(I)

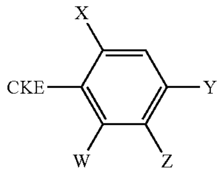

in which

W, X, Y, Z and CKE have the meanings given above, to a plurality of processes and intermediates for their preparation and to their use as pesticides and/or herbicides, and also to selective herbicidal compositions comprising, firstly, the compounds of the formula (I) and, secondly, at least one crop plant compatibility-improving compound.

The invention further relates to the boosting of the action of crop protection compositions comprising compounds of the formula (I) through the additions of ammonium salts or phosphonium salts and optionally penetrants.

7 Claims, No Drawings

(51) Int. Cl.
*C07D 493/10* (2006.01)
*C07D 495/10* (2006.01)

(56) References Cited

U.S. PATENT DOCUMENTS

| | | | |
|---|---|---|---|
| 4,097,587 | A | 6/1978 | Soma et al. |
| 4,186,130 | A | 1/1980 | Teach |
| 4,623,727 | A | 11/1986 | Hubele |
| 4,639,266 | A | 1/1987 | Heubach et al. |
| 4,844,734 | A | 7/1989 | Iwasaki et al. |
| 4,881,966 | A | 11/1989 | Nyffeler et al. |
| 4,888,049 | A | 12/1989 | Iwasaki et al. |
| 4,891,057 | A | 1/1990 | Sohn et al. |
| 4,902,340 | A | 2/1990 | Hubele |
| 4,925,868 | A | 5/1990 | Terao et al. |
| 4,985,063 | A | 1/1991 | Fischer et al. |
| 5,045,560 | A | 9/1991 | Fischer et al. |
| 5,094,681 | A | 3/1992 | Kramer et al. |
| 5,116,836 | A | 5/1992 | Fischer et al. |
| 5,164,179 | A | 11/1992 | Hioki et al. |
| 5,225,434 | A | 7/1993 | Bertram et al. |
| 5,258,527 | A | 11/1993 | Krauskopf et al. |
| 5,262,383 | A | 11/1993 | Fischer at al. |
| 5,314,863 | A | 5/1994 | Loher et al. |
| 5,380,852 | A | 1/1995 | Schutze et al. |
| 5,401,700 | A | 3/1995 | Sohn et al. |
| 5,407,897 | A | 4/1995 | Cary et al. |
| 5,462,912 | A | 10/1995 | Hioki et al. |
| 5,462,913 | A | 10/1995 | Fischer et al. |
| 5,504,057 | A | 4/1996 | Fischer et al. |
| 5,508,436 | A | 4/1996 | Fischer et al. |
| 5,516,750 | A | 5/1996 | Willms et al. |
| 5,538,937 | A | 7/1996 | Hasebe et al. |
| 5,567,671 | A | 10/1996 | Fischer et al. |
| 5,589,469 | A | 12/1996 | Fischer et al. |
| 5,610,122 | A | 3/1997 | Fischer et al. |
| 5,622,917 | A | 4/1997 | Fischer et al. |
| 5,683,965 | A | 11/1997 | Bachmann et al. |
| 5,700,758 | A | 12/1997 | Rosch et al. |
| 5,705,476 | A | 1/1998 | Hoffarth |
| 5,739,079 | A | 4/1998 | Holdgrun et al. |
| 5,792,755 | A | 8/1998 | Sagenmuller et al. |
| 5,811,374 | A | 9/1998 | Bertram et al. |
| 5,830,825 | A | 11/1998 | Fischer et al. |
| 5,830,826 | A | 11/1998 | Fischer et al. |
| 5,945,444 | A | 8/1999 | Fischer et al. |
| 6,114,374 | A | 9/2000 | Lieb et al. |
| 6,133,296 | A | 10/2000 | Lieb et al. |
| 6,140,358 | A | 10/2000 | Lieb et al. |
| 6,200,932 | B1 | 3/2001 | Fischer et al. |
| 6,235,680 | B1 | 5/2001 | Ziemer et al. |
| 6,251,827 | B1 | 6/2001 | Ziemer et al. |
| 6,251,830 | B1 | 6/2001 | Fischer et al. |
| 6,288,102 | B1 | 9/2001 | Hagemann et al. |
| 6,316,486 | B1 | 11/2001 | Lieb et al. |
| 6,358,887 | B1 | 3/2002 | Fischer et al. |
| 6,417,370 | B1 | 7/2002 | Lieb et al. |
| 6,451,843 | B1 | 9/2002 | Lieb et al. |
| 6,458,965 | B1 | 10/2002 | Lieb et al. |
| 6,472,419 | B1 | 10/2002 | Fischer et al. |
| 6,511,940 | B1 | 1/2003 | Ziemer et al. |
| 6,511,942 | B1 | 1/2003 | Lieb et al. |
| 6,589,976 | B1 | 7/2003 | Fischer et al. |
| 6,602,823 | B1 | 8/2003 | Rochling et al. |
| 6,608,211 | B1 | 8/2003 | Hagemann et al. |
| 6,645,914 | B1 | 11/2003 | Woznica et al. |
| 6,861,391 | B1 | 3/2005 | Fischer et al. |
| 6,894,005 | B1 | 5/2005 | Maetzke et al. |
| 7,569,517 | B2 | 8/2009 | Fischer et al. |
| 2003/0216260 | A1 | 11/2003 | Ruther et al. |
| 2003/0224939 | A1 | 12/2003 | Miles |
| 2005/0009880 | A1 | 1/2005 | Cottrell et al. |
| 2005/0054535 | A1 | 3/2005 | Fischer et al. |
| 2005/0096386 | A1 | 5/2005 | Cottrell et al. |
| 2006/0160847 | A1 | 7/2006 | Fischer et al. |
| 2006/0166829 | A1 | 7/2006 | Fischer et al. |
| 2007/0015664 | A1 | 1/2007 | Fischer et al. |
| 2007/0032539 | A1 | 2/2007 | Himmler |
| 2007/0129252 | A1 | 6/2007 | Fischer et al. |
| 2007/0225167 | A1 | 9/2007 | Fischer et al. |
| 2007/0225170 | A1 | 9/2007 | Fischer et al. |
| 2007/0244007 | A1 | 10/2007 | Fischer et al. |
| 2007/0275858 | A1 | 11/2007 | Fischer et al. |
| 2007/0298968 | A1 | 12/2007 | Bretschneider et al. |
| 2007/0298969 | A1 | 12/2007 | Fischer et al. |
| 2008/0026943 | A1 | 1/2008 | Fischer et al. |
| 2008/0188371 | A1 | 8/2008 | Fischer et al. |
| 2008/0220973 | A1 | 9/2008 | Fischer et al. |
| 2008/0305955 | A1 | 12/2008 | Bretschneider et al. |
| 2008/0318776 | A1 | 12/2008 | Fischer et al. |
| 2009/0029858 | A1 | 1/2009 | Fischer et al. |
| 2009/0298828 | A1 | 12/2009 | Fischer et al. |
| 2011/0130284 | A1 | 6/2011 | Fischer et al. |

FOREIGN PATENT DOCUMENTS

| | | | |
|---|---|---|---|
| CA | 2 632 892 | A1 | 6/2007 |
| CA | 2 633 448 | A1 | 6/2007 |
| CA | 2 633 525 | A1 | 7/2007 |
| CA | 2 642 787 | A1 | 8/2007 |
| CA | 2 649 552 | A1 | 11/2007 |
| DE | 22 18 097 | A1 | 11/1972 |
| DE | 23 50 547 | A1 | 4/1974 |
| DE | 26 23 464 | A1 | 12/1976 |
| DE | 40 14 420 | A1 | 4/1991 |
| DE | 19 62 1522 | A1 | 12/1997 |
| DE | 10 2005 059 892 | A1 | 6/2007 |
| DE | 10 2006 007 882 | A1 | 8/2007 |
| DE | 10 2006 018 828 | A1 | 10/2007 |
| DE | 10 2006 025 874 | A1 | 12/2007 |
| DE | 10 2006 050 148 | A1 | 4/2008 |
| EP | 0 036 106 | A2 | 9/1981 |
| EP | 0 086 750 | A2 | 8/1983 |
| EP | 0 094 349 | A2 | 11/1983 |
| EP | 0 174 562 | A2 | 3/1986 |
| EP | 0 191 736 | A2 | 8/1986 |
| EP | 0 262 399 | A2 | 4/1988 |
| EP | 0 269 806 | A1 | 6/1988 |
| EP | 0 333 131 | A1 | 9/1989 |
| EP | 0 346 620 | A1 | 12/1989 |
| EP | 0 355 599 | A1 | 2/1990 |
| EP | 0 377 893 | A2 | 7/1990 |
| EP | 0 415 211 | A2 | 3/1991 |
| EP | 0 442 073 | A2 | 8/1991 |
| EP | 0 442 077 | A2 | 8/1991 |
| EP | 0 453 086 | A2 | 10/1991 |
| EP | 0 456 063 | A2 | 11/1991 |
| EP | 0 492 366 | A2 | 7/1992 |
| EP | 0 52 1334 | A1 | 1/1993 |
| EP | 0 528 156 | A1 | 2/1993 |
| EP | 0 582 198 | A2 | 2/1994 |
| EP | 0 595 130 | A1 | 5/1994 |
| EP | 0 596 298 | A2 | 5/1994 |
| EP | 0 613 618 | A1 | 9/1994 |
| EP | 0 613 884 | A2 | 9/1994 |
| EP | 0 613 885 | A2 | 9/1994 |
| EP | 0 647 637 | A1 | 4/1995 |
| EP | 0 664 081 | A2 | 7/1995 |
| EP | 0 668 267 | A1 | 8/1995 |
| EP | 0 681 865 | A2 | 11/1995 |
| FR | 2 600 494 | A1 | 12/1987 |
| GB | 22 66 888 | A | 11/1993 |
| JP | 2000 053670 | A | 2/2000 |
| WO | WO 91/07874 | A1 | 6/1991 |
| WO | WO 91/08202 | A1 | 6/1991 |
| WO | WO 92/16108 | A1 | 10/1992 |
| WO | WO 95/01971 | A1 | 1/1995 |
| WO | WO 95/07897 | A1 | 3/1995 |
| WO | WO 95/17817 | A1 | 7/1995 |
| WO | WO 95/20572 | A1 | 8/1995 |
| WO | WO 95/26345 | A1 | 10/1995 |
| WO | WO 95/26954 | A1 | 10/1995 |
| WO | WO 96/20196 | A1 | 7/1996 |
| WO | WO 96/25395 | A1 | 8/1996 |

(56) References Cited

FOREIGN PATENT DOCUMENTS

| | | | |
|---|---|---|---|
| WO | WO 96/35664 | A1 | 11/1996 |
| WO | WO 97/01535 | A1 | 1/1997 |
| WO | WO 97/02243 | A1 | 1/1997 |
| WO | WO 97/36868 | A1 | 10/1997 |
| WO | WO 97/43275 | A2 | 11/1997 |
| WO | WO 98/05638 | A2 | 2/1998 |
| WO | WO 98/06721 | A1 | 2/1998 |
| WO | WO 98/25928 | A1 | 6/1998 |
| WO | WO 98/35553 | A1 | 8/1998 |
| WO | WO 99/16748 | A1 | 4/1999 |
| WO | WO 99/24437 | A1 | 5/1999 |
| WO | WO 99/43649 | A1 | 9/1999 |
| WO | WO 99/48869 | A1 | 9/1999 |
| WO | WO 99/55673 | A1 | 11/1999 |
| WO | WO 99/66795 | A1 | 12/1999 |
| WO | WO 00/35278 | A1 | 6/2000 |
| WO | WO 01/17972 | A2 | 3/2001 |
| WO | WO 01/19816 | A1 | 3/2001 |
| WO | WO 01/23354 | A2 | 4/2001 |
| WO | WO 01/74770 | A1 | 10/2001 |
| WO | WO 03/010145 | A1 | 2/2003 |
| WO | WO 03/013249 | A1 | 2/2003 |
| WO | WO 03/059065 | A1 | 7/2003 |
| WO | WO 2004/007448 | A1 | 1/2004 |
| WO | WO 2004/024688 | A1 | 3/2004 |
| WO | WO 2004/065366 | A1 | 8/2004 |
| WO | WO 2004/080962 | A1 | 9/2004 |
| WO | WO 2004/111042 | A1 | 12/2004 |
| WO | WO 2005/016873 | A2 | 2/2005 |
| WO | WO 2005/044791 | A2 | 5/2005 |
| WO | WO 2005/044796 | A1 | 5/2005 |
| WO | WO 2005/048710 | A1 | 6/2005 |
| WO | WO 2005/049569 | A1 | 6/2005 |
| WO | WO 2005/066125 | A1 | 7/2005 |
| WO | WO 2005/092897 | A2 | 10/2005 |
| WO | WO 2006/000355 | A1 | 1/2006 |
| WO | WO 2006/029799 | A1 | 3/2006 |
| WO | WO 2006/056281 | A1 | 6/2006 |
| WO | WO 2006/056282 | A1 | 6/2006 |
| WO | WO 2006/089633 | A2 | 8/2006 |
| WO | WO 2007/048545 | A2 | 5/2007 |
| WO | WO 2007/068427 | A2 | 6/2007 |
| WO | WO 2007/068428 | A2 | 6/2007 |
| WO | WO 2007/073856 | A2 | 7/2007 |
| WO | WO 2007/140881 | A1 | 12/2007 |
| WO | WO 2008/067873 | A1 | 6/2008 |
| WO | WO 2008/067910 | | 6/2008 |

OTHER PUBLICATIONS

Fischer et al. (English machine translation of WO 2003059065).*

Silverman, R. B. (The Org. Chem. of Drug Design and Drug Action, Academic Press, Inc.: San Diego, 1992, pp. 4-51).*

Taylor, "An introduction to error analysis," 2nd ed. (1997), 329 pages. Chs. 1-2 provided.*

English machine translation of Fischer et al. (WO1999048869 (1999).*

English language translation of document FP103 (DE 10 2006 050 148, published Apr. 30, 2008) and document FP104 (WO 2008/067873, published Jun. 12, 2008), cited in Applicants' Information Disclosure Statement filed on Oct. 28, 2010.

English language translation of document FP94 (DE 10 2005 059 892, published Jun. 28, 2007), cited in Applicants' Information Disclosure Statement filed on Oct. 28, 2010.

Nagata, W., et al., "41. Substituted Polycyclic Compounds. VII. Cyanation of $\Delta^{1,9}$-2-Octalone(4,4a,5,6,7,8-hexahydro-2(3*H*)-naphthalenone)." *Chemical & Pharmaceutical Bulletin* II:226-235, Pharmaceutical Society of Japan, Japan (1963).

English Language Abstract for International Application Number WO 03/010145 A1, published Feb. 6, 2003, European Patent Office, espacenet database—Worldwide (2013).

Liu, C., "The Method for Preparing Fluorine-Containing Pesticides," and "Fluorine-Containing Pesticides and Intermediates," in *Collected Works of Research & Development of Novel Pesticides*, Chapters 4 and 49, Chemical Industry Press, China (2002).

Baur, P., et al., "Polydisperse Ethoxylated Fatty Alcohol Surfactants as Accelerators of Cuticular Penetration. 1. Effects of Ethoxy Chain Length and the Size of the Penetrants," *Pestic. Sci.* 51:131-152, SCI (1997).

Bhattacharya, B., "Isoquinoline Derivatives: Part XVIII—Formation of I-Alkyl-(or alkaryl or aryl)-3-methyl-7-chloro-(or 5-chloro)-isoquinolines," *Indian J. Chem. 6*:341-345, Council of Scientific and Industrial Research (1968).

Campbell, A.C., et al., "Synthesis of (E)- and (Z)- Pulvinones", *Journal of the Chemical Society, Perkin Transactions* 1:1567-1576, Royal Society of Chemistry (1985).

Compagnon, P.L., and Miocque, M., "Addition des Réactifs Nucléophiles sur la Triple Liaison Nitrile," *Ann. Chim.* 5:11-22, Masson (1970).

De Kimpe et al., "Synthesis of 1-amino-2, 2-dialkylcyclopropanecarboxylic acids from β-chloroaldimines", *Tetrahedron* 47:4123-4738, Pergamon Press plc (1991).

Deng, S. and Liu, D.M., "Studies on Phosphoroheterocycle Chemistry II: A Simple and New Route to 1, 3,2-Diazaphospholidine-4-thione 2-sulfide Derivatives", *Synthesis, Journal of Synthetic Organic Chemistry* 1 6:2445-2449, Thieme Stuttgart (2001).

Edward, J.T., and Jitrangsri, C., "Stereochemistry of the Bucherer-Bergs and Strecker Reactions of 4-*tert*-Butylcyclohexanone," *Can J. Chem.* 53:3339-3350, NRC Research Press (1975).

Harrison, H.R., et al., "Use of molecular sieves in the methyl esterification of carboxylic acids," *Chem. Ind.*, p. 1568, Society of Chemical Industry (1968).

Munday, L., "Amino-acids of the Cyclohexane Series. Part I.," *J. Chem. Soc.*, pp. 4372-4379, Royal Society of Chemistry (1961).

Schmierer, R. and Mildenberger, H., "Cyclization of N-acylalanine and N-acylglycine Esters," *Liebigs Ann. Chem.* 1985:1095-1098, VCH Verlagsgesellschaft mbH (1985).

Sonntag, N.O.V., "The Reactions of Aliphatic Acid Chlorides," *Chem. Rev.* 52:237-416, American Chemical Society (1953).

Suzuki, S., et al., "Studies on Antiviral Agents. IV. Biological Activity of Tenuazonic Acid Derivatives," *Chem. Pharm. Bull.* 15:1120-1122, Pharmaceutical Society of Japan (1967).

International Search Report for International Application No. PCT/EP2007/010103, European Patent Office, Netherlands, mailed on Mar. 5, 2008.

Dialog File 351, Accession No. 4963457, Derwent WPI English language abstract for EP 0 346 620 A1 (listed on accompanying PTO/SB/08A as document FP14), (1989).

Patent Abstract of Japan, English language abstract of Japanese Patent 2000-053670 (listed on accompanying PTO/SB/08A as document FP64), (2000).

Dialog File 351, Accession No. 17343120, Derwent WPI English language abstract for DE 10 2005 059 892 A1 (listed on accompanying PTO/SB/08A as document FP94), (2007).

Dialog File 351, Accession No. 18216296, Derwent WPI English language abstract for DE 10 2006 050 148 A1 and WO 08/067873 A1 (listed on accompanying PTO/SB/08A as documents FP103 and FP104, respectively), (2008).

Henecka and Houben-Weyl, *Methoden der Organishchen Chemie*, 8:467-469 (1952).

* cited by examiner

BIPHENYL-SUBSTITUTED SPIROCYCLIC KETOENOLS

This application is a U.S. National Stage of International Application No. PCT/EP2007/010103, filed Nov. 22, 2007, which claims the benefit of German Patent Application No. 10 2006 057 036.7, filed Dec. 4, 2006.

The present invention relates to novel biphenyl-substituted spirocyclic ketoenols, to a plurality of processes for their preparation and to their use as pesticides and/or herbicides. The invention also provides selective herbicidal compositions comprising, firstly, the biphenyl-substituted spirocyclic ketoenols and, secondly, a crop plant compatibility-improving compound.

The present invention further relates to the boosting of the action of the crop protection compositions comprising, in particular, biphenyl-substituted spirocyclic ketoenols, through the addition of ammonium salts or phosphonium salts and optionally penetrants, to the corresponding compositions, to processes for producing them and to their application in crop protection as insecticides and/or acaricides and/or for preventing unwanted plant growth.

For 3-acylpyrrolidine-2,4-diones pharmaceutical properties have been previously described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). Biological activity of these compounds has not been described.

EP-A-0 262 399 and GB-A-2 266 888 disclose similarly structured compounds (3-arylpyrrolidine-2,4-diones) for which, however, no herbicidal, insecticidal or acaricidal action has been disclosed. Known compounds with herbicidal, insecticidal or acaricidal action are unsubstituted, bicyclic 3-arylpyrrolidine-2,4-dione derivatives (EP-A-355 599, EP-A-415 211 and JP-A-12-053 670) and also substituted monocyclic 3-arylpyrrolidine-2,4-dione derivatives (EP-A-377 893 and EP-A-442 077).

Additionally known are polycyclic 3-arylpyrrolidine-2,4-dione derivatives (EP-A-442 073) and also 1H-arylpyrrolidinedione derivatives (EP-A-456 063, EP-A-521 334, EP-A-596 298, EP-A-613 884, EP-A-613 885, WO 95/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/16748, WO 99/24437, WO 99/43649, WO 99/48869 and WO 99/55673, WO 01/17972, WO 01/23354, WO 01/74770, WO 03/013249, WO 04/007448, WO 04/024688, WO 04/065366, WO 04/080962, WO 04/111042, WO 05/044791, WO 05/044796, WO 05/048710, WO 05/049596, WO 05/066125, WO 05/092897, WO 06/000355, WO 06/029799, WO 06/056281, WO 06/056282, WO 06/089633, WO 07/048,545, and WO 07/073,856, DE-05/059892, DE-06/007882, DE-06/018828, DE-06/025874, DE-06/050148).

Also known are biphenyl-substituted 1H-pyrrolidinedione derivatives having fungicidal action (WO 03/059065).

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methylphenyl)-4-hydroxy-5-(4-fluorophenyl)-$\Delta^3$-dihydrofuranone-(2)) is likewise described in DE-A-4 014 420. Similarly structured compounds without any insecticidal and/or acaricidal activity stated are known from the publication Campbell et al., J. Chem. Soc., Perkin Trans. 1, 1985, (8) 1567-76. Furthermore known are 3-aryl-$\Delta^3$-dihydrofuranone derivatives having herbicidal, acaricidal and insecticidal properties, from EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770, WO 03/013249, WO 04/024688, WO 04/080962, WO 04/111042, WO 05/092897, WO 06/000355, WO 06/029799, WO 06/089633, WO 07/048,545, WO 07/073,856, DE-06/007882.

However, in particular at low application rates and concentrations, the activity and activity spectrum of these compounds is not always fully satisfactory. Furthermore, the compatibility of these compounds with some crop plants is not always sufficient. Moreover, the toxicological properties and/or environmental properties of these compounds are not always fully satisfactory.

This invention now provides novel compounds of the formula (I)

(I)

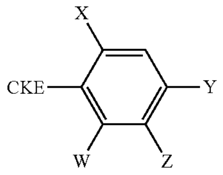

in which

X represents halogen, alkyl, alkoxy, haloalkyl or haloalkoxy,

Z represents optionally mono- or polysubstituted fluorophenyl,

W and Y independently of one another represent hydrogen, halogen, alkyl, alkoxy, haloalkyl or haloalkoxy, CKE represents one of the groups (1)

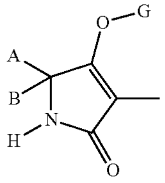

or (2)

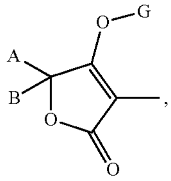

, in which

A and B together with the carbon atoms to which they are attached represent a saturated or unsaturated, unsubstituted or substituted cycle which optionally contains at least one heteroatom, G represents hydrogen (a) or represents one of the groups (b)

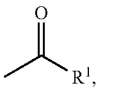

-continued (c)

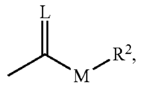

(d)

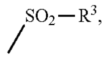

(e)

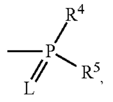

(f)

E or (g)

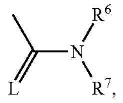

in which

E represents a metal ion or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio and $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl or together with the nitrogen atom to which they are attached represent a ring which is optionally interrupted by oxygen or sulphur.

Depending inter alia on the nature of the substituents, the compounds of the formula (I) may be present as geometrical and/or optical isomers or isomer mixtures of varying composition which, if appropriate, may be separated in a customary manner. The present invention provides for the pure isomers and the isomer mixtures, their preparation and use and compositions comprising them. However, for the sake of simplicity, hereinbelow only compounds of the formula (I) are referred to, although what is meant are both the pure compounds and, if appropriate, mixtures having various proportions of isomeric compounds.

Including the meanings (1) and (2) of the group CKE, the following principle structures (I-1) and (I-2) result:

(I-1)

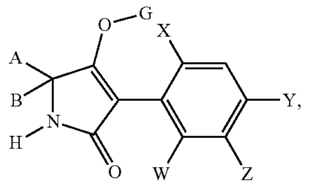

(I-2)

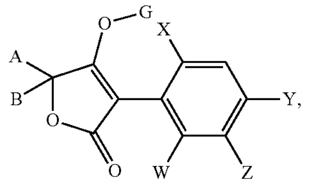

in which

A, B, G, W, X, Y and Z have the meaning given above.

Including the different meanings (a), (b), (c), (d), (e), (f) and (g) of group G, the following principle structures (I-1-a) to (I-1-g) result if CKE represents the group (1)

(I-1-a):

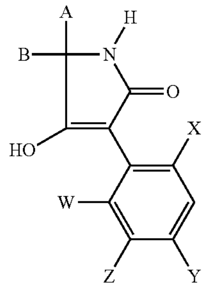

(I-1-b):

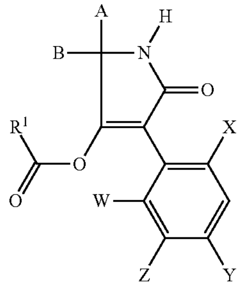

(I-1-c):

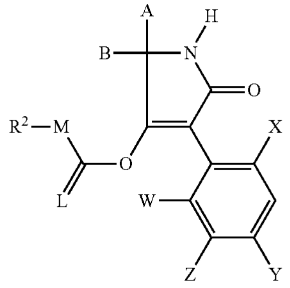

-continued
(I-1-d):
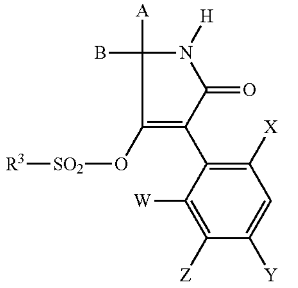
(I-1-e):
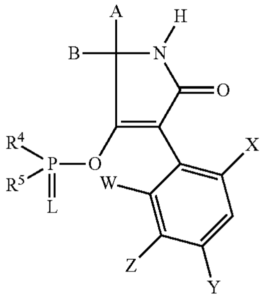
(I-1-f):
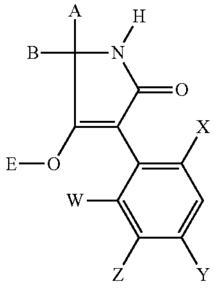
(I-1-g):
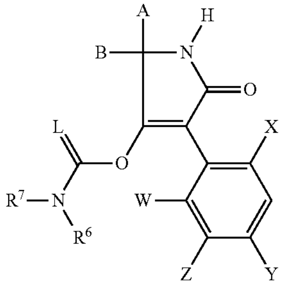
in which
A, B, E, L, M, W, X, Y, Z, $R^1$, $R^2$, $R^3$, $R^4$, $R^5$, $R^6$ and $R^7$ have the meanings given above.
Including the different meanings (a), (b), (c), (d), (e), (f) and (g) of group G, the following principle structures (I-2-a) to (I-2-g) result if CKE represents the group (2)
(I-2-a):
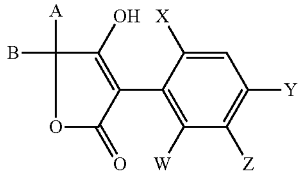
(I-2-b):
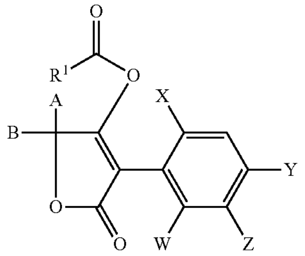
(I-2-c):
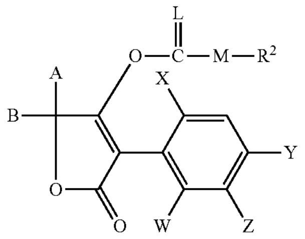
(I-2-d):
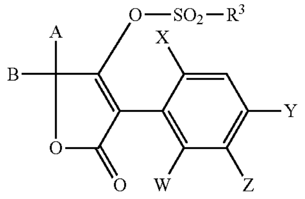
(I-2-e):
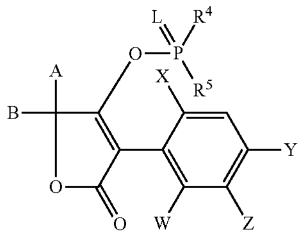
(I-2-f):
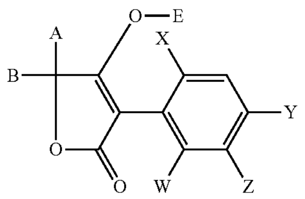

-continued (I-2-g):

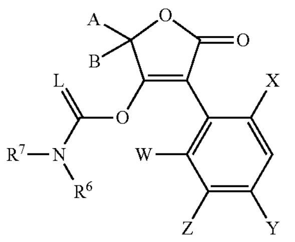

in which

A, B, E, L, M, W, X, Y, Z, $R^1$, $R^2$, $R^3$, $R^4$, $R^5$, $R^6$ and $R^7$ have the meanings given above.

Furthermore, it has been found that the novel compounds of the formula (I) are obtained by one of the processes described below:

(A) substituted 3-biphenylpyrrolidine-2,4-diones or enols thereof of the formula (I-1-a)

(I-1-a)

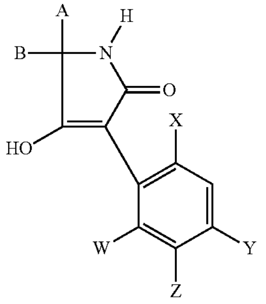

in which

A, B, W, X, Y and Z have the meanings given above are obtained when

N-acylamino acid esters of the formula (II)

(II)

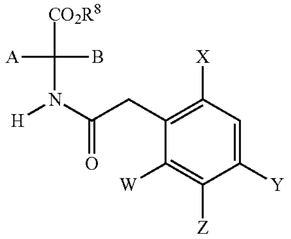

in which

A, B, W, X, Y and Z have the meanings given above and $R^8$ represents alkyl (preferably $C_1$-$C_6$-alkyl)

are condensed intramolecularly in the presence of a diluent and in the presence of a base.

(B) Moreover, it has been found that substituted 3-biphenyl-4-hydroxy-$\Delta^3$-dihydrofuranone derivatives of the formula (I-2-a)

(I-2-a)

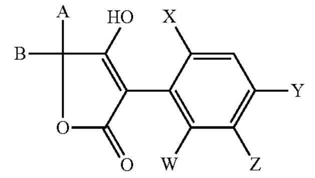

in which

A, B, W, X, Y and Z have the meanings given above are obtained when carboxylic esters of the formula (III)

(III)

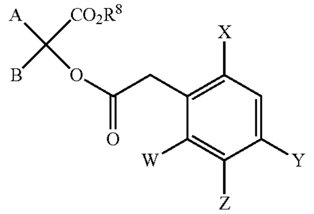

in which

A, B, W, X, Y, Z and $R^8$ have the meanings given above are condensed intramolecularly in the presence of a diluent and in the presence of a base.

(C) Furthermore, it has been found that compounds of the formulae (I-1-a) to (I-2-g) shown above in which A, B, G, W, X, Y and Z have the meaning given above are obtained when compounds of the formulae (I-1'-a) to (I-2'-g), (I-1′-a) to (I-1′-g)

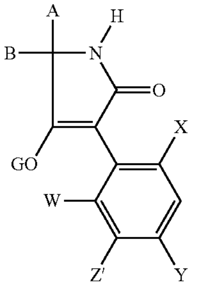

(I-2′-a) to (I-2′-g)

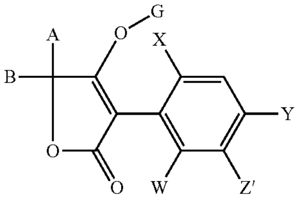

in which

A, B, D, G W, X and Y have the meaning given above and

Z' represents chlorine, bromine, iodine, preferably bromine, are reacted with boronic acids or boronic acid derivatives of the formula (IV)

(IV)

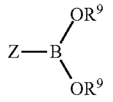

in which $R^9$ represents hydrogen, $C_1$-$C_6$-alkyl or $C_2$-$C_6$-alkanediyl and Z has the meaning given above in the presence of a diluent, a base and a catalyst, suitable catalysts being in particular palladium salts or palladium complexes.

Moreover, it has been found (D) that the compounds of the formulae (I-1-b) to (I-2-b) shown above in which A, B, $R^1$, W, X, Y and Z have the meanings given above are obtained when compounds of the formulae (I-1-a) to (I-2-a) shown above in which A, B, W, X, Y and Z have the meanings given above are in each case reacted (α) with acid halides of the formula (V)

(V)

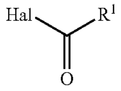

in which $R^1$ has the meaning given above and

Hal represents halogen (in particular chlorine or bromine)

or (β) with carboxylic anhydrides of the formula (VI)

$R^1$—CO—O—CO—$R^1$ (VI)

in which $R^1$ has the meaning given above, if appropriate in the presence of a diluent and if appropriate in the presence of an acid binder;

(E) that the compounds of the formulae (I-1-c) to (I-2-c) shown above in which A, B, $R^2$, M, W, X, Y and Z have the meanings given above and L represents oxygen are obtained when compounds of the formulae (I-1-a) to (I-2-a) shown above in which A, B, W, X, Y and Z have the meanings given above are in each case reacted with chloroformic esters or chloroformic thioesters of the formula (VII)

$R^2$-M-CO—Cl (VII)

in which $R^2$ and M have the meanings given above, if appropriate in the presence of a diluent and if appropriate in the presence of an acid binder;

(F) that compounds of the formulae (I-1-c) to (I-2-c) shown above in which A, B, $R^2$, M, W, X, Y and Z have the meanings given above and L represents sulphur are obtained when compounds of the formulae (I-1-a) to (I-2-a) shown above in which A, B, W, X, Y and Z have the meanings given above are in each case reacted with chloromonothioformic esters or chlorodithioformic esters of the formula (VIII)

(VIII)

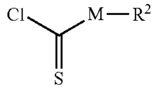

in which

M and $R^2$ have the meanings given above, if appropriate in the presence of a diluent and if appropriate in the presence of an acid binder, (G) that compounds of the formulae (I-1-d) to (I-2-d) shown above in which A, B, $R^3$, W, X, Y and Z have the meanings given above are obtained when compounds of the formulae (I-1-a) to (I-2-a) shown above in which A, B, W, X, Y and Z have the meanings given above are in each case reacted with sulphonyl chlorides of the formula (IX)

$R^3$—$SO_2$—Cl (IX)

in which $R^3$ has the meaning given above, if appropriate in the presence of a diluent and if appropriate in the presence of an acid binder, (H) that compounds of the formulae (I-1-e) to (I-2-e) shown above in which A, B, L, $R^4$, $R^5$, W, X, Y and Z have the meanings given above are obtained when compounds of the formulae (I-1-a) to (I-2-a) shown above in which A, B, W, X, Y and Z have the meanings given above are in each case reacted with phosphorus compounds of the formula (X)

(X)

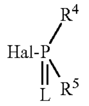

in which

L, $R^4$ and $R^5$ have the meanings given above and

Hal represents halogen (in particular chlorine or bromine), if appropriate in the presence of a diluent and if appropriate in the presence of an acid binder, (I) that compounds of the formulae (I-14) to (I-2-f) shown above in which A, B, E, W, X, Y and Z have the meanings given above are obtained when compounds of the formulae (I-1-a) to (I-2-a) shown above in which A, B, W, X, Y and Z have the meanings given above are in each case reacted with metal compounds or amines of the formulae (XI) and (XII), respectively $Me(OR^{10})_t$ (XI)

(XII)

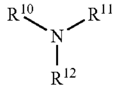

in which

Me represents a mono- or divalent metal (preferably an alkali metal or alkaline earth metal, such as lithium, sodium, potassium, magnesium or calcium), t represents the number 1 or 2 and $R^{10}$, $R^{11}$, $R^{12}$ independently of one another represent hydrogen or alkyl (preferably $C_1$-$C_8$-alkyl), if appropriate in the presence of a diluent, (J) that compounds of the formulae (I-1-g) to (I-2-g) shown above in which A, B, L, $R^6$, $R^7$, W, X, Y and Z have the meanings given above are obtained when compounds of the formulae (I-1-a) to (I-2-a) shown above in which A, B, W, X, Y and Z have the meanings given above are in each case reacted (α) with isocyanates or isothiocyanates of the formula (XIII)

$R^6$—N=C=L (XIII)

in which $R^6$ and L have the meanings given above, if appropriate in the presence of a diluent and if appropriate in the presence of a catalyst, or (β) with carbamoyl chlorides or thiocarbamoyl chlorides of the formula (XIV)

(XIV)

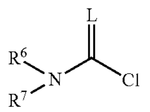

in which

L, $R^6$ and $R^7$ have the meanings given above, if appropriate in the presence of a diluent and if appropriate in the presence of an acid binder.

Furthermore, it has been found that the novel compounds of the formula (I) are very effective as pesticides, preferably as insecticides and/or acaricides and/or herbicides, that they are additionally frequently tolerated very well by plants, in particular by crop plants, and/or that they have favourable toxicological and/or environmental properties.

Surprisingly, it has now also been found that certain biphenyl-substituted spirocyclic ketoenols, when used together with the crop plant compatibility-improving compounds (safeners/antidotes) described below, efficiently prevent damage to the crop plants and can be used in a particularly advantageous manner as broad-spectrum combination preparations for the selective control of unwanted plants in crops of useful plants, such as, for example, in cereals, but also in maize, soybeans and rice.

The invention also provides selective herbicidal compositions comprising an effective amount of an active compound combination comprising, as components, (a') at least one biphenyl-substituted spirocyclic ketoenol of the formula (I) in which CKE, W, X, Y and Z have the meaning given above and (b') at least one crop plant compatibility-improving compound from the following group of compounds:

4-dichloroacetyl-1-oxa-4-azaspiro[4.5]decane(AD-67, MON-4660), 1-dichloroacetyl-hexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate(cloquintocet-mexyl-cf. also related compounds in EP-A-86750, EP-A-94349, EP-A-191736, EP-A-492366), 3-(2-chlorobenzyl)-1-(1-methyl-1-phenylethyl)urea(cumyluron), α-(cyanomethoximino)phenylacetonitrile(cyometrinil), 2,4-dichlorophenoxyacetic acid(2,4-D), 4-(2,4-dichlorophenoxy)butyric acid(2,4-DB), 1-(1-methyl-1-phenylethyl)-3-(4-methylphenyl)urea(daimuron, dymron), 3,6-dichloro-2-methoxybenzoic acid(dicamba), S-1-methyl-1-phenylethyl piperidine-1-thiocarboxylate(dimepiperate), 2,2-dichloro-N-(2-oxo-2-(2-propenylamino)ethyl)-N-(2-propenyl)-acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate(fenchlorazole-ethyl-cf. also related compounds in EP-A-174562 and EP-A-346620), phenylmethyl 2-chloro-4-trifluoromethylthiazole-5-carboxylate(flurazole), 4-chloro-N-(1,3-dioxolan-2-ylmethoxy)-α-trifluoroacetophenone oxime(fluxofenim), 3-dichloroacetyl-5-(2-furanyl)-2,2-dimethyloxazolidine(furilazole, MON-13900), ethyl 4,5-dihydro-5,5-diphenyl-3-isoxazolecarboxylate (isoxadifen-ethyl-cf. also related compounds in WO-A-95/07897), 1-(ethoxycarbonyl)ethyl 3,6-dichloro-2-methoxybenzoate(lactidichlor), (4-chloro-o-tolyloxy) acetic acid(MCPA), 2-(4-chloro-o-tolyloxy)propionic acid(mecoprop), diethyl 1-(2,4-dichorophenyl)-4,5-dihydro-5-methyl-1H-pyrazole-3,5-dicarboxylate (mefenpyr-diethyl-cf. also related compounds in WO-A-91/07874), 2-dichloromethyl-2-methyl-1,3-dioxolane(MG-191), 2-propenyl-1-oxa-4-azaspiro[4.5] decane-4-carbodithioate(MG-838), 1,8-naphthalic anhydride, α-(1,3-dioxolan-2-ylmethoximino)phenylacetonitrile(oxabetrinil), 2,2-dichloro-N-(1,3-dioxolan-2-ylmethyl)-N-(2-propenyl)acetamide(PPG-1292), 3-dichloroacetyl-2,2-dimethyl-oxazolidine(R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chloro-phenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluoro-phenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloro-quinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulphonylbenzene, 1-[4-(N-2-methoxybenzoylsulphamoyl)phenyl]-3-methylurea (also known as N-(2-methoxybenzoyl)-4-[(methylaminocarbonyl)amino]benzenesulphonamide), 1-[4-(N-2-methoxybenzoylsulphamoyl)phenyl]-3,3-dimethylurea, 1-[4-(N-4,5-dimethylbenzoyl-sulphamoyl) phenyl]-3-methylurea, 1-[4-(N-naphthylsulphamoyl)

phenyl]-3,3-dimethylurea, N-(2-methoxy-5-methylbenzoyl)-4-(cyclopropylaminocarbonyl) benzenesulphonamide, and/or one of the following compounds, defined by general formulae of the general formula (IIa)

(IIa)

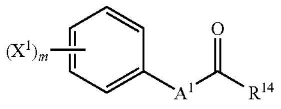

or of the general formula (IIb)

(IIb)

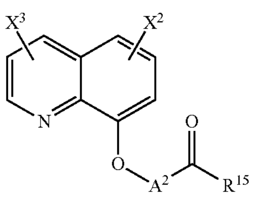

or of the formula (IIc)

(IIc)

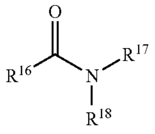

where m represents a number 0, 1, 2, 3, 4 or 5, $A^1$ represents one of the divalent heterocyclic groupings shown below

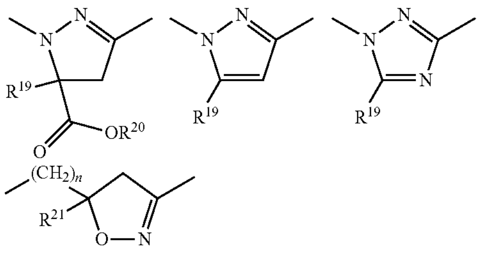

n represents a number 0, 1, 2, 3, 4 or 5, $A^2$ represents optionally $C_1$-$C_4$-alkyl- and/or $C_1$-$C_4$-alkoxy-carbonyl- and/or $C_1$-$C_4$-alkenyloxycarbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino, $R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino, $R^{16}$ represents optionally fluorine-, chlorine- and/or bromine-substituted $C_1$-$C_4$-alkyl, $R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$ alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, in each case optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae of the general formula (IId)

(IId)

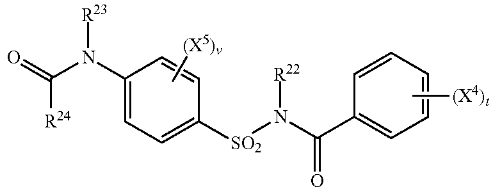

or of the general formula (IIe)

(IIe)

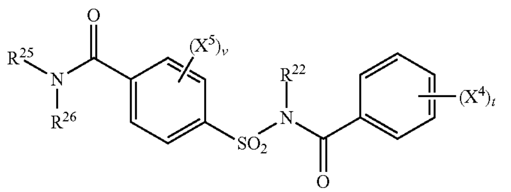

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$- alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals listed in the formulae mentioned above and below are illustrated below:

X preferably represents halogen, $C_1$-$C_6$-alkyl, $C_1$-$C_6$-haloalkyl, $C_1$-$C_6$-alkoxy or $C_1$-$C_6$-haloalkoxy, Z preferably represents a radical

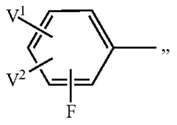

$V^1$ preferably represents hydrogen, halogen, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro or cyano, $V^2$ preferably represents hydrogen, halogen, $C_1$-$C_6$-alkyl or $C_1$-$C_6$-alkoxy, W and Y independently of one another preferably represent hydrogen, halogen, $C_1$-$C_6$-alkyl, $C_1$-$C_6$-haloalkyl, $C_1$-$C_6$-alkoxy or $C_1$-$C_6$-haloalkoxy, CKE preferably represents one of the groups (1)

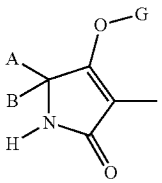

or

-continued (2)

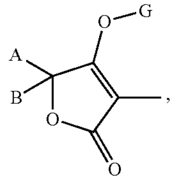

A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulphur and which is optionally mono- or disubstituted by $C_1$-$C_8$-alkyl, $C_1$-$C_6$-alkyloxy-$C_1$-$C_6$-alkyl, $C_3$-$C_{10}$-cycloalkyl, $C_3$-$C_6$-cycloalkyl-$C_1$-$C_2$-alkoxy, $C_1$-$C_8$-haloalkyl, $C_1$-$C_6$-alkoxy-$C_1$-$C_4$-alkoxy, $C_1$-$C_8$-alkylthio, halogen or phenyl or A, B and the carbon atom to which they are attached preferably represent $C_3$-$C_6$-cycloalkyl which is substituted by an alkylenediyl group which is optionally substituted by $C_1$-$C_4$-alkyl or $C_1$-$C_4$-alkoxy-$C_1$-$C_2$-alkyl and optionally contains one or two not directly adjacent oxygen and/or sulphur atoms, or by an alkylenedioxyl or by an alkylenedithioyl group which, together with the carbon atom to which it is attached, forms a further five- to eight-membered ring or A, B and the carbon atom to which they are attached preferably represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanediendiyl in which optionally one methylene group is replaced by oxygen or sulphur, or A, B and the carbon atom to which they are attached preferably represent $—CH_2—CHO—C_1$-$C_8$-alkyl-$(CH_2)_2—$, $—CH_2—CHO—C_1$-$C_8$-alkyl-$(CH_2)_3—$, G preferably represents hydrogen (a) or represents one of the groups (b)

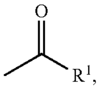

(c)

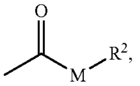

(d)

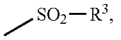

(e)

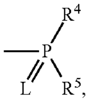

(f)

E or (g)

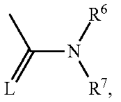

in particular (a), (b) or (c), in which

E represents a metal ion or an ammonium ion,

L represents oxygen or sulphur and

M represents oxygen or sulphur, $R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl (for example pyrazolyl, thiazolyl, pyridyl, pyrimidyl, furenyl or thienyl)

represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one methylene group is replaced by oxygen or sulphur.

In the radical definitions mentioned as being preferred, halogen represents fluorine, chlorine, bromine and iodine, in particular fluorine, chlorine and bromine.

W particularly preferably represents hydrogen, methyl or chlorine,

X particularly preferably represents fluorine, chlorine, bromine, $C_1$-$C_4$-alkyl, $C_1$-$C_4$-alkoxy, $C_1$-$C_4$-haloalkyl or $C_1$-$C_4$-haloalkoxy, Y particularly preferably represents hydrogen, $C_1$-$C_4$-alkyl, fluorine, chlorine, bromine, methoxy or trifluoromethyl, Z particularly preferably represents the radical

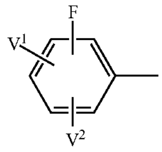

, $V^1$ particularly preferably represents hydrogen, fluorine, chlorine, bromine, $C_1$-$C_6$-alkyl, $C_1$-$C_4$-alkoxy, $C_1$-$C_2$-haloalkyl or $C_1$-$C_2$-haloalkoxy, $V^2$ particularly preferably represents hydrogen, fluorine, chlorine, bromine, $C_1$-$C_4$-alkyl or $C_1$-$C_4$-alkoxy, CKE particularly preferably represents one of the groups (1)

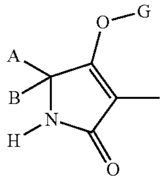

or (2)

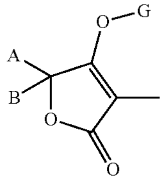

A, B and the carbon atom to which they are attached particularly preferably represent saturated or unsaturated $C_3$-$C_7$-cycloalkyl in which optionally one ring member is replaced by oxygen or sulphur and which is optionally mono- or disubstituted by $C_1$-$C_6$-alkyl, $C_1$-$C_4$-alkoxy-$C_1$-$C_2$-alkyl, trifluoromethyl, $C_1$-$C_3$-alkoxy-$C_1$-$C_3$-alkoxy or $C_3$-$C_6$-cycloalkylmethoxy or A, B and the carbon atom to which they are attached particularly preferably represent $C_5$-$C_6$-cycloalkyl which is substituted by an alkylenediyl group which is optionally substituted by methyl, ethyl or methoxymethyl and optionally contains one or two not directly adjacent oxygen or sulphur atoms, or by an alkylenedioxyl or by an alkylenedithiol group which, together with the carbon atom to which it is attached, forms a further five- or six-membered ring or A, B and the carbon atom to which they are attached particularly preferably represent $C_5$-$C_6$-cycloalkyl or $C_5$-$C_6$-cycloalkenyl in which two substituents together with the carbon atoms to which they are attached represent in each case optionally $C_1$-$C_2$-alkyl-, $C_1$-$C_2$-alkoxy-substituted $C_2$-$C_4$-alkanediyl, $C_2$-$C_4$-alkenediyl or butadienediyl, or A, B and the carbon atom to which they are attached particularly preferably represent —$CH_2$—CHO—$C_1$-$C_6$-alkyl-$(CH_2)_2$—, —$CH_2$—CHO—$C_1$-$C_6$-alkyl-$(CH_2)_3$—, G particularly preferably represents hydrogen (a) or represents one of the groups (b)

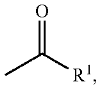

(c)

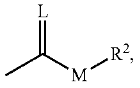

(d)

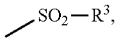

(e)

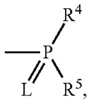

(f)

E or (g)

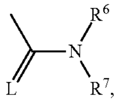

in which

E represents a metal ion equivalent or an ammonium ion,

L represents oxygen or sulphur and

M represents oxygen or sulphur, $R^1$ particularly preferably represents $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen, represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ particularly preferably represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine, represents $C_3$-$C_6$-cycloalkyl which is optionally monosubstituted by $C_1$-$C_2$-alkyl or $C_1$-$C_2$-alkoxy or represents phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl or trifluoromethoxy, $R^3$ particularly preferably represents $C_1$-$C_8$-alkyl which is optionally mono- to trisubstituted by fluorine or represents phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or represents phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl, $R^5$ particularly preferably represents $C_1$-$C_6$-alkoxy or $C_1$-$C_6$-alkylthio, $R^6$ particularly preferably represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ particularly preferably represents $C_1$-$C_6$-alkyl, $C_3$-$C_6$-alkenyl or $C_1$-$C_6$-alkoxy-$C_1$-$C_4$-alkyl, $R^6$ and $R^7$ together particularly preferably represent an optionally methyl- or ethyl-substituted $C_4$-$C_5$-alkylene radical in which optionally one methylene group is replaced by oxygen or sulphur.

In the radical definitions mentioned as being particularly preferred, halogen represents fluorine, chlorine and bromine, in particular fluorine and chlorine.

W very particularly preferably represents hydrogen or methyl,

X very particularly preferably represents fluorine, chlorine, methyl, ethyl, propyl, isopropyl, methoxy, ethoxy, propoxy, isopropoxy, trifluoromethyl, difluoromethoxy or trifluoromethoxy, Y very particularly preferably represents hydrogen, methyl, fluorine or chlorine, Z very particularly preferably represents the radical

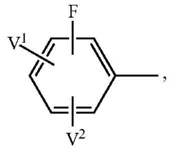

, $V^1$ very particularly preferably represents hydrogen, fluorine, chlorine, methyl, ethyl, methoxy, ethoxy, trifluoromethyl or trifluoromethoxy, $V^2$ very particularly preferably represents hydrogen, fluorine, chlorine, methyl or methoxy, CKE very particularly preferably represents one of the groups (1)

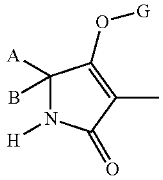

or (2)

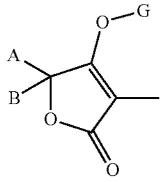

A, B and the carbon atom to which they are attached very particularly preferably represent saturated $C_5$-$C_6$-cycloalkyl in which optionally one ring member is replaced by oxygen or sulphur and which is optionally mono- or disubstituted by methyl, ethyl, propyl, isopropyl, methoxymethyl, ethoxymethyl, propoxymethyl, methoxyethyl, ethoxyethyl, trifluoromethyl, methoxyethoxy, ethoxyethoxy or cyclopropylmethoxy, or A, B and the carbon atom to which they are attached very particularly preferably represent $C_6$-cycloalkyl which is optionally substituted by an alkylenedioxyl group which contains two not directly adjacent oxygen atoms, or

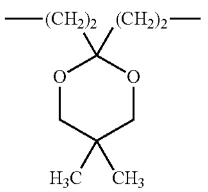

A, B and the carbon atom to which they are attached very particularly preferably represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, or A, B and the carbon atom to which they are attached very particularly preferably represent $-CH_2-CHOCH_3-(CH_2)_2-$, $-CH_2-CHOC_2H_5-(CH_2)_2-$, $-CH_2-CHOC_3H_7-(CH_2)_2-$, $-CH_2-CHOC_4-H_9-(CH_2)_2-$, $-CH_2-CHOCH_3-(CH_2)_3-$, $-CH_2-CHOC_2H_5-(CH_2)_3-$, $-CH_2-CHOC_3H_7-(CH_2)_3-$, $-CH_2-CHOC_4H_9-(CH_2)_3-$, G very particularly preferably represents hydrogen (a) or represents one of the groups (b)

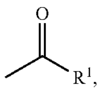

(c)

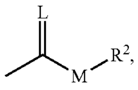

or (f)

E, in which

L represents oxygen or sulphur,

M represents oxygen or sulphur and

E represents a metal ion equivalent or an ammonium ion, $R^1$ very particularly preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ very particularly preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine, W especially preferably represents hydrogen or methyl, X especially preferably represents chlorine or methyl (notably methyl), Y especially preferably represents hydrogen or methyl, Z especially preferably represents the radical

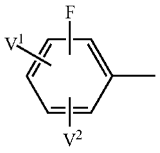

(notably)

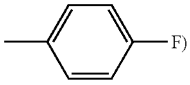

), $V^1$ especially preferably represents hydrogen, fluorine or chlorine, $V^2$ especially preferably represents hydrogen or fluorine, CKE especially preferably represents the group (1)

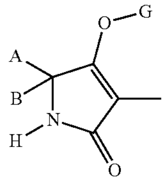

,

A, B and the carbon atom to which they are attached especially preferably represent saturated $C_5$-$C_6$-cycloalkyl which is optionally mono- or disubstituted by methyl, ethyl, methoxymethyl, ethoxymethyl, methoxyethyl, ethoxyethyl, trifluoromethyl, methoxyethoxy, ethoxyethoxy or cyclopropylmethoxy (notably monosubstituted by methoxyethoxy), G especially preferably represents hydrogen (a) or represents one of the groups (b)

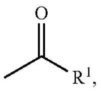

(c)

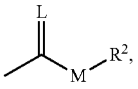

or (f)

E, (notably the group (a))

in which

L represents oxygen or sulphur,

M represents oxygen or sulphur and

E represents a metal ion equivalent or an ammonium ion, $R^1$ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine, furthermore W especially preferably represents hydrogen or methyl, X especially preferably represents chlorine or methyl, Y especially preferably represents hydrogen or methyl, Z especially preferably represents the radical

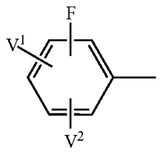

$V^1$ especially preferably represents hydrogen, fluorine, chlorine, methyl, methoxy or trifluoromethyl, $V^2$ especially preferably represents hydrogen or fluorine, CKE especially preferably represents the group (1)

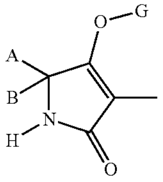

A, B and the carbon atom to which they are attached especially preferably represent saturated $C_6$-cycloalkyl in which one ring member is replaced by oxygen and which is optionally monosubstituted by methyl or ethyl, G especially preferably represents hydrogen (a) or represents one of the groups (b)

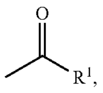

(c)

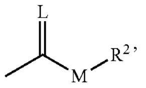

or (f)

E, in which

L represents oxygen,

M represents oxygen and

E represents a metal ion equivalent or an ammonium ion (notably sodium or potassium), $R^1$ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine, also W especially preferably represents hydrogen or methyl, X especially preferably represents chlorine or methyl (notably methyl), Y especially preferably represents hydrogen or methyl (notably hydrogen), Z especially preferably represents the radical

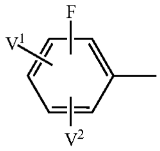

(notably 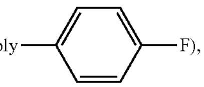), $V^1$ especially preferably represents hydrogen, fluorine or chlorine, $V^2$ especially preferably represents hydrogen or fluorine, CKE especially preferably represents the group (1)

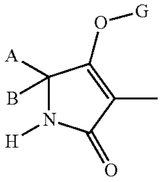

A, B and the carbon atom to which they are attached especially preferably represent $C_6$-cycloalkyl which is substituted by $—O—(CH_2)_2—O—$, $—O—(CH_2)_3—O—$, or represent

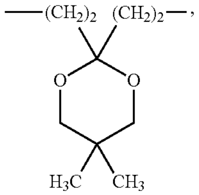

G especially preferably represents hydrogen (a) or represents one of the groups (b)

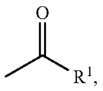

(c)

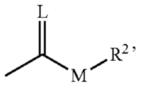

or (f)

E, (notably hydrogen (a)), in which

L represents oxygen or sulphur,

M represents oxygen or sulphur and

E represents a metal ion equivalent or an ammonium ion, $R^1$ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine, moreover W especially preferably represents hydrogen or methyl, X especially preferably represents chlorine or methyl (notably methyl), Y especially preferably represents hydrogen or methyl (notably hydrogen), Z especially preferably represents the radical

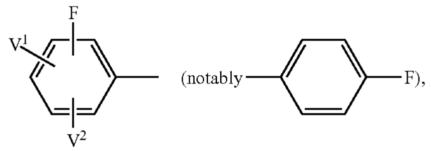

$V^1$ especially preferably represents hydrogen, fluorine or chlorine, $V^2$ especially preferably represents hydrogen or fluorine, CKE especially preferably represents the group (1)

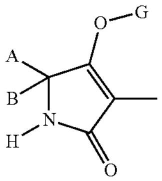

A, B and the carbon atom to which they are attached especially preferably represent —$CH_2$—$CHOCH_3$—$(CH_2)_2$—, —$CH_2$—$CHOC_2H_5$—$(CH_2)_2$—, —$CH_2$—$CHOC_3H_7$—$(CH_2)_2$—, —$CH_2$—$CHOC_4$—$H_9$—$(CH_2)_2$—, —$CH_2$—$CHOCH_3$—$(CH_2)_3$—, —$CH_2$—$CHOC_2H_5$—$(CH_2)_3$—, —$CH_2$—$CHOC_3H_7$—$(CH_2)_3$, —$CH_2$—$CHOC_4H_9$—$(CH_2)_3$—, (notably —$CH_2$—$CHOCH_3$—$(CH_2)_2$—, —$CH_2$—$CHOC_2H_5$—$(CH_2)_3$—, —$CH_2$—$CHOCH_3$—$(CH_2)_3$—), G especially preferably represents hydrogen (a) or represents one of the groups (b)

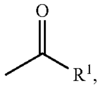

(c)

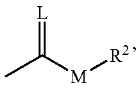

or (f)

E, (notably hydrogen (a)), in which

L represents oxygen or sulphur,

M represents oxygen or sulphur and

E represents a metal ion equivalent or an ammonium ion, $R^1$ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine, also W especially preferably represents hydrogen or methyl, X especially preferably represents chlorine or methyl, Y especially preferably represents hydrogen or methyl, Z especially preferably represents the radical

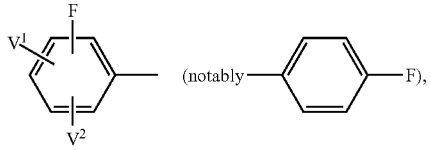

$V^1$ especially preferably represents hydrogen, fluorine or chlorine, $V^2$ especially preferably represents hydrogen or fluorine, CKE especially preferably represents the group (2)

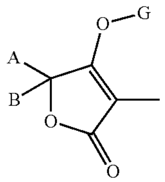

A, B and the carbon atom to which they are attached especially preferably represent saturated $C_5$-$C_6$-cycloalkyl which is optionally mono- or disubstituted by methyl, ethyl, methoxymethyl, ethoxymethyl, methoxyethyl, ethoxyethyl, trifluoromethyl, methoxyethoxy, ethoxyethoxy or cyclopropylmethoxy, or G especially preferably represents hydrogen (a) or represents one of the groups (b)

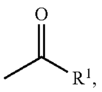

(c)

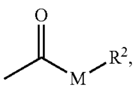

in which

L represents oxygen and

M represents oxygen, $R^1$ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine, also W especially preferably represents hydrogen or methyl, X especially preferably represents chlorine or methyl, Y especially preferably represents hydrogen or methyl, Z especially preferably represents the radical

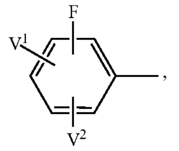

$V^1$ especially preferably represents hydrogen, fluorine or chlorine, $V^2$ especially preferably represents hydrogen or fluorine, CKE especially preferably represents the group (2)

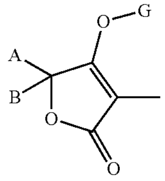

A, B and the carbon atom to which they are attached especially preferably represent saturated $C_6$-cycloalkyl in which one ring member is replaced by oxygen and which is optionally monosubstituted by methyl or ethyl, G especially preferably represents hydrogen (a) or represents one of the groups (b)

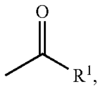

(c)

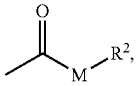

in which

L represents oxygen and

M represents oxygen, $R^1$ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted fluorine, also W especially preferably represents hydrogen or methyl, X especially preferably represents chlorine or methyl, Y especially preferably represents hydrogen or methyl, Z especially preferably represents the radical

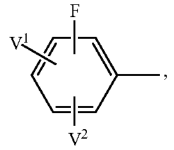

$V^1$ especially preferably represents hydrogen, fluorine or chlorine, $V^2$ especially preferably represents hydrogen or fluorine, CKE especially preferably represents the group (2)

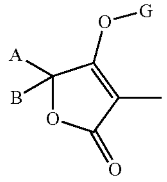

A, B and the carbon atom to which they are attached especially preferably represent $C_6$-cycloalkyl which is substituted by —O—$(CH_2)_2$—O— or —O—$(CH_2)_3$—O—, or G especially preferably represents hydrogen (a) or represents one of the groups (b)

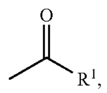

(c)

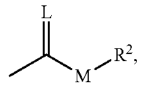

or (f)

E, in which

L represents oxygen or sulphur,

M represents oxygen or sulphur and

E represents a metal ion equivalent or an ammonium ion, $R^1$ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine, moreover W especially preferably represents hydrogen or methyl, X especially preferably represents chlorine or methyl, Y especially preferably represents hydrogen or methyl, Z especially preferably represents the radical

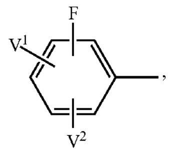

$V^1$ especially preferably represents hydrogen, fluorine or chlorine, $V^2$ especially preferably represents hydrogen or fluorine, CKE especially preferably represents the group (2)

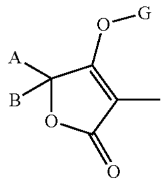

A, B and the carbon atom to which they are attached especially preferably represent $—CH_2—CHOCH_3—(CH_2)_2—$, $—CH_2—CHOC_2H_5—(CH_2)_2—$, $—CH_2—CHOC_3H_7—(CH_2)_2—$, $—CH_2—CHOC_4—H_9—(CH_2)_2—$, $—CH_2—CHOCH_3—(CH_2)_3—$, $—CH_2—CHOC_2H_5—(CH_2)_3—$, $—CH_2—CHOC_3H_7—(CH_2)_3—$, $—CH_2—CHOC_4H_9—(CH_2)_3—$, G especially preferably represents hydrogen (a) or represents one of the groups (b)

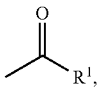

(c)

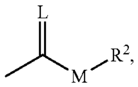

or (f)

E, in which

L represents oxygen or sulphur,

M represents oxygen or sulphur and

E represents a metal ion equivalent or an ammonium ion, $R^1$ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ especially preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine.

The general or preferred radical definitions listed above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

Noteworthy are compounds where Z=

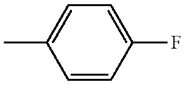

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals may be mono- or polysubstituted unless indicated otherwise, and in the case of multiple substitutions the substituents can be identical or different.

In addition to the compounds mentioned in the examples, the following compounds of the formula (I) may be specifically mentioned:

(I)

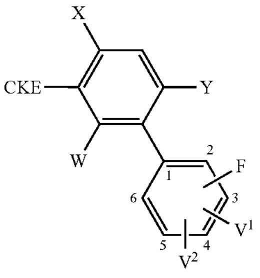

TABLE 1

| W | X | Y | F | $V^1$ | $V^2$ |
|---|---|---|---|---|---|
| H | Cl | H | 2 | H | H |
| H | Cl | H | 3 | H | H |
| H | Cl | H | 4 | H | H |
| H | Cl | H | 2 | 4-F | H |
| H | Cl | H | 2 | 4-Cl | H |
| H | Cl | H | 2 | 4-$CH_3$ | H |
| H | Cl | H | 2 | 4-$OCH_3$ | H |
| H | Cl | H | 3 | 4-F | H |

TABLE 1-continued

| W | X | Y | F | $V^1$ | $V^2$ |
|---|---|---|---|---|---|
| H | Cl | H | 3 | 4-Cl | H |
| H | Cl | H | 3 | 4-$CH_3$ | H |
| H | Cl | H | 3 | 4-$OCH_3$ | H |
| H | Cl | H | 4 | 3-Cl | H |
| H | Cl | H | 4 | 3-$CH_3$ | H |
| H | Cl | H | 4 | 3-$OCH_3$ | H |
| H | Cl | H | 2 | 4-F | 5-F |
| H | Cl | H | 2 | 4-F | 6-F |
| H | Cl | H | 2 | 4-Cl | 5-F |
| H | Cl | H | 2 | 5-Cl | 4-F |
| H | Cl | H | 3 | 4-F | 5-F |
| H | $CH_3$ | H | 2 | H | H |
| H | $CH_3$ | H | 3 | H | H |
| H | $CH_3$ | H | 4 | H | H |
| H | $CH_3$ | H | 2 | 4-F | H |
| H | $CH_3$ | H | 2 | 4-Cl | H |
| H | $CH_3$ | H | 2 | 4-$CH_3$ | H |
| H | $CH_3$ | H | 2 | 4-$OCH_3$ | H |
| H | $CH_3$ | H | 3 | 4-F | H |
| H | $CH_3$ | H | 3 | 4-Cl | H |
| H | $CH_3$ | H | 3 | 4-$CH_3$ | H |
| H | $CH_3$ | H | 3 | 4-$OCH_3$ | H |
| H | $CH_3$ | H | 4 | 3-Cl | H |
| H | $CH_3$ | H | 4 | 3-$CH_3$ | H |
| H | $CH_3$ | H | 4 | 3-$OCH_3$ | H |
| H | $CH_3$ | H | 2 | 4-F | 5-F |
| H | $CH_3$ | H | 2 | 4-F | 6-F |
| H | $CH_3$ | H | 2 | 4-Cl | 5-F |
| H | $CH_3$ | H | 2 | 5-Cl | 4-F |
| H | $CH_3$ | H | 3 | 4-F | 5-F |
| $CH_3$ | $CH_3$ | H | 2 | H | H |
| $CH_3$ | $CH_3$ | H | 3 | H | H |
| $CH_3$ | $CH_3$ | H | 4 | H | H |
| $CH_3$ | $CH_3$ | H | 2 | 4-F | H |
| $CH_3$ | $CH_3$ | H | 2 | 4-Cl | H |
| $CH_3$ | $CH_3$ | H | 2 | 4-$CH_3$ | H |
| $CH_3$ | $CH_3$ | H | 2 | 4-$OCH_3$ | H |
| $CH_3$ | $CH_3$ | H | 3 | 4-F | H |
| $CH_3$ | $CH_3$ | H | 3 | 4-Cl | H |
| $CH_3$ | $CH_3$ | H | 3 | 4-$CH_3$ | H |
| $CH_3$ | $CH_3$ | H | 3 | 4-$OCH_3$ | H |
| $CH_3$ | $CH_3$ | H | 4 | 3-Cl | H |
| $CH_3$ | $CH_3$ | H | 4 | 3-$CH_3$ | H |
| $CH_3$ | $CH_3$ | H | 4 | 3-$OCH_3$ | H |
| $CH_3$ | $CH_3$ | H | 2 | 4-F | 5-F |
| $CH_3$ | $CH_3$ | H | 2 | 4-F | 6-F |
| $CH_3$ | $CH_3$ | H | 2 | 4-Cl | 5-F |
| $CH_3$ | $CH_3$ | H | 2 | 5-Cl | 4-F |
| $CH_3$ | $CH_3$ | H | 3 | 4-F | 5-F |
| H | $CH_3$ | $CH_3$ | 2 | H | H |
| H | $CH_3$ | $CH_3$ | 3 | H | H |
| H | $CH_3$ | $CH_3$ | 4 | H | H |
| H | $CH_3$ | $CH_3$ | 2 | 4-F | H |
| H | $CH_3$ | $CH_3$ | 2 | 4-Cl | H |
| H | $CH_3$ | $CH_3$ | 2 | 4-$CH_3$ | H |
| H | $CH_3$ | $CH_3$ | 2 | 4-$OCH_3$ | H |
| H | $CH_3$ | $CH_3$ | 3 | 4-F | H |
| H | $CH_3$ | $CH_3$ | 3 | 4-Cl | H |
| H | $CH_3$ | $CH_3$ | 3 | 4-$CH_3$ | H |
| H | $CH_3$ | $CH_3$ | 3 | 4-$OCH_3$ | H |
| H | $CH_3$ | $CH_3$ | 4 | 3-Cl | H |
| H | $CH_3$ | $CH_3$ | 4 | 3-$CH_3$ | H |
| H | $CH_3$ | $CH_3$ | 4 | 3-$OCH_3$ | H |
| H | $CH_3$ | $CH_3$ | 2 | 4-F | 5-F |
| H | $CH_3$ | $CH_3$ | 2 | 4-F | 6-F |
| H | $CH_3$ | $CH_3$ | 2 | 4-Cl | 5-F |
| H | $CH_3$ | $CH_3$ | 2 | 5-Cl | 4-F |
| H | $CH_3$ | $CH_3$ | 3 | 4-F | 5-F |
| $CH_3$ | $CH_3$ | $CH_3$ | 2 | H | H |
| $CH_3$ | $CH_3$ | $CH_3$ | 3 | H | H |
| $CH_3$ | $CH_3$ | $CH_3$ | 4 | H | H |
| $CH_3$ | $CH_3$ | $CH_3$ | 2 | 4-F | H |
| $CH_3$ | $CH_3$ | $CH_3$ | 2 | 4-Cl | H |
| $CH_3$ | $CH_3$ | $CH_3$ | 2 | 4-$CH_3$ | H |
| $CH_3$ | $CH_3$ | $CH_3$ | 2 | 4-$OCH_3$ | H |
| $CH_3$ | $CH_3$ | $CH_3$ | 3 | 4-F | H |
| $CH_3$ | $CH_3$ | $CH_3$ | 3 | 4-Cl | H |
| $CH_3$ | $CH_3$ | $CH_3$ | 3 | 4-$CH_3$ | H |

TABLE 1-continued

| W | X | Y | F | $V^1$ | $V^2$ |
|---|---|---|---|---|---|
| $CH_3$ | $CH_3$ | $CH_3$ | 3 | 4-$OCH_3$ | H |
| $CH_3$ | $CH_3$ | $CH_3$ | 4 | 3-Cl | H |
| $CH_3$ | $CH_3$ | $CH_3$ | 4 | 3-$CH_3$ | H |
| $CH_3$ | $CH_3$ | $CH_3$ | 4 | 3-$OCH_3$ | H |
| $CH_3$ | $CH_3$ | $CH_3$ | 2 | 4-F | 5-F |
| $CH_3$ | $CH_3$ | $CH_3$ | 2 | 4-F | 6-F |
| $CH_3$ | $CH_3$ | $CH_3$ | 2 | 4-Cl | 5-F |
| $CH_3$ | $CH_3$ | $CH_3$ | 2 | 5-Cl | 4-F |
| $CH_3$ | $CH_3$ | $CH_3$ | 3 | 4-F | 5-F |

Especially preferred active compounds according to the invention are compounds having the radical combinations for W, X, Y, F, $V^1$ and $V^2$ listed in Table 1 and the radical combinations for A and B listed in Table 2.

TABLE 2

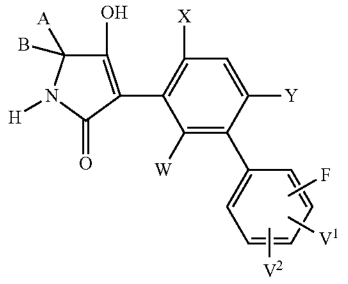

CKE = (1)

| A | B |
|---|---|
| $—(CH_2)_2—$ | |
| $—(CH_2)_4—$ | |
| $—(CH_2)_5—$ | |
| $—(CH_2)_6—$ | |
| $—(CH_2)_7—$ | |
| $—CH_2—CHCH_3—O—(CH_2)_2—$ | |
| $—(CH_2)_2—O—(CH_2)_2—$ | |
| $—CH_2—O—(CH_2)_3—$ | |
| $—(CH_2)_2—S—(CH_2)_2—$ | |
| $—CH_2—CHCH_3—(CH_2)_3—$ | |
| $—CH_2—CHOCH_3—(CH_2)_2—$ | |
| $—CH_2—CHOC_2H_5—(CH_2)_2—$ | |
| $—CH_2—CHOC_3H_7—(CH_2)_2—$ | |
| $—CH_2—CHOC_4H_9—(CH_2)_2—$ | |
| $—CH_2—CHO(CH_2)_2OCH_3—(CH_2)_2—$ | |
| 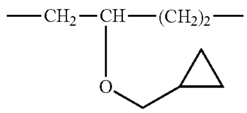 | |
| $—CH_2—CHOCH_3—(CH_2)_3$ | |
| $—CH_2—CHOC_2H_5—(CH_2)_3$ | |
| $—CH_2—CHOC_3H_7—(CH_2)_3$ | |
| $—CH_2—CHOC_4H_9—(CH_2)_3$ | |
| $—CH_2—CHO(CH_2)_2OCH_3—(CH_2)_3$ | |
| 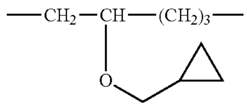 | |
| $—(CH_2)_2—CHCH_3—(CH_2)_2$ | |
| $—(CH_2)_2—CHC_2H_5—(CH_2)_2—$ | |
| $—(CH_2)_2—CHC_3H_7—(CH_2)_2—$ | |
| $—(CH_2)_2—CHi\text{-}C_3H_7—(CH_2)_2—$ | |
| $—(CH_2)_2—C(CH_3)_2—(CH_2)_2$ | |
| $—CH_2—(CHCH_3)_2—(CH_2)_2—$ | |

TABLE 2-continued
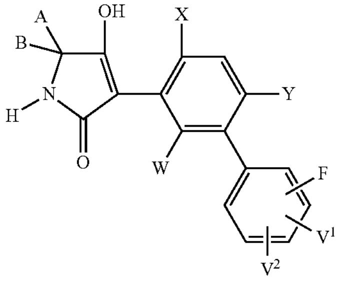
CKE = (1)
| A | B |
|---|---|
| 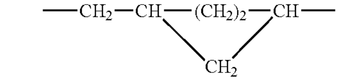 | |
| 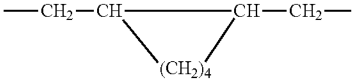 | |
| 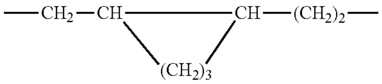 | |
| 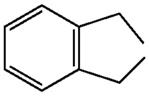 | |
| 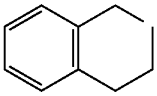 | |
| 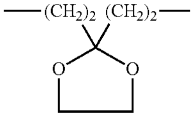 | |
| 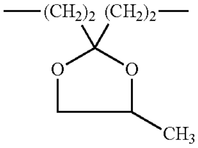 | |
| 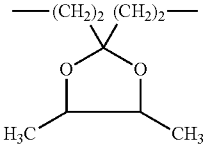 | |
| 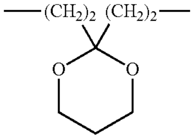 | |
| 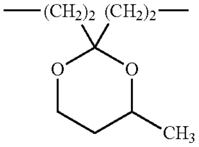 | |
TABLE 2-continued
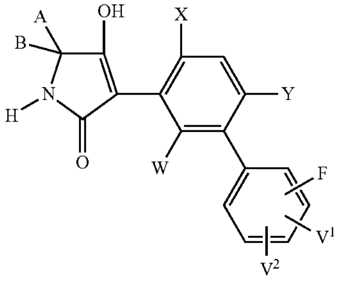
CKE = (1)
| A | B |
|---|---|
| 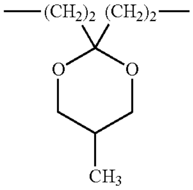 | |
| 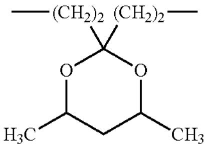 | |
| 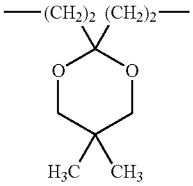 | |
| 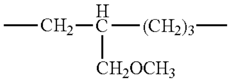 | |
| 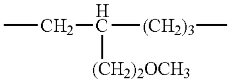 | |
| 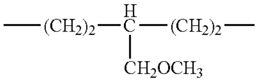 | |
| 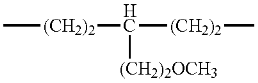 | |
| 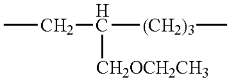 | |
| 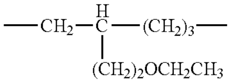 | |
| 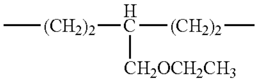 | |

TABLE 2-continued

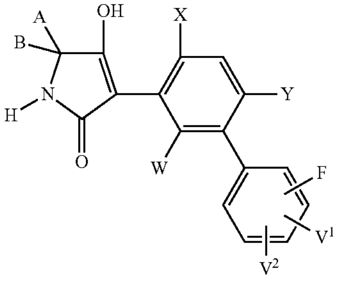

CKE = (1)

| A | B |
|---|---|
| 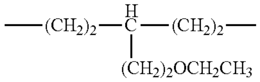 | |

Especially preferred active compounds according to the invention are compounds having the radical combinations for W, X, Y, F, $V^1$ and $V^2$ listed in Table 1 and the radical combinations for A and B listed in Table 3.

TABLE 3

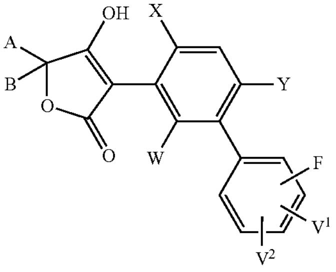

CKE = (2)

| A | B |
|---|---|
| $—(CH_2)_2—$ | |
| $—(CH_2)_4—$ | |
| $—(CH_2)_5—$ | |
| $—(CH_2)_6—$ | |
| $—(CH_2)_7—$ | |
| $—CH_2—CHCH_3—O—(CH_2)_2—$ | |
| $—(CH_2)_2—O—(CH_2)_2—$ | |
| $—CH_2—O—(CH_2)_3—$ | |
| $—(CH_2)_2—S—(CH_2)_2—$ | |
| $—CH_2—CHCH_3—(CH_2)_3—$ | |
| $—CH_2—CHOCH_3—(CH_2)_3—$ | |
| $—CH_2—CHOC_2H_5—(CH_2)_3—$ | |
| $—CH_2—CHOC_3H_7—(CH_2)_3—$ | |
| $—CH_2—CHOC_4H_9—(CH_2)_3—$ | |
| $—CH_2—CHO(CH_2)_2OCH_3—(CH_2)_3—$ | |
| $—(CH_2)_2—CHCH_3—(CH_2)_2—$ | |
| $—(CH_2)_2—CHC_2H_5—(CH_2)_2—$ | |
| $—(CH_2)_2—CHC_3H_7—(CH_2)_2—$ | |
| $—(CH_2)_2—CHi\text{-}C_3H_7—(CH_2)_2—$ | |
| $—(CH_2)_2—C(CH_3)_2—(CH_2)_2—$ | |
| $—CH_2—(CHCH_3)_2—(CH_2)_2—$ | |
| 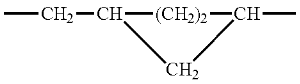 | |

TABLE 3-continued

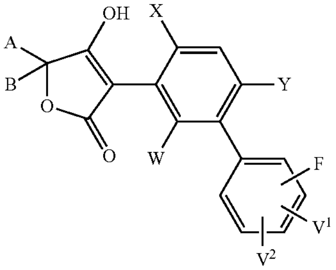

CKE = (2)

| A | B |
|---|---|
| 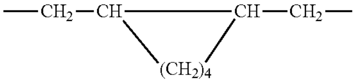 | |
| 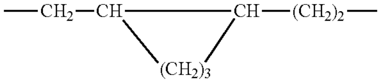 | |
| 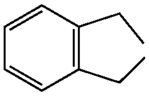 | |
| 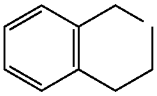 | |
| 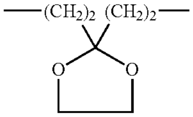 | |
| 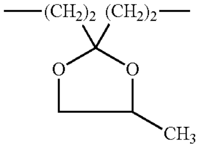 | |
| 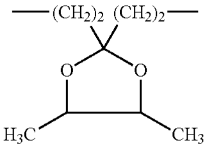 | |
| 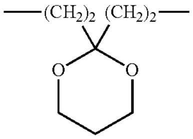 | |
| 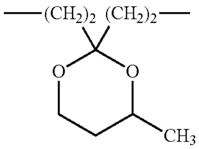 | |

TABLE 3-continued

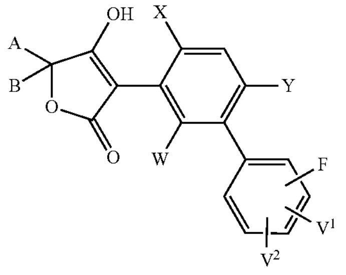

CKE = (2)

| A | B |
|---|---|
| 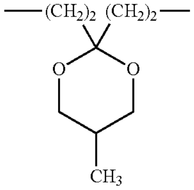 | |
| 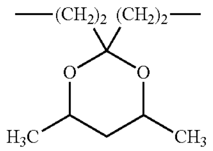 | |
| 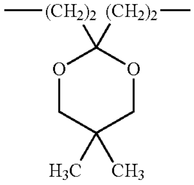 | |
| 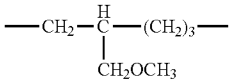 | |
| 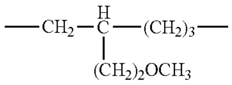 | |
| 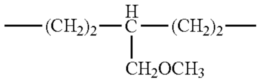 | |
| 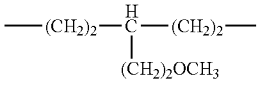 | |
| 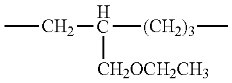 | |
| 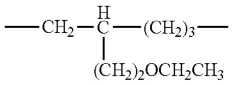 | |
| 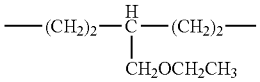 | |

TABLE 3-continued

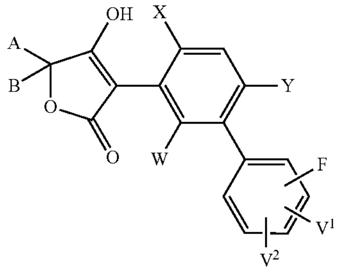

CKE = (2)

| A | B |
|---|---|
| 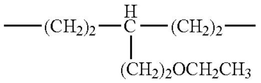 | |

Preferred meanings of the groups listed above in connection with the crop plant compatibility-improving compounds ("herbicide safeners") of the formulae (IIa), (IIb), (IIc), (IId) and (IIe) are defined below.

m preferably represents the numbers 0, 1, 2, 3 or 4.

$A^1$ preferably represents one of the divalent heterocyclic groupings shown below

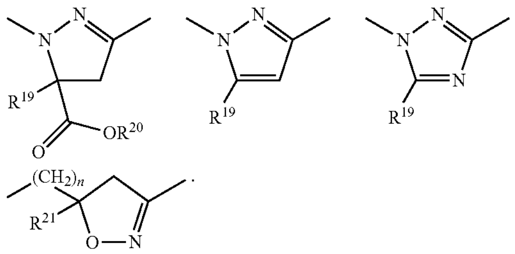

n preferably represents the numbers 0, 1, 2, 3 or 4.

$A^2$ preferably represents in each case optionally methyl-, ethyl-, methoxycarbonyl-, ethoxycarbonyl-, or alkyloxycarbonyl-substituted methylene or ethylene.

$R^{14}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{15}$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{16}$ preferably represents in each case optionally fluorine-, chlorine- and/or bromine-substituted methyl, ethyl, n- or i-propyl.

$R^{17}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, s- or t-butyl-substituted phenyl.

$R^{18}$ preferably represents hydrogen, in each case optionally fluorine- and/or chlorine-substituted methyl, ethyl, n- or i-propyl, n-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, s- or t-butyl-substituted phenyl, or together with $R^{17}$ represents one of the radicals $—CH_2—O—CH_2—CH_2—$ and $—CH_2—CH_2—O—CH_2—CH_2—$ which are optionally substituted by methyl, ethyl, furyl, phenyl, a fused benzene ring or by two substituents which, together with the C atom to which they are attached, form a 5- or 6-membered carbocycle.

$R^{19}$ preferably represents hydrogen, cyano, fluorine, chlorine, bromine, or represents in each case optionally fluorine-, chlorine- and/or bromine-substituted methyl, ethyl, n- or i-propyl, cyclo-propyl, cyclobutyl, cyclopentyl, cyclohexyl or phenyl.

$R^{20}$ preferably represents hydrogen, optionally hydroxyl-, cyano-, fluorine-, chlorine-, methoxy-, ethoxy-, n- or i-propoxy-substituted methyl, ethyl, n- or i-propyl, n-, s- or t-butyl.

$R^{21}$ preferably represents hydrogen, cyano, fluorine, chlorine, bromine, or represents in each case optionally fluorine-, chlorine- and/or bromine-substituted methyl, ethyl, n- or i-propyl, n-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, s- or t-butyl, difluoromethyl, dichloromethyl, trifluoromethyl, trichloromethyl, chloro-difluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

$X^3$ preferably represents hydrogen, nitro, cyano, fluorine, chlorine, bromine, methyl, ethyl, n- or i-propyl, n-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

t preferably represents the numbers 0, 1, 2, 3 or 4.

v preferably represents the numbers 0, 1, 2, 3, or 4.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclo-pentyl, cyclohexyl, cyclopropyloxy, cyclobutyloxy, cyclopentyloxy, cyclohexyloxy, cyclo-propylthio, cyclobutylthio, cyclopentylthio, cyclohexylthio, cyclopropylamino, cyclobutyl-amino, cyclopentylamino or cyclohexylamino.

$R^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl(trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoro-methyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoro-methyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

TABLE

Examples of the compounds of the formula (IIa)

(IIa)

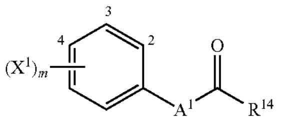

| Example No. | (Positions) $(X^1)_m$ | $A^1$ | $R^{14}$ |
|---|---|---|---|
| IIa-1 | (2) Cl, (4) Cl | 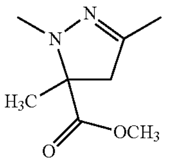 | $OCH_3$ |
| IIa-2 | (2) Cl, (4) Cl | 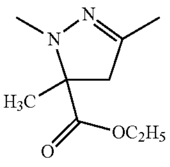 | $OCH_3$ |

TABLE-continued
Examples of the compounds of the formula (IIa)
(IIa)
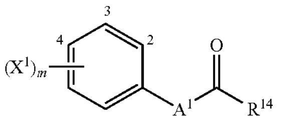
(IIa)
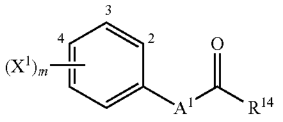
| Example No. | (Positions) $(X^1)_m$ | $A^1$ | $R^{14}$ |
| --- | --- | --- | --- |
| IIa-3 | (2) Cl, (4) Cl | 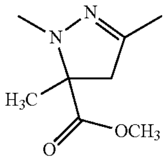 | $OC_2H_5$ |
| IIa-4 | (2) Cl, (4) Cl | 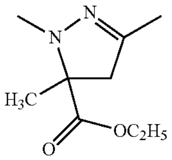 | $OC_2H_5$ |
| IIa-5 | (2) Cl | 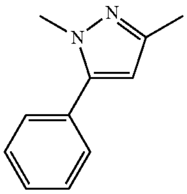 | $OCH_3$ |
| IIa-6 | (2) Cl, (4) Cl | 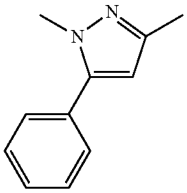 | $OCH_3$ |
| IIa-7 | (2) F | 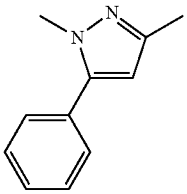 | $OCH_3$ |
| IIa-8 | (2) F | 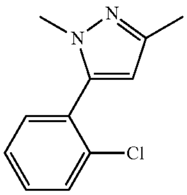 | $OCH_3$ |
| IIa-9 | (2) Cl, (4) Cl | 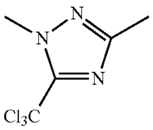 | $OC_2H_5$ |
| IIa-10 | (2) Cl, (4) $CF_3$ | 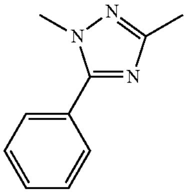 | $OCH_3$ |
| IIa-11 | (2) Cl | 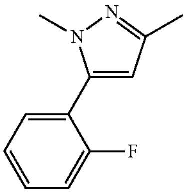 | $OCH_3$ |
| IIa-12 | — | 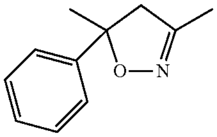 | $OC_2H_5$ |
| IIa-13 | (2) Cl, (4) Cl | 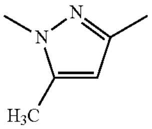 | $OC_2H_5$ |
| IIa-14 | (2) Cl, (4) Cl | 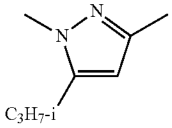 | $OC_2H_5$ |
| IIa-15 | (2) Cl, (4) Cl | 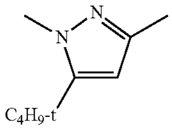 | $OC_2H_5$ |
| IIa-16 | (2) Cl, (4) Cl | 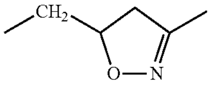 | $OC_2H_5$ |
| IIa-17 | (2) Cl, (4) Cl | 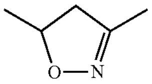 | $OC_2H_5$ |
| IIa-18 | — | 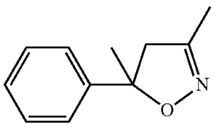 | OH |

Examples of the compounds of the formula (IIb) which are very particularly preferred as herbicide safeners according to the invention are listed in the table below.

TABLE

Examples of the compounds of the formula (IIb)

(IIb)

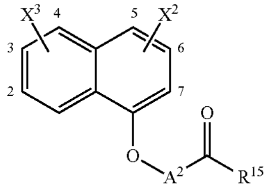

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH{=}CH_2$ |
| IIb-11 | (5) Cl | — | $CH_2$ | $OC_4H_9$-i |
| IIb-12 | (5) Cl | — | $CH_2$ | 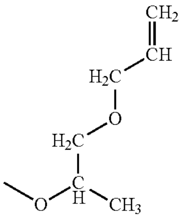 |
| IIb-13 | (5) Cl | — | 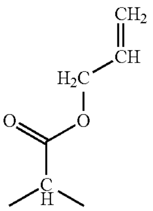 | $OCH_2CH{=}CH_2$ |
| IIb-14 | (5) Cl | — | 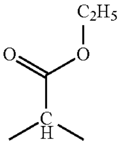 | $OC_2H_5$ |

TABLE-continued

Examples of the compounds of the formula (IIb)

(IIb)

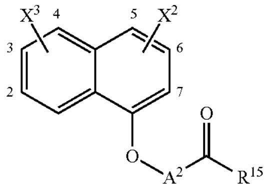

| Example No. | (Position) $X^2$ | (Position) $X^3$ | $A^2$ | $R^{15}$ |
|---|---|---|---|---|
| IIb-15 | (5) Cl | — | 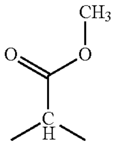 | $OCH_3$ |

Examples of the compounds of the formula (IIc) which are very particularly preferred as herbicide safeners according to the invention are listed in the table below.

TABLE

Example of the compounds of the formula (IIc)

(IIc)

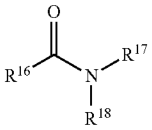

| Example No. | $R^{16}$ | $N(R^{17}, R^{18})$ |
|---|---|---|
| IIc-1 | $CHCl_2$ | $N(CH_2CH{=}CH_2)_2$ |
| IIc-2 | $CHCl_2$ | 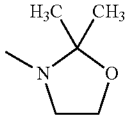 |
| IIc-3 | $CHCl_2$ | 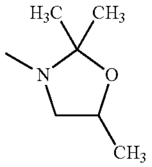 |
| IIc-4 | $CHCl_2$ | 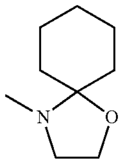 |
| IIc-5 | $CHCl_2$ | 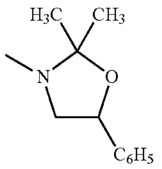 |

TABLE-continued

Example of the compounds of the formula (IIc)

(IIc)

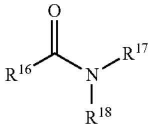

| Example No. | $R^{16}$ | $N(R^{17}, R^{18})$ |
|---|---|---|
| IIc-6 | $CHCl_2$ | 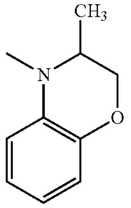 |
| IIc-7 | $CHCl_2$ | 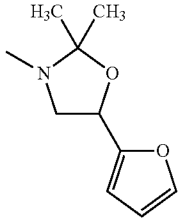 |

Examples of the compounds of the formula (IId) which are very particularly preferred as herbicide safeners according to the invention are listed in the table below.

TABLE

Example of the compounds of the formula (IId)

(IId)

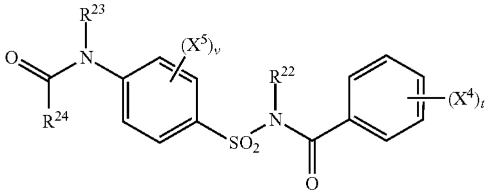

| Example No. | $R^{22}$ | $R^{23}$ | $R^{24}$ | (Positions) $(X^4)_t$ | (Positions) $(X^5)_v$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$—I | (2) $OCH_3$ | — |
| IId-5 | H | H | 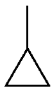 | (2) $OCH_3$ | — |
| IId-6 | H | H | $CH_3$ | (2) $OCH_3$ (5) $CH_3$ | — |
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$—I | (2) $OCH_3$ (5) $CH_3$ | — |

TABLE-continued

Example of the compounds of the formula (IId)

(IId)

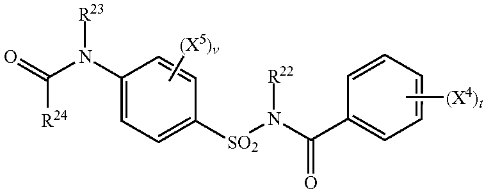

| Example No. | $R^{22}$ | $R^{23}$ | $R^{24}$ | (Positions) $(X^4)_t$ | (Positions) $(X^5)_v$ |
|---|---|---|---|---|---|
| IId-10 | H | H | 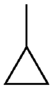 | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$—I | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$—I | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$—I | (2) $OCH_3$ (5) $CH_3$ | — |
| IId-20 | H | H | 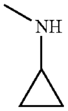 | (2) $OCH_3$ (5) $CH_3$ | — |
| IId-21 | H | H | $NHCH_3$ | (2) $OCH_3$ | — |
| IId-22 | H | H | $NHC_3H_7$—I | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2$—O—$CH_3$ | (2) $OCH_3$ | — |

Examples of the compounds of the formula (IIe) which are very particularly preferred as herbicide safeners according to the invention are listed in the table below.

TABLE

Examples of the compounds of the formula (IIe)

(IIe)

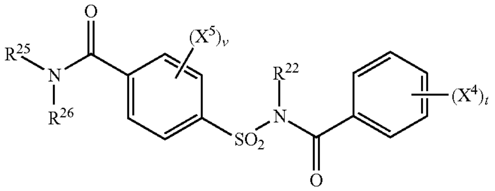

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | $CH_3$ | (2) $OCH_3$ | — |
| IIe-2 | H | H | $C_2H_5$ | (2) $OCH_3$ | — |

TABLE-continued

Examples of the compounds of the formula (IIe)

(IIe)

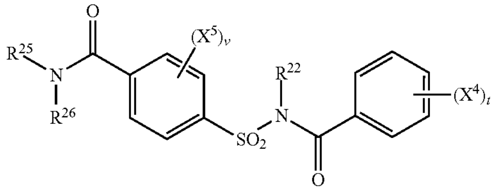

| Example No. | $R^{22}$ | $R^{25}$ | $R^{26}$ | (Positions) $(X^4)_t$ | (Positions) $(X^5)_v$ |
|---|---|---|---|---|---|
| IIe-3 | H | H | $C_3H_7$-n | (2) $OCH_3$ | — |
| IIe-4 | H | H | $C_3H_7$-i | (2) $OCH_3$ | — |
| IIe-5 | H | H | 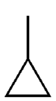 | (2) $OCH_3$ | — |
| IIe-6 | H | $CH_3$ | $CH_3$ | (2) $OCH_3$ | — |
| IIe-7 | H | H | $CH_3$ | (2) $OCH_3$<br>(5) $CH_3$ | — |
| IIe-8 | H | H | $C_2H_5$ | (2) $OCH_3$<br>(5) $CH_3$ | — |
| IIe-9 | H | H | $C_3H_7$-n | (2) $OCH_3$<br>(5) $CH_3$ | — |
| IIe-10 | H | H | $C_3H_7$-i | (2) $OCH_3$<br>(5) $CH_3$ | — |
| IIe-11 | H | H | 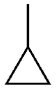 | (2) $OCH_3$<br>(5) $CH_3$ | — |
| IIe-12 | H | $CH_3$ | $CH_3$ | (2) $OCH_3$<br>(5) $CH_3$ | — |

Most preferred as crop plant compatibility-improving compound [component (b')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl, but also isoxadifen-ethyl.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/U.S. Pat. No. 6,235,680).

The compounds of the general formula (IIe) to be used as safeners according to the invention are known and can be prepared by processes known per se (cf. WO-A-99/66795/U.S. Pat. No. 6,251,827).

Examples of the selective herbicidal combinations according to the invention comprising in each case one active compound of the formula (I) and one of the safeners defined above are listed in the table below.

TABLE

Examples of combinations according to the invention

| Active compounds of the formula (I) | Safener |
|---|---|
| I-1-a | cloquintocet-mexyl |
| I-1-a | fenchlorazole-ethyl |
| I-1-a | isoxadifen-ethyl |
| I-1-a | mefenpyr-diethyl |
| I-1-a | furilazole |
| I-1-a | fenclorim |
| I-1-a | cumyluron |
| I-1-a | daimuron/dymron |
| I-1-a | dimepiperate |
| I-1-a | IIe-11 |
| I-1-a | IIe-5 |
| I-1-b | cloquintocet-mexyl |
| I-1-b | fenchlorazole-ethyl |
| I-1-b | isoxadifen-ethyl |
| I-1-b | mefenpyr-diethyl |
| I-1-b | furilazole |
| I-1-b | fenclorim |
| I-1-b | cumyluron |
| I-1-b | daimuron/dymron |
| I-1-b | dimepiperate |
| I-1-b | IIe-11 |
| I-1-b | IIe-5 |
| I-1-c | cloquintocet-mexyl |
| I-1-c | fenchlorazole-ethyl |
| I-1-c | isoxadifen-ethyl |
| I-1-c | mefenpyr-diethyl |
| I-1-c | furilazole |
| I-1-c | fenclorim |
| I-1-c | cumyluron |
| I-1-c | daimuron/dymron |
| I-1-c | dimepiperate |
| I-1-c | IIe-5 |
| I-1-c | IIe-11 |
| I-1-d | cloquintocet-mexyl |
| I-1-d | fenchlorazole-ethyl |
| I-1-d | isoxadifen-ethyl |
| I-1-d | mefenpyr-diethyl |
| I-1-d | furilazole |
| I-1-d | fenclorim |
| I-1-d | cumyluron |
| I-1-d | daimuron/dymron |
| I-1-d | dimepiperate |
| I-1-d | IIe-11 |
| I-1-d | IIe-5 |
| I-1-e | cloquintocet-mexyl |
| I-1-e | fenchlorazole-ethyl |
| I-1-e | isoxadifen-ethyl |
| I-1-e | mefenpyr-diethyl |
| I-1-e | furilazole |
| I-1-e | fenclorim |
| I-1-e | cumyluron |
| I-1-e | daimuron/dymron |
| I-1-e | dimepiperate |
| I-1-e | IIe-5 |
| I-1-e | IIe-11 |
| I-1-f | cloquintocet-mexyl |
| I-1-f | fenchlorazole-ethyl |
| I-1-f | isoxadifen-ethyl |
| I-1-f | mefenpyr-diethyl |
| I-1-f | furilazole |
| I-1-f | fenclorim |
| I-1-f | cumyluron |
| I-1-f | daimuron/dymron |
| I-1-f | dimepiperate |
| I-1-f | IIe-5 |
| I-1-f | IIe-11 |
| I-1-g | cloquintocet-mexyl |
| I-1-g | fenchlorazole-ethyl |
| I-1-g | isoxadifen-ethyl |
| I-1-g | mefenpyr-diethyl |
| I-1-g | furilazole |
| I-1-g | fenclorim |
| I-1-g | cumyluron |
| I-1-g | daimuron/dymron |
| I-1-g | dimepiperate |

TABLE-continued

Examples of combinations according to the invention

| Active compounds of the formula (I) | Safener |
|---|---|
| I-1-g | IIe-5 |
| I-1-g | IIe-11 |

TABLE

Examples of combinations according to the invention

| Active compounds of the formula (I) | Safener |
|---|---|
| I-2-a | cloquintocet-mexyl |
| I-2-a | fenchlorazole-ethyl |
| I-2-a | isoxadifen-ethyl |
| I-2-a | mefenpyr-diethyl |
| I-2-a | fiirilazole |
| I-2-a | fenclorim |
| I-2-a | cumyluron |
| I-2-a | daimuron/dymron |
| I-2-a | dimepiperate |
| I-2-a | IIe-11 |
| I-2-a | IIe-5 |
| I-2-b | cloquintocet-mexyl |
| I-2-b | fenchlorazole-ethyl |
| I-2-b | isoxadifen-ethyl |
| I-2-b | mefenpyr-diethyl |
| I-2-b | furilazole |
| I-2-b | fenclorim |
| I-2-b | cumyluron |
| I-2-b | daimuron/dymron |
| I-2-b | dimepiperate |
| I-2-b | IIe-11 |
| I-2-b | IIe-5 |
| I-2-c | cloquintocet-mexyl |
| I-2-c | fenchlorazole-ethyl |
| I-2-c | isoxadifen-ethyl |
| I-2-c | mefenpyr-diethyl |
| I-2-c | furilazole |
| I-2-c | fenclorim |
| I-2-c | cumyluron |
| I-2-c | daimuron/dymron |
| I-2-c | dimepiperate |
| I-2-c | IIe-5 |
| I-2-c | IIe-11 |
| I-2-d | cloquintocet-mexyl |
| I-2-d | fenchlorazole-ethyl |
| I-2-d | isoxadifen-ethyl |
| I-2-d | mefenpyr-diethyl |
| I-2-d | furilazole |
| I-2-d | fenclorim |
| I-2-d | cumyluron |
| I-2-d | daimuron/dymron |
| I-2-d | dimepiperate |
| I-2-d | IIe-11 |
| I-2-d | IIe-5 |
| I-2-e | cloquintocet-mexyl |
| I-2-e | fenchlorazole-ethyl |
| I-2-e | isoxadifen-ethyl |
| I-2-e | mefenpyr-diethyl |
| I-2-e | furilazole |
| I-2-e | fenclorim |
| I-2-e | cumyluron |
| I-2-e | daimuron/dymron |
| I-2-e | dimepiperate |
| I-2-e | IIe-5 |
| I-2-e | IIe-11 |
| I-2-f | cloquintocet-mexyl |
| I-2-f | fenchlorazole-ethyl |
| I-2-f | isoxadifen-ethyl |
| I-2-f | mefenpyr-diethyl |
| I-2-f | furilazole |
| I-2-f | fenclorim |
| I-2-f | cumyluron |
| I-2-f | daimuron/dymron |
| I-2-f | dimepiperate |
| I-2-f | IIe-5 |
| I-2-f | IIe-11 |
| I-2-g | cloquintocet-mexyl |
| I-2-g | fenchlorazole-ethyl |
| I-2-g | isoxadifen-ethyl |
| I-2-g | mefenpyr-diethyl |
| I-2-g | furilazole |
| I-2-g | fenclorim |
| I-2-g | cumyluron |
| I-2-g | daimuron/dymron |
| I-2-g | dimepiperate |
| I-2-g | IIe-5 |
| I-2-g | IIe-11 |

Surprisingly, it has now been found that the active compound combinations, defined above, of biphenyl-substituted spirocyclic ketoenols of the general formula (I) and safeners (antidotes) from group (b') listed above, while being very well tolerated by useful plants, have a particularly high herbicidal activity and can be used in various crops, in particular in cereals (especially wheat), but also in soya beans, potatoes, maize and rice, for the selective control of weeds.

Here, it has to be considered surprising that, from a large number of known safeners or antidotes capable of antagonizing the harmful effect of a herbicide on crop plants, those suitable are in particular the compounds of group (b') listed above which eliminate the harmful effect of biphenyl-substituted spirocyclic ketoenols on the crop plants virtually completely without having a major adverse effect on the herbicidal activity against the weeds.

Emphasis may be given here to the particularly advantageous effect of the particularly and most preferred combination partners from group (b'), in particular with respect to sparing cereal plants, such as, for example, wheat, barley and rye, but also maize and rice, as crop plants.

In the literature it has already been described how the action of various active compounds can be boosted by addition of ammonium salts. The salts in question, however, are detersive salts (for example WO 95/017817) or salts which have relatively long alkyl substituents and/or aryl substituents and which have a permeabilizing action or which increase the active compound's solubility (for example EP-A 0 453 086, EP-A 0 664 081, FR-A 2 600 494, U.S. Pat. No. 4,844,734, U.S. Pat. No. 5,462,912, U.S. Pat. No. 5,538,937, US-A 03/0224939, US-A 05/0009880, US-A 05/0096386). Moreover, the prior art describes the action only for particular active compounds and/or particular applications of the corresponding compositions. In other cases, in turn, the salts in question are those of sulphonic acids, where the acids themselves have a paralytic action on insects (U.S. Pat. No. 2,842, 476). A boost to action by ammonium sulphate, for example, is described by way of example for the herbicides glyphosate, phosphinothricin and certain cyclic ketoenols (U.S. Pat. No. 6,645,914, EP-A2 0 036 106, WO 07/068,427). A corresponding action in the case of insecticides is described for certain cyclic ketoenols in WO 07/068,428.

The use of ammonium sulphate as a formulating assistant has also been described for certain active compounds and applications (WO 92/16108), but its purpose therein is to stabilize the formulation, not to boost the action.

It has now been found, surprisingly, that the action of insecticides and/or acaricides and/or herbicides from the class of the biphenyl-substituted spirocyclic ketoenols of the formula (I) can be boosted significantly through the addition of ammonium salts or phosphonium salts to the application solution or through the incorporation of these salts into a formulation comprising biphenyl-substituted spirocyclic ketoenols of the formula (I). The present invention therefore provides for the use of ammonium salts or phosphonium salts for boosting the action of crop protection compositions which comprise as their active compound insecticidal and/or acaricidal biphenyl-substituted spirocyclic ketoenols of the formula (I). The invention likewise provides compositions which comprise herbicidal and/or acaricidal and/or insecticidal biphenyl-substituted spirocyclic ketoenols of the formula (I) and action-boosting ammonium salts or phosphonium salts, including not only formulated active compounds but also ready-to-use compositions (spray liquors). The invention further provides, finally, for the use of these compositions for controlling insect pests and/or spider mites and/or unwanted plant growth.

The compounds of the formula (I) possess a broad insecticidal and/or acaricidal and/or herbicidal activity, but in specific cases the activity and/or plant tolerance leaves something to be desired. However, some or all of these properties can be improved by adding ammonium salts or phosphonium salts.

The active compounds can be used in the compositions according to the invention in a broad concentration range. The concentration of the active compounds in the formulation is typically 0.1%-50% by weight.

The formula (III') provides a definition of the ammonium salts and phosphonium salts which, according to the invention, boost the activity of crop protection compositions comprising an active compound from the class of the biphenyl-substituted spirocyclic ketoenols of the formula (I)

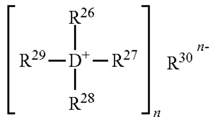

(III')

in which

D represents nitrogen or phosphorus,

D preferably represents nitrogen, $R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano, $R^{26}$, $R^{27}$, $R^{28}$ and $R^{29}$ independently of one another preferably represent hydrogen or in each case optionally substituted $C_1$-$C_4$-alkyl, the substituents being selectable from halogen, nitro and cyano, $R^{26}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl, $R^{26}$, $R^{27}$, $R^{28}$ and $R^{29}$ very particularly preferably represent hydrogen, n represents 1, 2, 3 or 4, n preferably represents 1 or 2, $R^{30}$ represents an organic or inorganic anion, $R^{30}$ preferably represents hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate, $R^{30}$ particularly preferably represents lactate, sulphate, nitrate, thiosulphate, thiocyanate, oxalate or formate.

$R^{30}$ very particularly preferably represents sulphate.

Inventively emphasized combinations of active compound, salt and penetrant are listed in the table below. "Penetrant as per test" means here that any compound that acts as a penetrant in the cuticle penetration test (Baur et al., 1997, *Pesticide Science* 51, 131-152) is suitable.

The ammonium salts and phosphonium salts of the formula (III') can be used in a broad concentration range to boost the activity of crop protection compositions comprising biphenyl-substituted spirocyclic ketoenols of the formula (I). In general the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product the ammonium salt and/or phosphonium salt concentration in the formulation is chosen such that it is within these stated general, preferred or particularly preferred ranges after the formulation has been diluted to the desired active compound concentration. The concentration of the salt in the formulation is typically 1%-50% by weight.

In one preferred embodiment of the invention the activity is boosted by adding to the crop protection compositions not only an ammonium salt and/or phosphonium salt but also, additionally, a penetrant. It is considered entirely surprising that even in these cases an even greater boost to activity is observed. The present invention therefore likewise provides for the use of a combination of penetrant and ammonium salts and/or phosphonium salts to boost the activity of crop protection compositions which comprise insecticidal biphenyl-substituted spirocyclic ketoenols of the formula (I) as active compound. The invention likewise provides compositions which comprise herbicidal and/or acaricidal and/or insecticidal biphenyl-substituted spirocyclic ketoenols of the formula (I), penetrants and ammonium salts and/or phosphonium salts, including specifically not only formulated active compounds but also ready-to-use compositions (spray liquors). The invention additionally provides, finally, for the use of these compositions for controlling harmful insects and/or spider mites.

In the present context, suitable penetrants are all those substances which are usually employed to improve penetration of agrochemically active compounds into plants. In this context, penetrants are defined in that they penetrate from the aqueous spray liquor and/or the spray coating into the cuticles of the plant, thus increasing the mobility of active compounds in the cuticles. The method described in the literature (Baur et al., 1997, *Pesticide Science* 51, 131-152) can be used for determining this property.

Examples of suitable penetrants include alkanol alkoxylates. Penetrants of the invention are alkanol alkoxylates of the formula (IV')

$$R—O-(-AO)_v—R' \qquad (IV')$$

in which

R is straight-chain or branched alkyl having 4 to 20 carbon atoms,

R' is hydrogen, methyl, ethyl, n-propyl, isopropyl, n-butyl, isobutyl, tert-butyl, n-pentyl or n-hexyl, AO is an ethylene oxide radical, a propylene oxide radical, a butylene oxide radical or is mixtures of ethylene oxide and propylene oxide radicals or butylene oxide radicals, and v is a number from 2 to 30.

One preferred group of penetrants are alkanol alkoxylates of the formula

R—O-(-EO—$)_n$—R' (IV'-a)

in which

R is as defined above,

R' is as defined above,

EO is —$CH_2$—$CH_2$—O—, and n is a number from 2 to 20.

A further preferred group of penetrants are alkanol alkoxylates of the formula

R—O-(-EO—$)_p$—(—PO—$)_q$—R' (IV'-b)

in which

R is as defined above,

R' is as defined above,

EO is —$CH_2$—$CH_2$—O—,

PO is

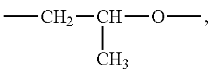

P is a number from 1 to 10, and q is a number from 1 to 10.

A further preferred group of penetrants are alkanol alkoxylates of the formula

R—O—(—PO—$)_r$-(EO—$)_s$—R' (IV'-c)

in which

R is as defined above,

R' is as defined above,

EO is —$CH_2$—$CH_2$—O—,

PO is

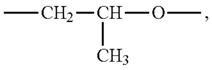

r is a number from 1 to 10, and s is a number from 1 to 10.

A further preferred group of penetrants are alkanol alkoxylates of the formula

R—O-(-EO—$)_p$—(—BO—$)_q$—R' (IV'-d)

in which

R and R' are as defined above,

EO is $CH_2$—$CH_2$—O—,

BO is

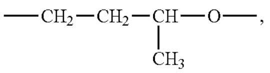

p is a number from 1 to 10 and q is a number from 1 to 10.

A further preferred group of penetrants are alkanol alkoxylates of the formula

R—O—(—BO—$)_r$-(-EO—$)_s$—R' (IV'-e)

in which

R and R' are as defined above,

BO is

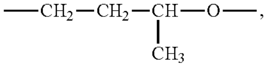

EO is $CH_2$—$CH_2$—O—, r is a number from 1 to 10 and s is a number from 1 to 10.

A further preferred group of penetrants are alkanol alkoxylates of the formula $CH_3$—$(CH_2)_t$—$CH_2$—O—(—$CH_2$—$CH_2$—O—$)_u$—R' (IV'-f)

in which

R' is as defined above, t is a number from 8 to 13, u is a number from 6 to 17.

In the formulae indicated above,

R is preferably butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV'-c) mention may be made of 2-ethylhexyl alkoxylate of the formula (IV'-c-1)

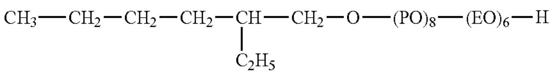

in which

EO is —$CH_2$—$CH_2$—O—,

PO is

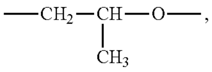

and the numbers 8 and 6 represent average values.

As an example of an alkanol alkoxylate of the formula (IV'-d) mention may be made of the formula $CH_3$—$(CH_2)_{10}$—O—(-EO—$)_6$—(—BO—$)_2$—$CH_3$ (IV'-d-1)

in which

EO is $CH_2$—$CH_2$—O—,

BO is

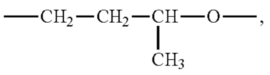

and the numbers 10, 6 and 2 represent average values.

Particularly preferred alkanol alkoxylates of the formula (IV'-f) are compounds of this formula in which t is a number from 9 to 12 and u is a number from 7 to 9.

Mention may be made with very particular preference of alkanol alkoxylate of the formula (IV'-f-1)

$CH_3$—$(CH_2)_t$—$CH_2$—O—(—$CH_2$—$CH_2$—O—$)_u$—H (IV'-f-1)

in which t stands for the average value 10.5 and u stands for the average value 8.4.

A general definition of the alkanol alkoxylates is given by the formulae above. These substances are mixtures of compounds of the stated type with different chain lengths. The indices therefore have average values which may also deviate from whole numbers.

The alkanol alkoxylates of the formulae stated are known and in some cases are available commercially or can be prepared by known methods (cf. WO 98/35 553, WO 00/35 278 and EP-A 0 681 865).

Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soya bean oil, or the esters of said oils. Preference is given to rapeseed oil, sunflower oil and their methyl or ethyl esters.

The concentration of penetrant in the compositions of the invention can be varied within a wide range. In the case of a formulated crop protection composition it is in general 1% to 95%, preferably 1% to 55%, more preferably 15%-40% by weight. In the ready-to-use compositions (spray liquors) the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth) acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions. Preference is given to alkali metal salts and alkaline earth metal salts of alkylsulphonic acids or alkylarylsulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, according to process (A), ethyl N-[6-methyl-3(4-fluorophenyl)phenylacetyl]-1-amino-cyclohexanecarboxylate as starting material, the course of the process according to the invention can be represented by the reaction scheme below:

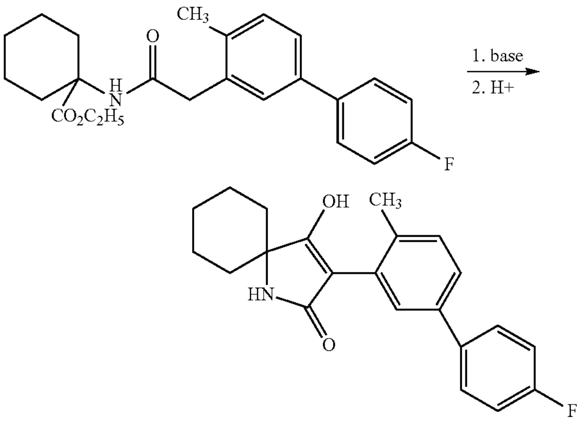

Using, according to process (B), ethyl O-[2-chloro-5-(4-fluorophenyl)phenylacetyl]-1-hydroxy-cyclopentanecarboxylate, the course of the process according to the invention can be represented by the reaction scheme below:

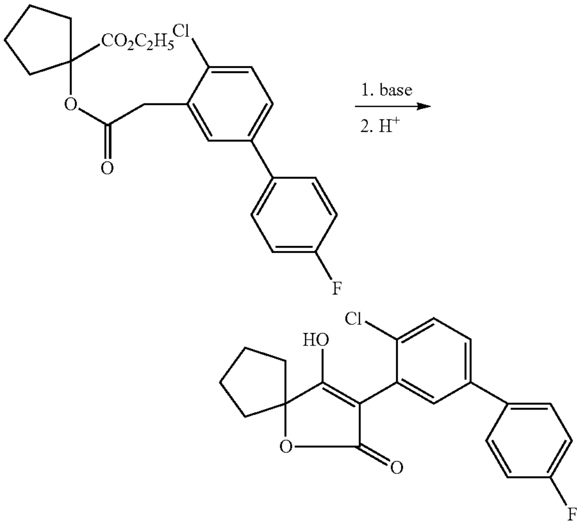

Using, according to process (C), 3-[(2,6-dimethyl-3-bromo)phenyl]-4,4-(pentamethylene)-pyrrolidine-2,4-dione and 4-fluorophenylboronic acid as starting materials, the course of the reaction can be represented by the scheme below:

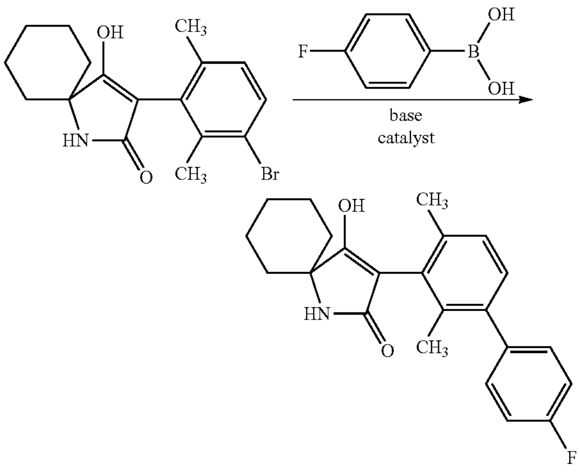

Using, according to process (Dα), 9-[(2-chloro-5-(4-fluorophenyl))phenyl]-4-oxa-7-azabicyclo[5.4.0]decane-8,10-dione and pivaloyl chloride as starting materials, the course of the process according to the invention can be represented by the reaction scheme below:

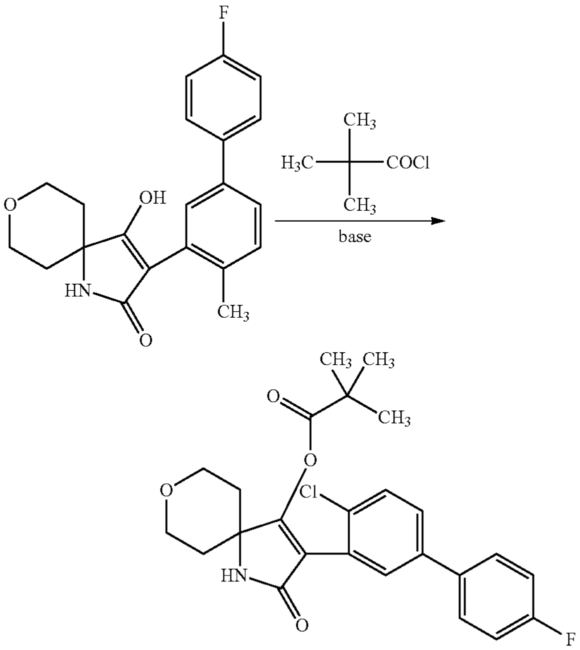

Using, according to process (D) (variant β), 3-[(6-methyl-3-(4-fluorophenyl))phenyl]-4-hydroxy-5,5-pentamethylene-$\Delta^3$-dihydrofuran-2-one and acetic anhydride as starting materials, the course of the process according to the invention can be represented by the reaction scheme below:

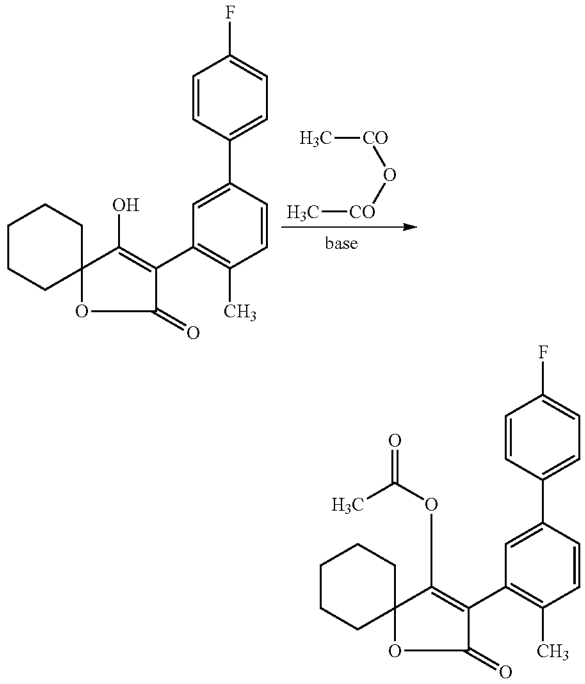

Using, according to process (E), 9-[2,6-dimethyl-3-(4-fluorophenyl)phenyl]-4-oxa-7-azabicyclo-(5.4.0)-decane-8,10-dione and ethyl chloroformate as starting materials, the course of the process according to the invention can be represented by the reaction scheme below:

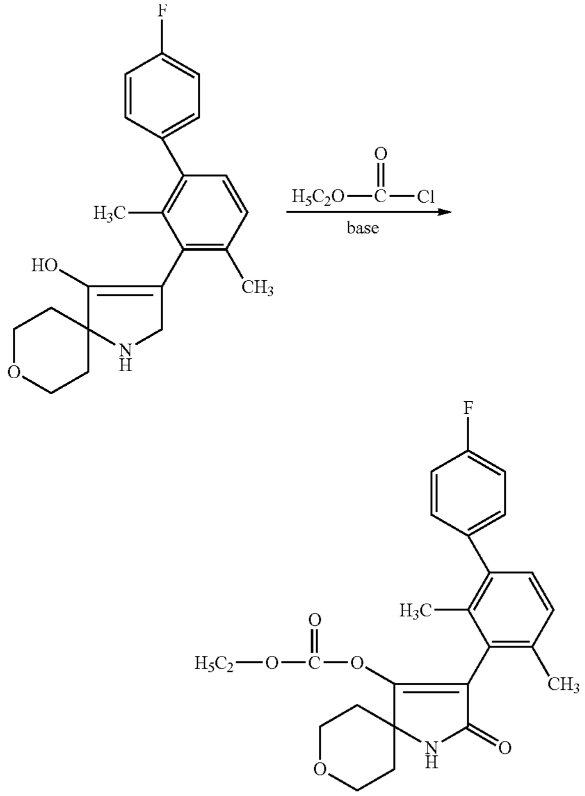

Using, according to process (F), 3-[2-chloro-5-(4-fluorophenyl)phenyl]-4-hydroxy-5,5-tetramethylene-$\Delta^3$-dihydrofuran-2-one and methyl chloromonothioformate as starting materials, the course of the reaction can be represented as follows:

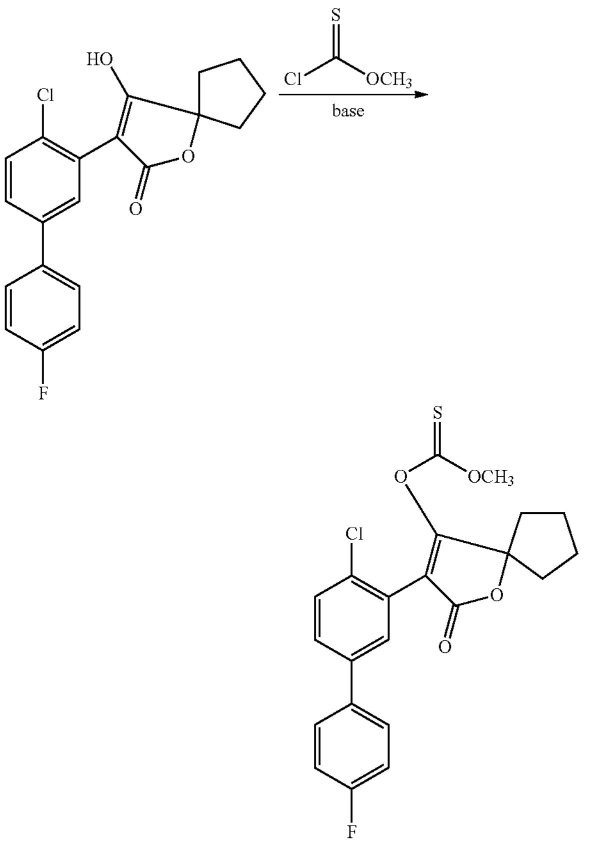

Using, according to process (G), 2-[(2,4,6-trimethyl-3-(4-fluorophenyl))phenyl]-5,5-penta-methylenepyrrolidine-2,4-dione and methanesulphonyl chloride as starting materials, the course of the reaction can be represented by the reaction scheme below:

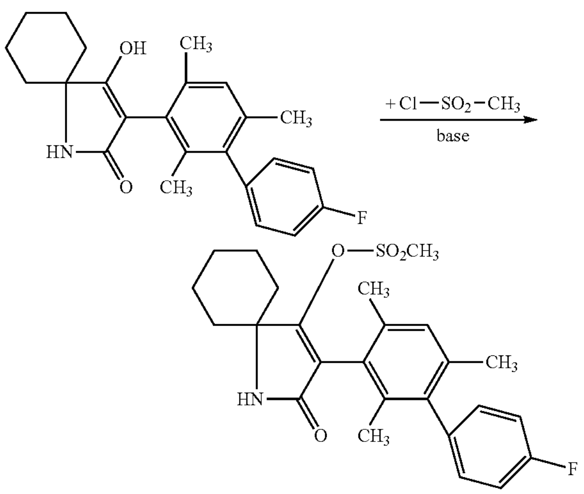

Using, according to process (H), 2-[(6-methyl-3-phenyl)phenyl]-4-hydroxy-5,5-tetramethylene-$\Delta^3$-dihydrofuran-2-one and 2,2,2-trifluoroethyl methanethiophosphonyl chloride as starting materials, the course of the reaction can be represented by the reaction scheme below:

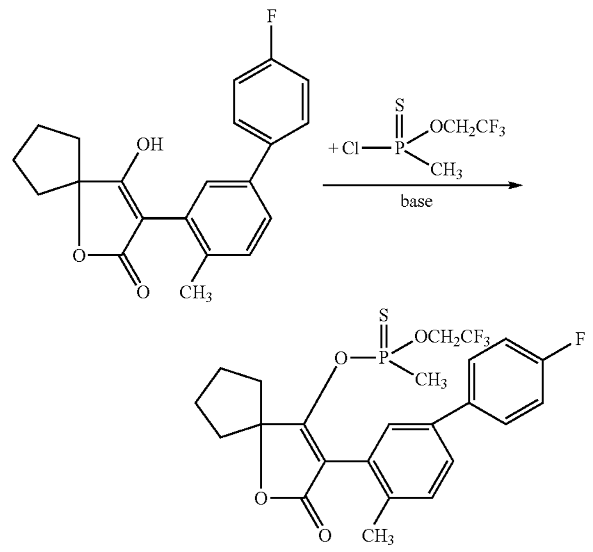

Using, according to process (I), 9-[2-methyl-5-(3,4-difluorophenyl)phenyl]-4-oxa-7-azabicyclo[5.4.0]-decane-8,10-dione and NaOH as components, the course of the process according to the invention can be represented by the reaction scheme below:

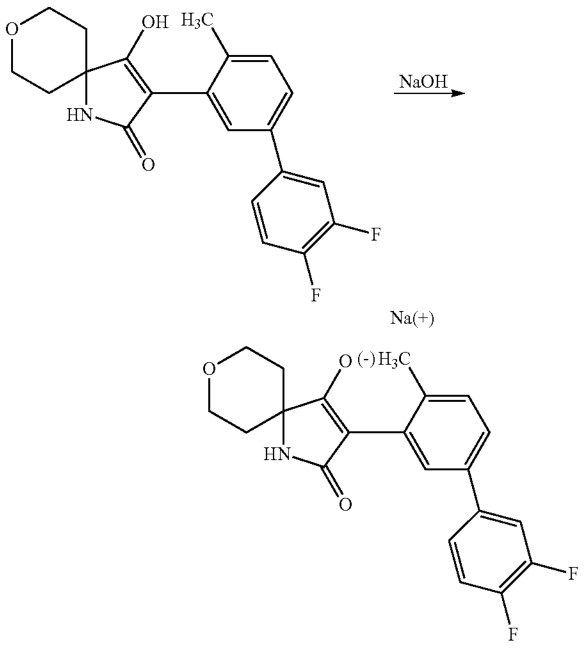

Using, according to process (J) (variant α), 3-[6-methyl-6-(4-fluorophenyl)phenyl]-4-hydroxy-5-tetramethylene-$\Delta^3$-dihydrofuran-2-one and ethyl isocyanate as starting materials, the course of the reaction can be represented by the reaction scheme below:

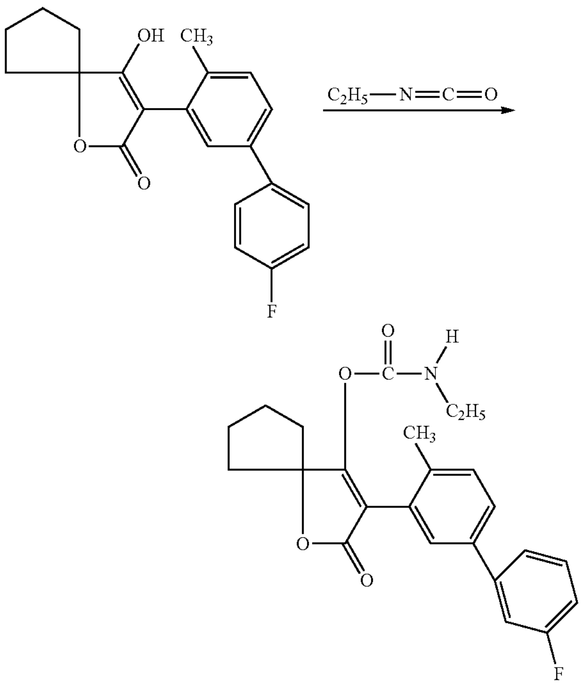

Using, according to process (J) (variant β), 3-[2-chloro-5-(4-fluorophenyl)phenyl]-5-pentamethylenepyrrolidine-2,4-dione and dimethylcarbamoyl chloride as starting materials, the course of the reaction can be represented by the scheme below:

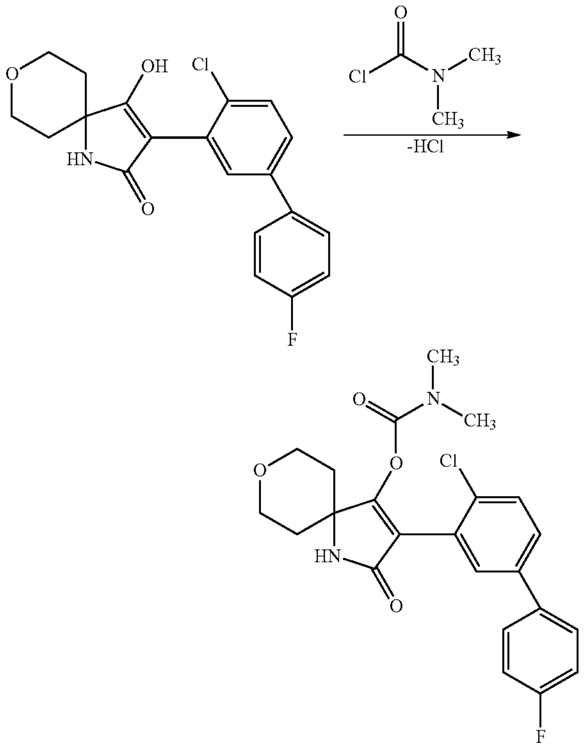

The compounds, required as starting materials in the process (A) according to the invention, of formula (II)

(II)

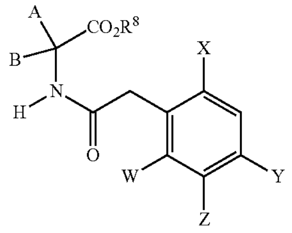

in which

A, B, W, X, Y, Z and $R^8$ have the meanings given above, are novel.

The acylamino acid esters of the formula (II) are obtained, for example, when amino acid derivatives of the formula (XV)

(XV)

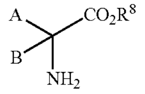

in which

A, B and $R^8$ have the meanings given above are acylated with substituted phenylacetic acid derivatives of the formula (XVI)

(XVI)

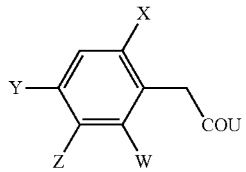

in which

W, X, Y and Z have the meanings given above and

U represents a leaving group introduced by reagents for activating carboxylic acids, such as carbonyldiimidazole, carbonyldiimides (such as, for example, dicyclohexylcarbodiimide), phosphorylating reagents (such as, for example $POCl_3$, BOP-Cl), halogenating agents, such as, for example, thionyl chloride, oxalyl chloride, phosgene or chloroformic esters (Chem. Reviews 52, 237-416 (1953); Bhattacharya, Indian J. Chem. 6, 341-5, 1968)

or when acylamino acids of the formula (XVII)

(XVII)

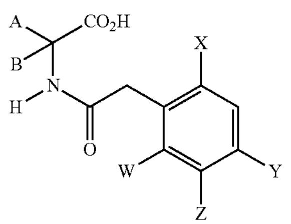

in which

A, B, W, X, Y and Z have the meanings given above, are esterified (Chem. Ind. (London) 1568 (1968)).

The compounds of the formula (XVII)

(XVII)

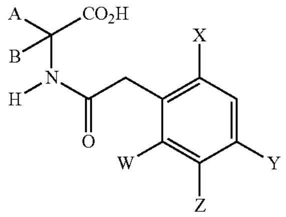

in which

A, B, W, X, Y and Z have the meanings given above are novel.

The compounds of the formula (XVII) are obtained when amino acids of the formula (XVIII)

(XVIII)

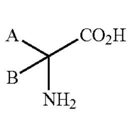

in which

A and B have the meanings given above are acylated with substituted phenylacetyl halides of the formula (XVI)

(XVI)

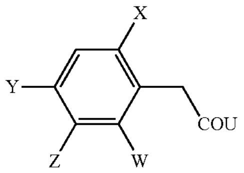

in which

U, W, X, Y and Z have the meanings given above for example according to Schotten-Baumann (Organikum, VEB Deutscher Verlag der Wissen-schaften, Berlin 1977, p. 505).

The compounds of the formula (XVI) are novel. They can be prepared by processes known in principle (see, for example, H. Henecka, Houben-Weyl, Methoden der Organischen Chemie [Methods of Organic Chemistry], Vol. 8, p. 467-469 (1952), or according to the patent applications cited at the outset).

The compounds of the formula (XVI) are obtained, for example, when substituted phenylacetic acids of the formula (XIX)

(XIX)

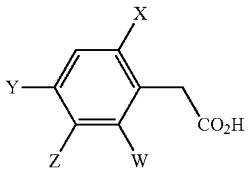

in which

W, X, Y and Z have the meaning given above are reacted with halogenating agents (for example thionyl chloride, thionyl bromide, oxalyl chloride, phosgene, phosphorus trichloride, phosphorus tribromide or phosphorus pentachloride) or phosphorylating agents (for example $POCl_3$, BOP-Cl), if appropriate in the presence of a diluent (for example optionally chlorinated aliphatic or aromatic hydrocarbons, such as toluene or methylene chloride), at temperatures of from −20° C. to 150° C., preferably from −10° C. to 100° C.

Some of the compounds of the formulae (XV) and (XVIII) are known from the patent applications cited at the outset, and/or they can be prepared by known processes (see, for example, Compagnon, Miocque Ann. Chim. (Paris) [14] 5, pp. 11-22, 23-27 (1970)).

The substituted cyclic aminocarboxylic acids of the formula (XVIIIa) in which A and B form a ring can generally be obtained by the Bucherer-Bergs synthesis or by the Strecker synthesis, where they are in each case obtained in different isomeric forms. Thus, the conditions of the Bucherer-Bergs synthesis yield predominantly the isomers (hereinbelow, for the sake of simplicity, referred to as β) in which the radicals R and the carboxyl group are in equatorial positions, whereas the conditions of the Strecker synthesis yield predominantly the isomers (hereinbelow, for the sake of simplicity, referred to as α) in which the amino group and the radicals R are in equatorial positions.

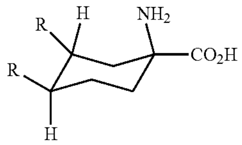

Bucherer-Bergs synthesis
(β isomer)

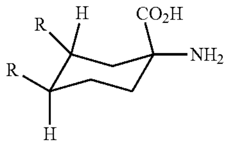

Strecker synthesis
(α isomer)

(L. Munday, J. Chem. Soc. 4372 (1961); J. T. Eward, C. Jitrangeri, Can. J. Chem. 53, 3339 (1975).

Furthermore, the starting materials, employed in the above process (A), of the formula (II)

(II)

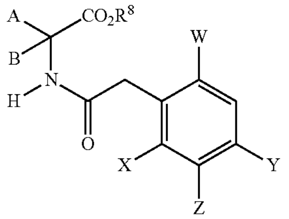

in which

A, B, W, X, Y, Z and $R^8$ have the meanings given above can be prepared by reacting amino nitriles of the formula (XX)

(XX)

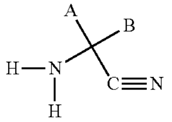

in which

A and B have the meanings given above with substituted phenylacetyl halides of the formula (XVI)

(XVI)

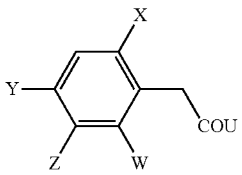

in which

W, X, Y and Z have the meanings given above, to give compounds of the formula (XXI)

(XXI)

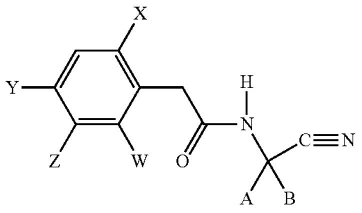

in which

A, B, W, X, Y and Z have the meanings given above, and then subjecting these to an acidic alcoholysis (EP-A-595130).

The compounds of the formula (XXI) are likewise novel.

The compounds, required as starting materials in the process (B) according to the invention, of the formula (III)

(III)

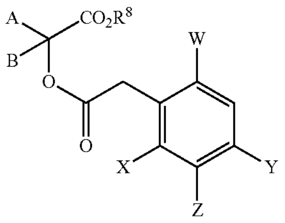

in which

A, B, W, X, Y, Z and $R^8$ have the meanings given above are novel.

They can be prepared by methods known in principle.

Thus, the compounds of the formula (III) are obtained, for example, when 2-hydroxycarboxylic esters of the formula (XXII)

(XXII)

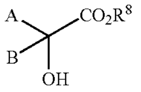

in which

A, B and $R^8$ have the meanings given above are acylated with substituted phenylacetyl halides of the formula (XVI)

(XVI)

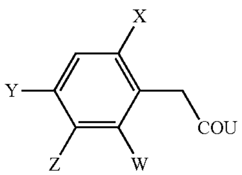

in which

W, X, Y, Z and U have the meanings given above (Chem. Reviews 52, 237-416 (1953) and the applications cited at the outset).

The compounds of the formula (XXII) are likewise known from the applications cited at the outset.

Some of the compounds of the formula (XIX) are known from WO 2005/016873, or they can be prepared by the processes described therein.

For example, the compounds of the formula (XIX), (XIX)

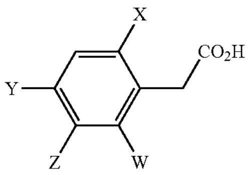

in which

W, X, Y and Z have the meanings given above are obtained

α) when compounds of the formula (XIX-a)

(XIX-a)

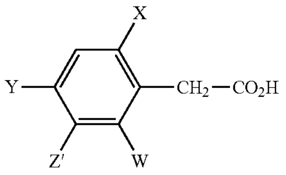

in which

X and Y have the meaning given above,

Z' represents chlorine, bromine or iodine, preferably bromine, are reacted with boronic acids or boronic acid derivatives of the formula (IV)

(IV)

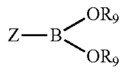

in which

Z and $R^9$ have the meaning given above in the presence of a diluent, a base and a catalyst (preferably a palladium salt or palladium complex, such as, for example, palladiumtetrakis(triphenylphosphine)) or β) when phenylacetic esters of the formula (XXIII)

(XXIII)

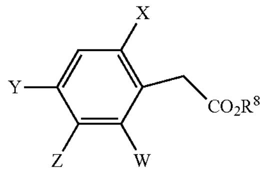

in which

W, X, Y, Z and $R^8$ have the meaning given above are hydrolysed in the presence of acids or bases, in the presence of a solvent under generally known standard conditions or γ) when phenylacetic acids of the formula (XIX-b)

(XIX-b)

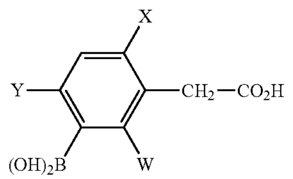

in which

W, X and Z have the meaning given above are reacted with halogen compounds of the formula (XXIV), Z-Hal (XXIV)

in which

Z has the meaning given above and

Hal represents chlorine, bromine or iodine, preferably bromine or iodine, in the presence of a solvent, a base and a catalyst (preferably a palladium salt or one of the palladium complexes mentioned above).

Some of the compounds of the formulae (IV) and (XXIV) are known, some are commercially available, or they can be prepared by processes known in principle. Some of the phenylacetic acids of the formula (XIX-a) are known from WO 97/01 535, WO 97/36 868 and WO 98/05 638, or they can be prepared by the processes described therein. Some of the compounds of the formula (XIX-b) are known from WO 05/016873, or they can be prepared by the processes described therein.

Some of the compounds of the formula (XXIII) are known from WO 2005/016873, or they can be prepared by the processes described therein.

The compounds of the formula (XXIII)

(XXIII)

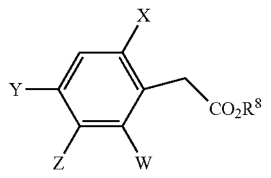

in which

W, X, Y, Z and $R^8$ have the meaning given above are obtained, for example, when phenylacetic esters of the formula (XXIII-a)

(XXIII-a)

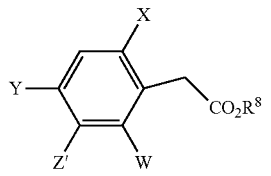

in which $R^8$, W, X, Y and Z' have the meaning give above are reacted with boronic acids or boronic acid derivatives of the formula (IV)

(IV)

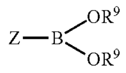

in which

Z and $R^9$ have the meaning given above in the presence of a solvent, a base and a catalyst (preferably a palladium salt or one of the palladium complexes mentioned above).

Some of the phenylacetic esters of the formula (XXIII-a) are known from the applications WO 97/01535, WO 97/36868 and WO 98/0563, or they can be prepared by the processes described therein.

Some of the compounds required as starting materials in the above process (C), of the formulae (I-1'-a) to (I-2'-g) in which A, B, W, X and Y have the meaning given above and Z' represents chlorine, bromine or iodine, preferably bromine, are known (WO 96/35 664, WO 97/02 243 and WO 98/05 638), or they can be prepared according to the processes described therein.

Some of the boronic acids and boronic acid derivatives of the formula (IV)

(IV)

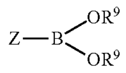

in which

Z and $R^9$ have the meaning given above are commercially available, or they can be prepared in a simple manner by generally known processes.

The acid halides of the formula (V), carboxylic anhydrides of the formula (VI), chloroformic esters or chloroformic thioesters of the formula (VII), chloromonothioformic esters or chlorodithioformic esters of the formula (VIII), sulphonyl chlorides of the formula (IX), phosphorus compounds of the formula (X) and metal hydroxides, metal alkoxides or amines of the formulae (XI) and (XII) and isocyanates of the formula (XIII) and carbamoyl chlorides of the formula (XIV) furthermore required as starting materials for carrying out the processes (D), (E), (F), (G), (H), (I) and (J) according to the invention are generally known compounds of organic or inorganic chemistry.

The process (A) is characterized in that compounds of the formula (II) in which A, B, W, X, Y, Z and $R^8$ have the meanings given above are subjected to an intramolecular condensation in the presence of a base.

Suitable diluents for use in the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Further, it is possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperatures may be varied within a relatively wide range. In general, the process is carried out at temperatures between 0° C. and 250° C., preferably between 50° C. and 150° C.

The process (A) according to the invention is generally carried out under atmospheric pressure.

When carrying out the process (A) according to the invention, the reaction components of the formula (II) and the deprotonating bases are generally employed in about doubly equimolar amounts. However, it is also possible to use a relatively large excess (up to 3 mol) of one component or the other.

The process (B) is characterized in that compounds of the formula (III) in which A, B, W, X, Y, Z and $R^8$ have the meanings given above are subjected to an intramolecular condensation in the presence of a diluent and in the presence of a base.

Suitable diluents which can be used for the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Further, it is possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (B) according to the invention, the reaction temperatures may be varied within a relatively wide range. In general, the process is carried out at temperatures between 0° C. and 250° C., preferably between 50° C. and 150° C.

The process (B) according to the invention is generally carried out under atmospheric pressure.

When carrying out the process (B) according to the invention, the reaction components of the formula (III) and the deprotonating bases are generally employed in about equimolar amounts. However, it is also possible to use a relatively large excess (up to 3 mol) of one component or the other.

Suitable catalysts for carrying out the process (C) according to the invention are palladium(0) complexes. Preference is given, for example, to tetrakis(triphenylphosphine)palladium. If appropriate, it is also possible to use palladium(II) salts, for example $PdCl_2$, $Pd(NO_3)_2$.

Suitable acid acceptors for carrying out the process (C) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, cesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (C) according to the invention are water, organic solvents and any mixtures thereof. Examples which may be mentioned are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether; water.

The reaction temperature in the process (C) according to the invention can be varied within a relatively wide range. In general, the process is carried out at temperatures between 0° C. and +140° C., preferably between 50° C. and +100° C.

When carrying out the process (C) according to the invention, the boronic acid derivatives of the formula (IV) in which Z has the meaning given above and the compounds of the formulae (I-1'-a) to (I-2'-g) in which A, B, W, X, Y and Z' have the meaning given above are employed in a molar ratio of from 1:1 to 3:1, preferably from 1:1 to 2:1. In general, from 0.005 to 0.5 mol, preferably from 0.01 mol to 0.1 mol, of catalyst are employed per mole of the compounds of the formulae (I-1-a) to (I-8-a). The base is generally employed in excess.

The process (D-α) is characterized in that compounds of the formulae (I-1-a) to (I-2-a) are reacted with carbonyl halides of the formula (V), if appropriate in the presence of a diluent and if appropriate in the presence of an acid binder.

Suitable diluents for use in the process (D-α) according to the invention are all solvents inert towards the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. If the acid halide is sufficiently stable to hydrolysis, the reaction can also be carried out in the presence of water.

Suitable acid binders for the reaction according to the process (D-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperatures in the process (D-α) according to the invention can be varied within a relatively wide range. In general, the process is carried out at temperatures between −20° C. and +150° C., preferably between 0° C. and 100° C.

When carrying out the process (D-α) according to the invention, the starting materials of the formulae (I-1-a) to (I-2-a) and the carbonyl halide of the formula (V) are generally each employed in approximately equivalent amounts. However, it is also possible to use a relatively large excess (up to 5 mol) of the carbonyl halide. Work-up is carried out by customary methods.

The process (D-β) is characterized in that compounds of the formulae (I-1-a) to (I-2-a) are reacted with carboxylic anhydrides of the formula (VI), if appropriate in the presence of a diluent and if appropriate in the presence of an acid binder.

Suitable diluents for use in the process (D-β) according to the invention are, preferably, the diluents which are also preferred when using acid halides. Besides, excess carboxylic anhydride may simultaneously act as diluent.

Suitable acid binders, which are added, if appropriate, for process (D-β) are, preferably, the acid binders which are also preferred when using acid halides.

The reaction temperatures in the process (D-β) according to the invention may be varied within a relatively wide range. In general, the process is carried out at temperatures between −20° C. and +150° C., preferably between 0° C. and 100° C.

When carrying out the process (D-β) according to the invention, the starting materials of the formulae (I-1-a) to (I-2-a) and the carboxylic anhydride of the formula (VI) are generally each employed in approximately equivalent amounts. However, it is also possible to use a relatively large excess (up to 5 mol) of carboxylic anhydride. Work-up is carried out by customary methods.

In general, diluent and excess carboxylic anhydride and the carboxylic acid formed are removed by distillation or by washing with an organic solvent or with water.

The process (E) is characterized in that compounds of the formulae (I-1-a) to (I-2-a) are reacted with chloroformic esters or chloroformic thioesters of the formula (VII), if appropriate in the presence of a diluent and if appropriate in the presence of an acid binder.

Suitable acid binders for the reaction according to the process (E) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (E) according to the invention are all solvents which are inert towards the chloroformic esters or chloroformic thioesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (E) according to the invention, the reaction temperatures can be varied within a relatively wide range. If the process is carried out in the presence of a diluent and an acid binder, the reaction temperatures are generally between −20° C. and +100° C., preferably between 0° C. and 50° C.

The process (E) according to the invention is generally carried out under atmospheric pressure.

When carrying out the process (E) according to the invention, the starting materials of the formulae (I-1-a) to (I-2-a) and the appropriate chloroformic ester or chloroformic thioester of the formula (VII) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (F) according to the invention is characterized in that compounds of the formulae (I-1-a) to (I-2-a) are reacted with compounds of the formula (VIII) in the presence of a diluent and, if appropriate, in the presence of an acid binder.

In preparation process (F), about 1 mol of chloromonothioformic ester or chlorodithioformic ester of the formula (VIII) is employed per mole of the starting material of the formulae (I-1-a) to (I-2-a) at from 0 to 120° C., preferably from 20 to 60° C.

Suitable diluents which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (I-1-a) to (I-2-a) is prepared by addition of strong deprotonating agents, such as, for example, sodium hydride or potassium tert-butoxide, the further addition of acid binders may be dispensed with.

If acid binders are used, these are customary inorganic or organic bases; sodium hydroxide, sodium carbonate, potassium carbonate, pyridine and triethylamine may be mentioned by way of example.

The reaction may be carried out at atmospheric pressure or under elevated pressure and is preferably carried out at atmospheric pressure. Work-up is carried out by customary methods.

The process (G) according to the invention is characterized in that compounds of the formulae (I-1-a) to (I-2-a) are reacted with sulphonyl chlorides of the formula (IX), if appropriate in the presence of a diluent and if appropriate in the presence of an acid binder.

In preparation process (G), about 1 mol of sulphonyl chloride of the formula (IX) is reacted per mole of the starting material of the formulae (I-1-a) to (I-2-a) at from −20 to 150° C., preferably from 20 to 70° C.

Suitable diluents which are added, if appropriate, are all inert polar organic solvents, such as ethers, amides, nitriles, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (I-1-a) to (I-2-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine and triethylamine.

The reaction may be carried out at atmospheric pressure or under elevated pressure and is preferably carried out at atmospheric pressure. Work-up is carried out by customary methods.

The process (H) according to the invention is characterized in that compounds of the formulae (I-1-a) to (I-2-a) are reacted with phosphorus compounds of the formula (X), if appropriate in the presence of a diluent and if appropriate in the presence of an acid binder.

In preparation process (H), to obtain compounds of the formulae (I-1-e) to (I-2-e), from 1 to 2, preferably from 1 to 1.3, mol of the phosphorus compound of the formula (X) are reacted per mole of the compounds (I-1-a) to (I-2-a), at temperatures between −40° C. and 150° C., preferably between −10 and 110° C.

Suitable diluents which are added, if appropriate, are all inert polar organic solvents, such as ethers, amides, nitriles, alcohols, sulphides, sulphones, sulphoxides, etc.

Preference is given to using acetonitrile, dimethyl sulphoxide, tetrahydrofuran, dimethyl-formamide, methylene chloride.

Suitable acid binders which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The resulting end products are preferably purified by crystallization, chromatographic purification or "incipient distillation", i.e. removal of the volatile components under reduced pressure.

The process (I) is characterized in that compounds of the formulae (I-1-a) to (I-2-a) are reacted with metal hydroxides or metal alkoxides of the formula (XI) or amines of the formula (XII), if appropriate in the presence of a diluent.

Suitable diluents for use in the process (I) according to the invention are, preferably, ethers, such as tetrahydrofuran, dioxane, diethyl ether, or else alcohols, such as methanol, ethanol, isopropanol, and also water.

The process (I) according to the invention is generally carried out under atmospheric pressure.

The reaction temperatures are generally between −20° C. and 100° C., preferably between 0° C. and 50° C.

The process (J) according to the invention is characterized in that compounds of the formulae (I-1-a) to (I-2-a) are reacted with (J-α) compounds of the formula (XIII), if appropriate in the presence of a diluent and if appropriate in the presence of a catalyst, or (J-β) with compounds of the formula (XIV), if appropriate in the presence of a diluent and if appropriate in the presence of an acid binder.

In preparation process (J-α), about 1 mol of isocyanate of the formula (XIII) is reacted per mole of starting material of the formulae (I-1-a) to (I-2-a), at from 0 to 100° C., preferably from 20 to 50° C.

Suitable diluents which are added, if appropriate, are all inert organic solvents, such as ethers, amides, nitriles, sulphones or sulphoxides.

If appropriate, catalysts may be added to accelerate the reaction. Suitable for use as catalysts are, very advantageously, organotin compounds, such as, for example, dibutyltin dilaurate. The reaction is preferably carried out at atmospheric pressure.

In preparation process (J-β), about 1 mol of carbamoyl chloride of the formula (XIV) is reacted per mole of starting compound of the formulae (I-1-a) to (I-2-a), at from −20 to 150° C., preferably at from 0 to 70° C.

Suitable diluents which are added, if appropriate, are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compounds (I-1-a) to (I-2-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following compounds:

Fungicides:

Inhibitors of Nucleic Acid Synthesis
- benalaxyl, benalaxyl-M, bupirimate, chiralaxyl, clozylacon, dimethirimol, ethirimol, furalaxyl, hymexazole, metalaxyl, metalaxyl-M, ofurace, oxadixyl, oxolinic acid Inhibitors of Mitosis and Cell Division
- benomyl, carbendazim, diethofencarb, fuberidazole, pencycuron, thiabendazole, thiophanate-methyl, zoxamide Inhibitors of Respiratory Chain Complex I
- diflumetorim Inhibitors of Respiratory Chain Complex II
- boscalid, carboxin, fenfuram, flutolanil, furametpyr, mepronil, oxycarboxin, penthiopyrad, thifluzamide Inhibitors of Respiratory Chain Complex III
- azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin Decouplers
- dinocap, fluazinam Inhibitors of ATP Production
- fentin acetate, fentin chloride, fentin hydroxide, silthiofam Inhibitors of Amino Acid Biosynthesis and Protein Biosynthesis
- andoprim, blasticidin-S, cyprodinil, kasugamycin, kasugamycin hydrochloride hydrate, mepanipyrim, pyrimethanil Inhibitors of Signal Transduction
- fenpiclonil, fludioxonil, quinoxyfen Inhibitors of Lipid and Membrane Synthesis
- chlozolinate, iprodione, procymidone, vinclozolin
- ampropylfos, potassium-ampropylfos, edifenphos, iprobenfos (IBP), isoprothiolane, pyrazophos
- tolclofos-methyl, biphenyl
- iodocarb, propamocarb, propamocarb hydrochloride Inhibitors of Ergosterol Biosynthesis
- fenhexamid,
- azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidole, nuarimol, pyrifenox, triforine, pefurazoate, prochloraz, triflumizole, viniconazole,
- aldimorph, dodemorph, dodemorph acetate, fenpropimorph, tridemorph, fenpropidin, spiroxamine,
- naftifine, pyributicarb, terbinafine Inhibitors of Cell Wall Synthesis
- benthiavalicarb, bialaphos, dimethomorph, flumorph, iprovalicarb, polyoxins, polyoxorim, validamycin A Inhibitors of Melanin Biosynthesis
- capropamid, diclocymet, fenoxanil, phthalid, pyroquilon, tricyclazole Resistance Inductors
- acibenzolar-S-methyl, probenazole, tiadinil Multisite
- captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram Unknown Mechanism
- amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulphamide, fluopicolide, fluoroimide, hexachlorobenzene, 8-hydroxy-quinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methylbenzenesulphonamide, 2-amino-4-methyl-N-phenyl-5-thiazolecarboxamide, 2-chloro-N-(2,3-dihydro-1,1,3-trimethyl-1H-inden-4-yl)-3-pyridine-carboxamide, 3-[5-(4-chlorophenyl)-2,3-dimethylisoxazolidin-3-yl]pyridine, cis-1-(4-chloro-phenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxy-phenyl)imino]methyl]thio]methyl].alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulphonyl)amino]butanamide, 5-chloro-7-(4-methylpiperidin-1-yl)-6-(2,4,6-trifluorophenyl)[1,2,4]-triazolo[1,5-a]pyrimidine, 5-chloro-6-(2,4,6-trifluorophenyl)-N-[(1R)-1,2,2-trimethylpropyl]-[1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloro-nicotinamide, 2-butoxy-6-iodo-3-propylbenzopyranon-4-one, N-{(Z)-[(cyclopropylmethoxy)-imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3 (1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoro-methyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methyl-acetamide Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

Acetylcholine Esterase (AChE) Inhibitors carbamates, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate organophosphates, for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers pyrethroids, for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)

DDT oxadiazines, for example indoxacarb semicarbazones, for example metaflumizone (BAS3201)

Acetylcholine Receptor Agonists/Antagonists chloronicotinyls, for example acetamiprid, clothianidin, dinotefuran, imidacloprid, nitenpyram, nithiazine, thiacloprid, thiamethoxam nicotine, bensultap, cartap Acetylcholine Receptor Modulators spinosyns, for example spinosad GABA-Controlled Chloride Channel Antagonists organochlorines, for example camphechlor, chlordane, endosulphan, gamma-HCH, HCH, heptachlor, lindane, methoxychlor fiprols,
for example acetoprole, ethiprole, fipronil, pyrafluprole, pyriprole, vaniliprole
Chloride Channel Activators
mectins,
for example abamectin, emamectin, emamectin-benzoate, ivermectin, lepimectin, milbemycin
Juvenile Hormone Mimetics,
for example diofenolan, epofenonane, fenoxycarb, hydroprene, kinoprene, methoprene, pyriproxifen, triprene
Ecdysone Agonists/Disruptors
diacylhydrazines,
for example chromafenozide, halofenozide, methoxyfenozide, tebufenozide
Chitin Biosynthesis Inhibitors
benzoylureas,
for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
buprofezin
cyromazine
Oxidative Phosphorylation Inhibitors, ATP Disruptors
diafenthiuron
organotin compounds,
for example azocyclotin, cyhexatin, fenbutatin-oxide
Oxidative Phosphorylation Decouplers Acting by Interrupting the H-Proton Gradient
pyrroles,
for example chlorfenapyr
dinitrophenols,
for example binapacyrl, dinobuton, dinocap, DNOC
Site-I Electron Transport Inhibitors
METI's,
for example fenazaquin, fenpyroximate, pyrimidifen, pyridaben, tebufenpyrad, tolfenpyrad
hydramethylnon
dicofol
Site-II Electron Transport Inhibitors
rotenone
Site-III Electron Transport Inhibitors
acequinocyl, fluacrypyrim
Microbial Disruptors of the Insect Gut Membrane
*Bacillus thuringiensis* strains
Lipid Synthesis Inhibitors
tetronic acids,
for example spirodiclofen, spiromesifen
tetramic acids,
for example spirotetramate
Carboxamides,
for example flonicamid
Octopaminergic Agonists,
for example amitraz
Inhibitors of Magnesium-Stimulated ATPase,
propargite
Ryanodine Receptor Agonists,
a) benzodicarboxamides,
for example flubendiamide
b) anthranilamides, for example
rynaxypyr (3-bromo-N-{4-chloro-2-methyl-6-[(methylamino)carbonyl]phenyl}-1-(3-chloropyridin-2-yl)-1H-pyrazole-5-carboxamide)
Nereistoxin Analogues,
for example thiocyclam hydrogen oxalate, thiosultap-sodium
Biologicals, Hormones or Pheromones
azadirachtin, *Bacillus* spec., *Beauveria* spec., *codlemone, Metarrhizium* spec., *Paecilomyces* spec., thuringiensin, *Verticillium* spec.
Active Compounds with Unknown or Unspecific Mechanisms of Action
fumigants,
for example aluminium phosphide, methyl bromide, sulphuryl fluoride
antifeedants,
for example cryolite, flonicamid, pymetrozine
mite growth inhibitors,
for example clofentezine, etoxazole, hexythiazox
amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulphluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particular advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as “Bt plants”). Traits that are also particularly emphasized are the increased defence of plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of plants to certain herbicidally active compounds, for example imidazolinones, sulphonylureas, glyphosate or phosphinotricin (for example the “PAT” gene). The genes which impart the desired traits in question can also be present in combination with one another in the transgenic plants. Examples of “Bt plants” which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reductions in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100- to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds according to the invention can be used for example in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds/active compound combinations according to the invention is in no way restricted to these genera, but extends in the same manner to other plants.

Depending on the concentration, the active compounds/active compound combinations according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The active compounds of the formula (I)/active compound combinations according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds/active compound combinations according to the invention can also be employed for controlling animal pests and fungal or bacterial plant diseases. If appropriate, they can also be used as intermediates or precursors for the synthesis of other active compounds.

The active compounds/active compound combinations can be converted into the customary formulations, such as solutions, emulsions, wettable powders, suspensions, powders, dusts, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkyl-naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalo-cyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds/active compound combinations according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarbazone, amidochlor, amidosulphuron, aminopyralid, anilofos, asulam, atrazine, azafenidin, azimsulphuron, beflubutamid, benazolin (-ethyl), benfuresate, bensulphuron (-methyl), bentazone, bencarbazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulphuron, chlortoluron, cinidon (-ethyl), cinmethylin, cinosulphuron, clefoxydim, clethodim, clodinafop (-propargyl), clomazone, clomeprop, clopyralid, clopyrasulphuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulphuron (-methyl), ethofumesate, ethoxyfen, ethoxysulphuron, etobenzanid, fenoxaprop (—P-ethyl), fentrazamide, flamprop (-isopropyl, -isopropyl-L, -methyl), flazasulphuron, florasulam, fluazifop (—P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulphuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulphuron, glufosinate (-ammonium), glyphosate (-isopropylammonium), halosafen, haloxyfop (-ethoxyethyl, —P-methyl), hexazinone, HOK-201, imazamethabenz (-methyl), imazamethapyr, imazamox, imazapic, imazapyr, imazaquin, imazethapyr, imazosulphuron, iodosulphuron (-methyl, -sodium), ioxynil, isopropalin, isoproturon, isouron, isoxaben, isoxachlortole, isoxaflutole, isoxapyrifop, KIH 485, lactofen, lenacil, linuron, MCPA, mecoprop, mefenacet, mesosulphurone, mesotrione, metamifop, metamitron, metazachlor, methabenzthiazuron, metobenzuron, metobromuron, (alpha-) metolachlor, metosulam, metoxuron, metribuzin, metsulphuron (-methyl), molinate, monolinuron, naproanilide, napropamide, neburon, nicosulphuron, norflurazon, orbencarb, orthosulfamuron, oryzalin, oxadiargyl, oxadiazon, oxasulphuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulphuron (-methyl), profluazol, prometryn, propachlor, propanil, propaquizafop, propisochlor, propoxycarbazone (-sodium), propyzamide, prosulfocarb, prosulphuron, pyraflufen (-ethyl), pyrasulfotole, pyrazogyl, pyrazolate, pyrazosulphuron (-ethyl), pyrazoxyfen, pyribenzoxim, pyributicarb, pyridate, pyridatol, pyriftalide, pyriminobac (-methyl), pyrimisulfan, pyrithiobac (-sodium), quinchlorac, quinmerac, quinoclamine, quizalofop (—P-ethyl, —P-tefuryl), rimsulphuron, sethoxydim, simazine, simetryn, sulcotrione, sulfentrazone, sulfometuron (-methyl), sulfosate, sulfosulphuron, tebutam, tebuthiuron, tembotrione, tepraloxydim, terbuthylazine, terbutryn, thenylchlor, thiafluamide, thiazopyr, thidiazimin, thifensulphuron (-methyl), thiobencarb, tiocarbazil, topramezone, tralkoxydim, triallate, triasulphuron, tribenuron (-methyl), triclopyr, tridiphane, trifluralin, trifloxysulphuron, triflusulphuron (-methyl), tritosulphuron and

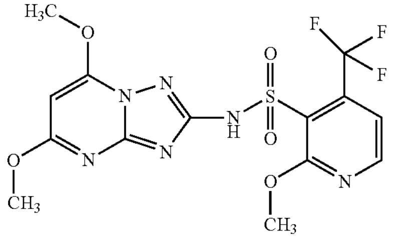

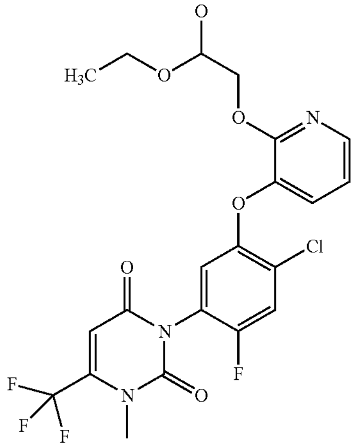

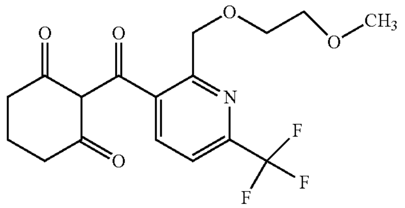

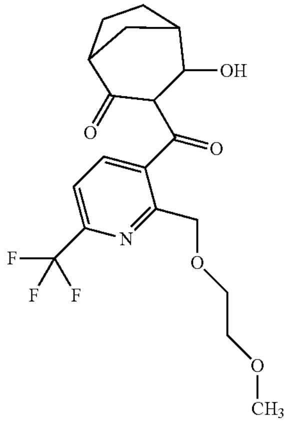

A mixture with other known active compounds, such as fungicides, insectides, acaricides, nematicides, bird repellents, plant nutrients and soil conditioners, is also possible.

The active compounds or active compound combinations can be applied as such, in the form of their formulations or the use forms prepared therefrom by further dilution, such as ready-to-use solutions, suspensions, emulsions, powders, pastes and granules. They are applied in the customary manner, for example by watering, spraying, atomizing, spreading.

The active compounds or active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation “Rako Binol”), or ammonium salts, such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. Application is in the customary manner, for example by watering, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can, if appropriate, also be used as herbicides, for influencing plant growth, and also for controlling animal pests. If appropriate, they can also be used as intermediates and precursors for the synthesis of further active compounds.

The term “active compounds” also includes the active compound combinations mentioned.

The preparation and the use of the active compounds according to the invention is illustrated by the examples below.

PREPARATION EXAMPLES

Example I-1-a-1

Process A

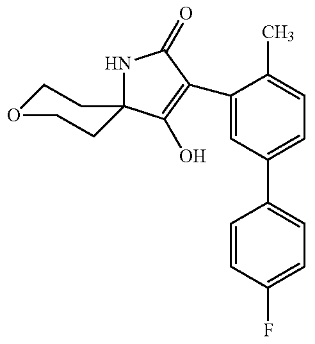 [SMILES: Cc1ccc(-c2ccc(F)cc2)cc1C1=C(O)C2(CCOCC2)NC1=O]

At 80° C., 2.4 g of the compound according to Ex. II-1 in 6 ml of N,N-dimethylacetamide are added dropwise to 1.83 g (15.5 mmol) of potassium tert-butoxide in 6 ml of N,N-dimethylacetamide, and the mixture is stirred at 80° C. for one hour.

A sample is analysed by thin-layer chromatography, and the reaction mixture is then added to 80 ml of ice-water and, at 0-10° C., adjusted to pH 2 using 1N hydrochloric acid. The precipitate is filtered off with suction, washed and dried.

Crude yield: 2.35 g of a beige powder

Following separation by preparative HPLC, the product is obtained in a yield of: 173 mg (7.7% of theory), m.p. 94° C.

Example I-1-a-2

Process A

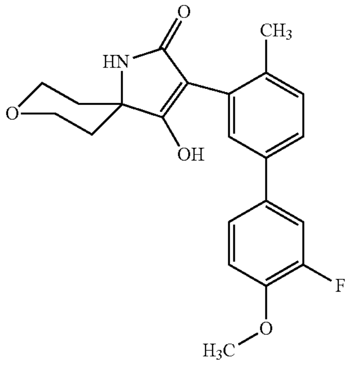 [SMILES: COc1ccc(-c2ccc(C)c(C3=C(O)C4(CCOCC4)NC3=O)c2)cc1F]

At 60° C., 1.95 g (4.7 mmol) of the compound according to Ex. II-2 in 4.0 ml of N,N-dimethylacetamide are added dropwise to 1.3 g (10.5 mmol) of potassium tert-butoxide in 4 ml of N,N-dimethylacetamide, and the mixture is stirred at 60° C. for one hour.

A sample is analysed by thin-layer chromatography, and the reaction mixture is then added to 80 ml of ice-water and, at 0-10° C., adjusted to pH 2 using 1N hydrochloric acid, and the precipitate is filtered off with suction, washed and dried. Purification was carried out by column chromatography on silica gel using the mobile phase ethyl acetate.

Yield: 0.92 g (48.8% of theory), m.p. 177° C.

Example I-1-a-24

Process C

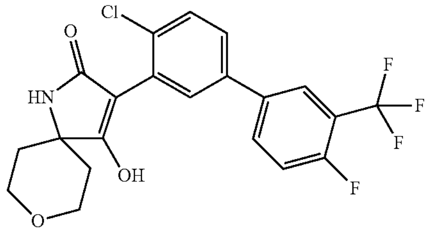 [SMILES: O=C1NC2(CCOCC2)C(O)=C1c1cc(-c2ccc(F)c(C(F)(F)F)c2)ccc1Cl]

0.717 g of the compound according to Ex. I-1'-a-1, 0.448 g of 4-fluoro-3-trifluoromethylphenylboronic acid and 0.8 g of sodium carbonate are initially charged in 15 ml of water, 0.05 g of palladium(II) nitrate dihydrate are added and the mixture is stirred at 144° C. in a microwave oven for 20 min. After cooling, the mixture is acidified with dilute hydrochloric acid and filtered off with suction.

This is followed by an MPLC separation on silica gel using a mobile phase gradient of cyclohexane+50-80% ethyl acetate.

Yield: 0.31 g (34% of theory), m.p. 257° C.

The following compounds of the formula (I-1-a) are obtained analogously to Examples (I-1-a-1) and (I-1-a-2) and in accordance with the general statements on the preparation:

(I-1-a)

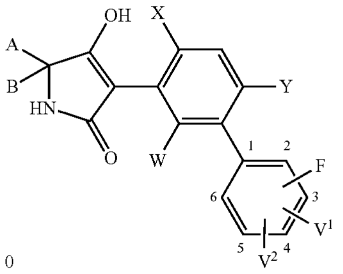

| Ex. No. | W | X | Y | F | $V^1$ | $V^2$ | A | B | M.p. ° C. | Isomer |
|---|---|---|---|---|---|---|---|---|---|---|
| I-1-a-3 | H | $CH_3$ | H | 4 | 3-F | H | $-(CH_2)_2-O-(CH_2)_2-$ | | 241 | — |
| I-1-a-4 | $CH_3$ | $CH_3$ | H | 4 | H | H | $-(CH_2)_2-O-(CH_2)_2-$ | | 167 | — |
| I-1-a-5 | $CH_3$ | $CH_3$ | H | 4 | 3-F | H | $-(CH_2)_2-O-(CH_2)_2-$ | | 164 | — |
| I-1-a-6 | H | $CH_3$ | H | 3 | 4-Cl | H | $-(CH_2)_2-O-(CH_2)_2-$ | | 258 | — |
| I-1-a-7 | H | $CH_3$ | H | 4 | H | H | $-CH_2-CHOC_2H_5-(CH_2)_3-$ | | 102 | β |
| I-1-a-8 | H | $CH_3$ | H | 4 | H | H | 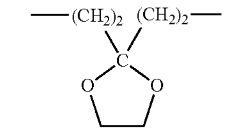 | | 290 | — |
| I-1-a-9 | $CH_3$ | $CH_3$ | H | 4 | H | H | 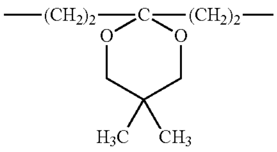 | | 299 | — |
| I-1-a-10 | $CH_3$ | $CH_3$ | H | 4 | H | H | $-CH_2-O-(CH_2)_3-$ | | 284 | — |

-continued (I-1-a)

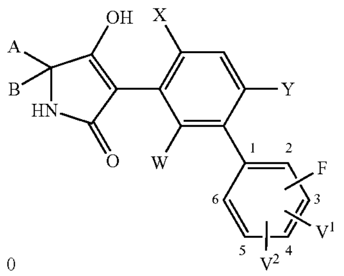

0

| Ex. No. | W | X | Y | F | $V^1$ | $V^2$ | A | B | M.p. ° C. | Isomer |
|---|---|---|---|---|---|---|---|---|---|---|
| I-1-a-11 | H | $CH_3$ | H | 4 | H | H | $—CH_2—CHCH_3—O—(CH_2)_2—$ | | * 1.11-1.13 (2d, 3H, $CHCH_3$ 2.19 (d, 3H, Ar—$CH_3$ 3.72-4.06 (3m, 3H, O—$CH_2$, O—CH—$CH_3$) 7.61-7.66 (m, 2H, Ar—H) | β |
| I-1-a-12 | $CH_3$ | $CH_3$ | H | 4 | H | H | $—CH_2—CHCH_3—O—(CH_2)_2—$ | | 168 | β |
| I-1-a-13 | H | Cl | H | 4 | H | H | $—(CH_2)_2—O—(CH_2)_2—$ | | 279 | — |
| I-1-a-14 | H | $CH_3$ | H | 4 | 3-$CH_3$ | H | $—(CH_2)_2—O—(CH_2)_2—$ | | 160 | — |
| I-1-a-15 | $CH_3$ | $CH_3$ | H | 4 | 3-$CH_3$ | H | $—(CH_2)_2—O—(CH_2)_2—$ | | 163 | — |
| I-1-a-16 | H | $CH_3$ | H | 4 | 3-Cl | H | $—(CH_2)_2—O—(CH_2)_2—$ | | 200 | — |
| I-1-a-17 | H | Cl | H | 4 | 3-Cl | H | $—(CH_2)_2—O—(CH_2)_2—$ | | 160 | — |
| I-1-a-18 | H | $CH_3$ | H | 4 | 3-$OCH_3$ | H | $—(CH_2)_2—O—(CH_2)_2—$ | | 141 | — |
| I-1-a-19 | H | Cl | H | 4 | 3-$CH_3$ | H | $—(CH_2)_2—O—(CH_2)_2—$ | | 254 | — |
| I-1-a-20 | $CH_3$ | $CH_3$ | H | 4 | 3-Cl | H | $—(CH_2)_2—O—(CH_2)_2—$ | | 298 | — |
| I-1-a-21 | H | Cl | H | 4 | 3-F | H | $—(CH_2)_2—O—(CH_2)_2—$ | | 273 | — |
| I-1-a-22 | H | $CH_3$ | H | 4 | 3-$CF_3$ | H | $—(CH_2)_2—O—(CH_2)_2—$ | | 210 | — |
| I-1-a-23 | $CH_3$ | $CH_3$ | H | 4 | 3-$CF_3$ | H | $—(CH_2)_2—O—(CH_2)_2—$ | | 262 | — |
| I-1-a-24 | H | Cl | H | 4 | 3-$CF_3$ | H | $—(CH_2)_2—O—(CH_2)_2—$ | | 257 | — |
| I-1-a-25 | $CH_3$ | $CH_3$ | H | 4 | 3-F | 5-F | $—(CH_2)_2—O—(CH_2)_2—$ | | 267 | — |
| I-1-a-26 | $CH_3$ | $CH_3$ | H | 4 | 2-$CH_3$ | H | $—(CH_2)_2—O—(CH_2)_2—$ | | * 1.25-1.34 (m, 2H, $CH_2$); 2.14 (s, 3H, Ar—$CH_3$); 3.67-3.75 (m, 2H—O—$CH_2$); 6.88-6.9 (m, 1H—Ar—H) | — |
| I-1-a-27 | H | Cl | H | 4 | 2-$CH_3$ | H | $—(CH_2)_2—O—(CH_2)_2—$ | | * 1.25-1.32 (m, 2H, $OCH_2$); 2.28 (s, 3H, Ar—$CH_3$); 3.88-3.87 (m, 2H, O—$CH_2$); 7.48 (d, 1H, Ar—H) | — |
| I-1-a-28 | H | $CH_3$ | H | 4 | 3-F | 5-F | $—(CH_2)_2—O—(CH_2)_2—$ | | * 2.20 (s, 3H, Ar—$CH_3$); 3.68-3.75 (m, 2H, O—$CH_2$); 3.85-3.89 (m, 2H, O—$CH_2$); 7.29-7.31 (d, 1H, Ar—H) | — |
| I-1-a-29 | H | $CH_3$ | H | 4 | 2-F | H | $—(CH_2)_2—O—(CH_2)_2—$ | | * 1.25-1.32 (m, 2H, $CH_2$); 2.21 (s, 3H, Ar—$CH_3$); 3.84-3.88 (m, 2H—$OCH_2$); 7.49-7.55 (m, 1H, Ar—H) | — |
| I-1-a-30 | H | Cl | H | 4 | 3-F | 5-F | $—(CH_2)_2—O—(CH_2)_2—$ | | 300 | — |
| I-1-a-31 | H | $CH_3$ | H | 4 | 2-$CH_3$ | H | $—(CH_2)_2—O—(CH_2)_2—$ | | * 1.25-1.31 (m, 2H, $CH_2$); 2.21, 2.26 (2s, 3H each, Ar—$CH_3$); 3.84-3.87 (m, 2H, O—$CH_2$); 7.00-7.05 (m, 2H, Ar—H) | — |
| I-1-a-32 | H | Cl | H | 4 | 3-$OCH_3$ | H | $—(CH_2)_2—O—(CH_2)_2—$ | | 226 | — |
| I-1-a-33 | $CH_3$ | $CH_3$ | $CH_3$ | 4 | H | H | $—(CH_2)_2—O—(CH_2)_2—$ | | 298 | — |
| I-1-a-34 | $CH_3$ | $CH_3$ | H | 4 | 2-F | H | $—(CH_2)_2—O—(CH_2)_2—$ | | 215 | — |
| I-1-a-35 | H | Cl | H | 4 | 2-F | H | $—(CH_2)_2—O—(CH_2)_2—$ | | * 1.25-1.33 (m, 2H, $CH_2$); 3.66-3.73 (m, 2H, O—$CH_2$); 3.84-3.87 (m, 2H, $OCH_2$); 7.40-7.41 (m, 1H, Ar—H) | — |
| I-1-a-36 | H | $CH_3$ | H | 3 | H | H | $—(CH_2)_2—O—(CH_2)_2—$ | | 138 | — |
| I-1-a-37 | $CH_3$ | $CH_3$ | H | 3 | H | H | $—(CH_2)_2—O—(CH_2)_2—$ | | 147 | — |
| I-1-a-38 | H | $CH_3$ | H | 3 | 5-F | H | $—(CH_2)_2—O—(CH_2)_2—$ | | 230 | — |
| I-1-a-39 | $CH_3$ | $CH_3$ | H | 3 | 5-F | H | $—(CH_2)_2—O—(CH_2)_2—$ | | 163 | — |
| I-1-a-40 | H | Cl | H | 2 | 5-F | H | $—(CH_2)_2—O—(CH_2)_2—$ | | | — |
| I-1-a-41 | H | Cl | H | 3 | 5-F | H | $—(CH_2)_2—O—(CH_2)_2—$ | | 276 | — |
| I-1-a-42 | H | $CH_3$ | H | 2 | 5-F | H | $—(CH_2)_2—O—(CH_2)_2—$ | | * 1.25-1.33 (m, 2H, —$CH_2$)—; 2.21 (s, 3H, Ar—$CH_3$); 3.68-3.74 (m, 2H, $OCH_2$); 7.15-7.21 (m, 1H, Ar—H) | — |
| I-1-a-43 | H | $CH_3$ | H | 3 | 4-$CH_3$ | H | $—(CH_2)_2—O—(CH_2)_2—$ | | 156 | — |
| I-1-a-44 | $CH_3$ | $CH_3$ | H | 3 | 4-$CH_3$ | H | $—(CH_2)_2—O—(CH_2)_2—$ | | 191 | — |
| I-1-a-45 | H | Cl | H | 3 | 4-$CH_3$ | H | $—(CH_2)_2—O—(CH_2)_2—$ | | 215 | — |
| I-1-a-46 | H | $CH_3$ | H | 4 | H | H | $—CH_2—O—(CH_2)_3—$ | | 259 | — |
| I-1-a-47 | H | Cl | H | 4 | H | H | $—CH_2—O—(CH_2)_3—$ | | 272 | — |
| I-1-a-48 | $CH_3$ | $CH_3$ | H | 4 | H | H | $—CH_2—CHOCH_3—(CH_2)_3—$ | | 263 | cis |

-continued (I-1-a)

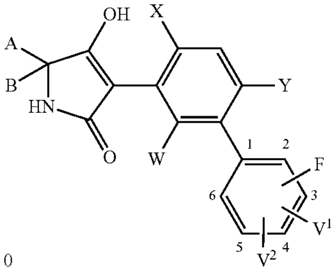

0

| Ex. No. | W | X | Y | F | $V^1$ | $V^2$ | A | B | M.p. ° C. | Isomer |
|---|---|---|---|---|---|---|---|---|---|---|
| I-1-a-49 | H | $CH_3$ | H | 4 | H | H | $—CH_2—CHOCH_3—(CH_2)_3—$ | | 248 | cis |
| I-1-a-50 | H | $CH_3$ | H | 4 | H | H | $—CH_2—CHOCH_3—(CH_2)_3—$ | | 192 | trans |
| I-1-a-51 | $CH_3$ | $CH_3$ | H | 4 | H | H | $—CH_2—CHOC_2H_5—(CH_2)_3—$ | | 162 | cis/trans |
| I-1-a-52 | H | $CH_3$ | H | 4 | H | H | $—(CH_2)_5—$ | | 243 | — |
| I-1-a-53 | $CH_3$ | $CH_3$ | H | 4 | H | H | $—(CH_2)_5—$ | | 286 | — |
| I-1-a-54 | $CH_3$ | $CH_3$ | H | 4 | H | H | $—CH_2—CHOCH_3—(CH_2)_3—$ | | 264 | trans |
| I-1-a-55 | $CH_3$ | $CH_3$ | H | 4 | H | H | $—CH_2—CHOCH_3—(CH_2)_2—$ | | 230 | cis/trans about 1:1 |
| I-1-a-56 | H | $CH_3$ | H | 4 | H | H | $—CH_2—CHOCH_3—(CH_2)_2—$ | | * 2.19 (s, 3H, Ar—$\underline{CH_3}$); 3.24, 3.25 (2s, together 3H, O$\underline{CH_3}$); 7.42.7.45 (m, 1H, Ar—$\underline{H}$) | cis/trans about 1:1 |
| I-1-a-57 | $CH_3$ | $CH_3$ | H | 4 | H | H | 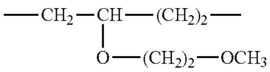 | | 225-227 | cis |
| I-1-a-58 | $CH_3$ | $CH_3$ | H | 4 | H | H | 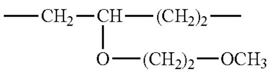 | | ** 2.25 (pseudo-d, 3H, Ar $\underline{CH_3}$); 4.22 (m, 1H, $\underline{CH}$ O—$(CH_2)_2$—O) | trans |
| I-1-a-59 | H | $CH_3$ | H | 4 | 3-F | H | $—CH_2—O—(CH_2)_3—$ | | 246 | — |
| I-1-a-60 | $CH_3$ | $CH_3$ | H | 4 | 3-F | H | $—CH_2—O—(CH_2)_3—$ | | 273 | — |
| I-1-a-61 | H | Cl | H | 4 | 3-Cl | H | $—CH_2—O—(CH_2)_3—$ | | 269 | — |
| I-1-a-62 | H | $CH_3$ | H | 4 | 3-F | H | 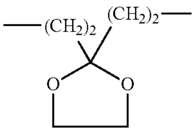 | | 269 | — |
| I-1-a-63 | H | $CH_3$ | H | 4 | 3-Cl | H | 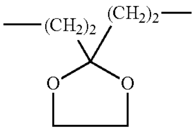 | | 250 | — |
| I-1-a-64 | H | $CH_3$ | H | 4 | 2-F | 3-F | $—(CH_2)_2—O—(CH_2)_2—$ | | * 2.22 (s, 3H, Ar$\underline{CH_3}$) 3.84-3.88 (m, 2H, O—$\underline{CH_2}$) 7.26-7.44 (m, 6H, Ar$\underline{H}$) | |
| I-1-a-65 | $CH_3$ | $CH_3$ | H | 4 | 2-F | 3-F | $—(CH_2)_2—O—(CH_2)_2—$ | | | |
| I-1-a-66 | $CH_3$ | $CH_3$ | H | 4 | 2-F | 5-F | $—(CH_2)_2—O—(CH_2)_2—$ | | * 2.14 (s, 3H, Ar$\underline{CH_3}$) 7.05 (d, 1H, Ar$\underline{H}$) 7.16 (d, 1H, ArH) | |
| I-1-a-67 | H | Cl | H | 4 | 2-F | 5-F | $—(CH_2)_2—O—(CH_2)_2—$ | | | |
| I-1-a-68 | H | $CH_3$ | H | 4 | 2-F | 3-F | $—(CH_2)_2—O—(CH_2)_2—$ | | * 2.22 (s, 3H, Ar$\underline{CH_3}$) 3.68-3.76 (m, 2H, O—$\underline{CH_2}$) 7.29-7.37 (m, 4H, Ar$\underline{H}$) | |
| I-1-a-69 | $CH_3$ | $CH_3$ | H | 4 | 2-F | 3-F | $—(CH_2)_2—O—(CH_2)_2—$ | | * 2.16 (2s, 3H each, Ar$\underline{CH_3}$) 3.65-3.72 (m, 2H, O—$\underline{CH_2}$) 7.07-7.11 (m, 2H, Ar$\underline{H}$) | |
| I-1-a-70 | H | Cl | H | 4 | 2-F | 3-F | $—(CH_2)_2—O—(CH_2)_2—$ | | | |

* $^1$H-NMR (400 MHz, $d_6$-DMSO): shift δ in ppm

Example (I-1-b-1)

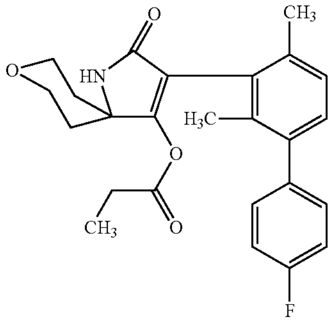 [SMILES: CCC(=O)OC1=C(c2c(C)ccc(-c3ccc(F)cc3)c2C)C(=O)NC12CCOCC2]

0.28 ml (2 mmol) of triethylamine and 20 mg of 4-N,N-dimethylaminopyridine are added to 0.78 g (2 mmol) of the compound according to Example (I-1-a-4) in 50 ml of ethyl acetate. Under reflux, 0.19 g (2 mmol) of propionyl chloride in 5 ml of ethyl acetate are added dropwise. After the reaction has ended (monitored by thin-layer chromatography), the reaction mixture is concentrated under reduced pressure and the residue is purified by reversed-phase chromatography using the solvent system water/acetonitrile. This gives 0.5 g (≙ 58% of theory), m.p. 234° C.

The following compounds of the formula (I-1-b) are obtained analogously to Example (I-1-b-1) and in accordance with the general statements on the preparation:

(I-1-b)

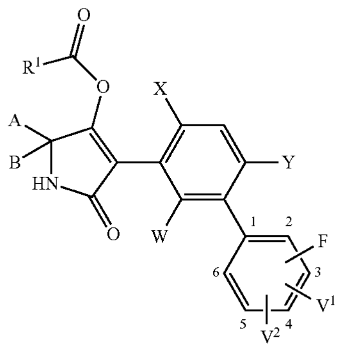

| Ex. No. | W | X | Y | F | $V^1$ | $V^2$ | A | B | $R^1$ | M.p. ° C. | Isomer |
|---|---|---|---|---|---|---|---|---|---|---|---|
| I-1-b-2 | $CH_3$ | $CH_3$ | H | 4 | H | H | $—(CH_2)_2—O—(CH_2)_2—$ | | $CH_3$ | 160 | — |
| I-1-b-3 | $CH_3$ | $CH_3$ | H | 4 | H | H | $—(CH_2)_2—O—(CH_2)_2—$ | | i-$C_3H_7$ | 219 | — |
| I-1-b-4 | H | Cl | H | 4 | H | H | $—(CH_2)_2—O—(CH_2)_2—$ | | i-$C_3H_7$ | 226 | — |
| I-1-b-5 | H | $CH_3$ | H | 4 | H | H | $—(CH_2)_2—O—(CH_2)_2—$ | | $CH_3$ | 249 | — |
| I-1-b-6 | H | $CH_3$ | H | 4 | H | H | $—(CH_2)_2—O—(CH_2)_2—$ | | i-$C_3H_7$ | 249 | — |
| I-1-b-7 | $CH_3$ | $CH_3$ | H | 4 | H | H | $—(CH_2)_2—O—(CH_2)_2—$ | | 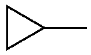 | 233 | — |
| I-1-b-8 | H | $CH_3$ | H | 4 | H | H | $—(CH_2)_2—O—(CH_2)_2—$ | | 4-Cl—Ph* | 203 | — |
| I-1-b-9 | H | $CH_3$ | H | 4 | H | H | $—(CH_2)_2—O—(CH_2)_2—$ | | 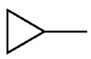 | 207 | — |
| I-1-b-10 | $CH_3$ | $CH_3$ | H | 4 | H | H | $—(CH_2)_2—O—(CH_2)_2—$ | | 4-Cl—Ph* | 242 | — |

*Ph = phenyl

Example (I-1-c-1)

(I-1-c-1)

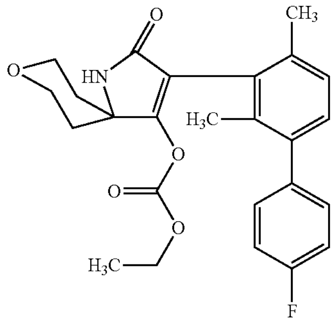

0.28 ml (2 mmol) of triethylamine is added to 0.78 g (2 mmol) of the compound according to Example (I-1-a-4) in 30 ml of dichloromethane. At about 30° C., 0.19 ml (2 mmol) of ethyl chloroformate in 5 ml of dichloromethane is added dropwise, and the mixture is stirred at 30-40° C. After the reaction has ended (monitored by thin-layer chromatography), the reaction mixture is concentrated under reduced pressure and the residue is purified by reversed-phase chromatography using the solvent system water/acetonitrile. This gives 0.18 g (≙ 20% of theory), m.p. 206° C.

The following compounds of the formula (I-1-c) are obtained analogously to Example (I-1-c-1) and in accordance with the general statements on the preparation:

(I-1-c)

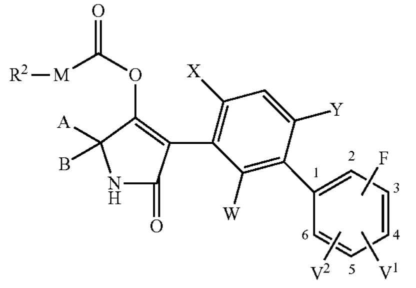

| Ex. No. | W | X | Y | F | $V^1$ | $V^2$ | A | B | M | $R^2$ | M.p. ° C. | Isomer |
|---|---|---|---|---|---|---|---|---|---|---|---|---|
| I-1-c-2 | $CH_3$ | $CH_3$ | H | 4 | H | H | $—(CH_2)_2—O—(CH_2)_2—$ | | O | $CH_3$ | 242 | — |
| I-1-c-3 | H | Cl | H | 4 | H | H | $—(CH_2)_2—O—(CH_2)_2—$ | | O | $CH_3$ | 230 | — |
| I-1-c-4 | H | Cl | H | 4 | H | H | $—(CH_2)_2—O—(CH_2)_2—$ | | O | $C_2H_5$ | 205 | — |
| I-1-c-5 | H | $CH_3$ | H | 4 | H | H | $—(CH_2)_2—O—(CH_2)_2—$ | | O | $C_2H_5$ | 200 | — |
| I-1-c-6 | H | $CH_3$ | H | 4 | H | H | $—(CH_2)_2—O—(CH_2)_2—$ | | O | *Ph—$CH_2$— | 188 | — |
| I-1-c-7 | $CH_3$ | $CH_3$ | H | 4 | H | H | $—(CH_2)_2—O—(CH_2)_2—$ | | O | *Ph—$CH_2$— | 144 | — |

*Ph = phenyl

Example (I-1-f-1)

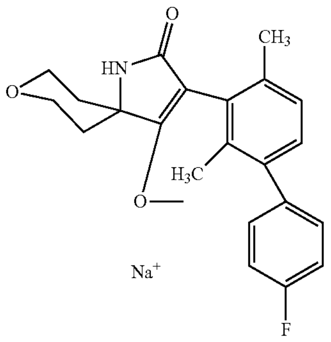 [SMILES: COC1=C(c2c(C)ccc(-c3ccc(F)cc3)c2C)C(=O)NC12CCOCC2 ; [Na+]]

3 ml of 1N aqueous sodium hydroxide solution and 7 ml of water are initially charged, 1.1 g of the compound according to Ex. I-1-a-4 are added a little at a time and dissolved, and the mixture is then concentrated to dryness on a rotary evaporator.

Yield: 1 g (80% of theory)

$^1$H-NMR (400 MHz, $d_6$-DMSO): δ=1.09-1.16 (m, 2H, $CH_2$), 1.91-2.00 (m, 2H, $CH_2$), 2.02, 2.217 (2s, 3H each, Ar—$CH_3$), 3.55-3.63 (m, 2H, $OCH_2$), 3.78-3.84 (m, 2H—O—$CH_2$), 6.75-6.77 (d, 1H, ArH), 6.90-6.95 (m, 1H, Ar—H), 7.15-7.20 (m, 2H, Ar—H), 7.23-7.28 (m, 2H, AR—H) ppm.

The following compounds of the formula (I-1-f) are obtained analogously to Example (I-1-f-1) and in accordance with the general statements on the preparation:

(I-1-f)

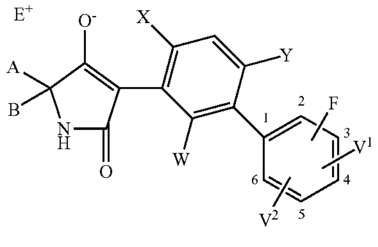

| Ex. No. | W | X | Y | F | $V^1$ | $V^2$ | A | B | E | NMR data | Isomer |
|---|---|---|---|---|---|---|---|---|---|---|---|
| I-1-f-2 | $CH_3$ | $CH_3$ | H | 4 | H | H | $—(CH_2)_2—O—(CH_2)_2—$ | | $K^+$ | * 2.01, 2.16 (2s, 3H each, Ar—$CH_3$)<br>3.55-3.63 (m, 2H, $OCH_2$)<br>6.75-6.77 (m, 1H, Ar—H)<br>6.89-6.91 (m, 1H, Ar—H) | |
| I-1-f-3 | H | $CH_3$ | H | 4 | H | H | $—(CH_2)_2—O—(CH_2)_2—$ | | $Na^+$ | * 1.90-1.98 (m, 2H, $CH_2$)<br>2.23 (s, 3H, Ar—$CH_3$)<br>3.56-3.63 (m, 2H, $OCH_2$)<br>7.02-7.08 (m, 2H, Ar—H) | |
| I-1-f-4 | H | $CH_3$ | H | 4 | H | H | $—(CH_2)_2—O—(CH_2)_2—$ | | $K^+$ | * 1.90-1.97 (m, 2H, $CH_2$)<br>2.23 (s, 3H, Ar—$CH_3$)<br>3.56-3.62 (m, 2H, $OCH_2$)<br>7.01-7.07 (m, 2H, Ar—H) | |

-continued (I-1-f)

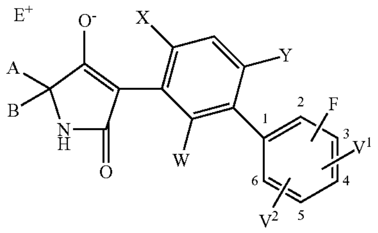

| Ex. No. | W | X | Y | F | $V^1$ | $V^2$ | A | B | E | NMR data | Isomer |
|---|---|---|---|---|---|---|---|---|---|---|---|
| I-1-f-5 | H | Cl | H | 4 | H | H | $—(CH_2)_2—O—(CH_2)_2—$ | | $Na^+$ | * 1.88-1.96 (m, 2H, $\underline{CH_2}$)<br>3.56-3.62 (m, 2H, O—$\underline{CH_2}$)<br>7.56-7.61 (m, 3H, Ar—$\underline{H}$) | |

* $^1$H-NMR (400 MHz, $d_6$-DMSO): shifts δ in ppm

Example (I-1'-a-1)

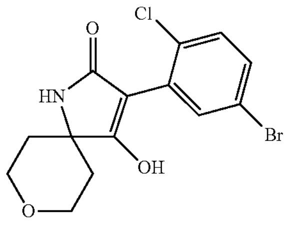 [SMILES: O=C1NC2(CCOCC2)C(O)=C1c1cc(Br)ccc1Cl]

14.1 g of potassium tert-butoxide are initially charged in 50 ml of N,N-dimethylformamide, 22.3 g of the compound according to Ex. II-1'-1, dissolved in 50 ml of DMA, are added dropwise at 50° C., and the mixture is stirred at 50° C. for 1 h. The reaction mixture is poured into ice-water, acidified with dilute hydrochloric acid and filtered off with suction. The residue is initially washed repeatedly with water and then twice slurried with MTBE and filtered off with suction. After 4 days, the mother liquor is re-filtered and washed with MTBE.

Yield: 20 g (98% of theory) m.p. 143° C.

MTBE=methyl tert-butyl ether

The following examples of the formula (I-1'-a) are obtained analogously to Example (I-1'-a-1) and in accordance with the general statements on the preparation in the literature mentioned at the outset:

(I-1'-a)

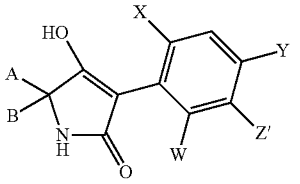

| Ex. No. | W | X | Y | Z' | m.p. ° C. |
|---|---|---|---|---|---|
| I-1-a'-2 | H | $CH_3$ | H | Br | 152 |
| I-1-a'-3 | $CH_3$ | $CH_3$ | H | Br | 184 |

Example (II-1'-1)

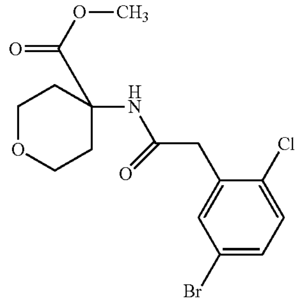 [SMILES: COC(=O)C1(NC(=O)Cc2cc(Br)ccc2Cl)CCOCC1]

At 80° C., 24.9 g of 2-chloro-5-bromophenylacetic acid are stirred in 36.5 ml of thionyl chloride until the evolution of gas has ceased, and the mixture is then concentrated. The residue is taken up in toluene and reconcentrated using a rotary evaporator (=acid chloride). 21.5 g of methyl 4-aminotetrahydropyran-4-carboxylic hydrochloride are initially charged in 80 ml of ethyl acetate, 110 ml of aqueous sodium hydroxide solution are added at 0° C. and then, with vigorous stirring, the acid chloride is made up to 100 ml with ethyl acetate and the remaining aqueous sodium hydroxide solution is simultaneously added dropwise. After the reaction has ended, the product is filtered off with suction (1). The filtrate is extracted with water and ethyl acetate, the organic phase is dried over sodium sulphate, filtered and concentrated. The residue is triturated in a little ethyl acetate and filtered off with suction (2).

Yield 1+2: 22.7 g (=58% of theory) m.p. 151° C.

Example II-1

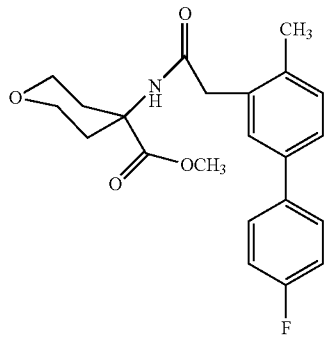 [SMILES: COC(=O)C1(NC(=O)Cc2cc(-c3ccc(F)cc3)ccc2C)CCOCC1]

Under argon, 3.23 g of methyl 4-aminotetrahydropyran-4-carboxylate hydrochloride (16.5 mmol) and 75 ml of anhydrous tetrahydrofuran are initially charged.

At 20° C., 4.6 ml (33 mmol) of triethylamine are added dropwise.

The mixture is stirred for 5 minutes, and 4.2 g of 2-methyl-5-(4-fluorophenyl)phenylacetic acid (15 mmol) are added at 20° C. After 15 minutes, 3.45 ml of triethylamine (25 mmol) are added dropwise, followed immediately afterwards by 0.93 ml of phosphorus oxychloride (10 mmol), the solution should boil moderately. The mixture is stirred under reflux for 30 minutes.

Following analysis by thin-layer chromatography, the solvent is removed using a rotary evaporator and the residue is purified by column chromatography on silica gel (dichloromethane:ethyl acetate=3:1)

Yield: 2.19 g (33% of theory), m.p. 113° C.

The following compounds of the formula (II) are obtained analogously to Example (II-1) and in accordance with the general statements on the preparation:

(II)

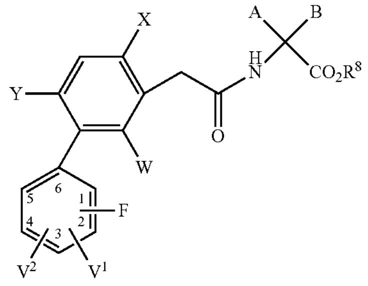

| Ex. No. | W | X | Y | F | $V^1$ | $V^2$ | A | B | $R^8$ | M.p. ° C. | Isomer |
|---|---|---|---|---|---|---|---|---|---|---|---|
| II-2 | H | $CH_3$ | H | 4 | 3-F | H | $—(CH_2)_2—O—(CH_2)_2—$ | | $CH_3$ | 117 | — |
| II-3 | $CH_3$ | $CH_3$ | H | 4 | H | H | $—(CH_2)_2—O—(CH_2)_2—$ | | $CH_3$ | 66 | — |
| II-4 | $CH_3$ | $CH_3$ | H | 4 | 3-F | H | $—(CH_2)_2—O—(CH_2)_2—$ | | $CH_3$ | wax | — |
| II-5 | H | $CH_3$ | H | 3 | 4-Cl | H | $—(CH_2)_2—O—(CH_2)_2—$ | | $CH_3$ | 176 | — |
| II-6 | H | $CH_3$ | H | 4 | H | H | $—CH_2—CHCH_3—O—(CH_2)_2—$ | | $CH_3$ | glass-like solid | β |
| II-7 | $CH_3$ | $CH_3$ | H | 4 | H | H | $—CH_2—CHCH_3—O—(CH_2)_2—$ | | $CH_3$ | 75 | β |
| II-8 | H | $CH_3$ | H | 4 | H | H | 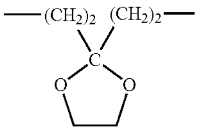 | | $CH_3$ | 89 | — |
| II-9 | $CH_3$ | $CH_3$ | H | 4 | H | H | 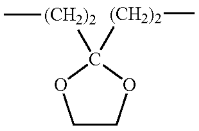 | | $CH_3$ | 68 | — |
| II-10 | $CH_3$ | $CH_3$ | H | 4 | H | H | 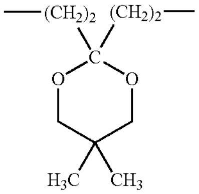 | | $CH_3$ | 121 | — |
| II-11 | H | Cl | H | 4 | Hl | H | $—(CH_2)_2—O—(CH_2)_2—$ | | $CH_3$ | oil | — |
| II-12 | H | $CH_3$ | H | 4 | H | H | $—CH_2—CHOC_2H_5—(CH_2)_3—$ | | $CH_3$ | 125 | β |
| II-13 | $CH_3$ | $CH_3$ | H | 4 | H | H | $—CH_2—CHOC_2H_5—(CH_2)_3—$ | | $CH_3$ | 62 | β |
| II-14 | H | $CH_3$ | H | 4 | H | H | $—CH_2—CHOCH_3—(CH_2)_3—$ | | $CH_3$ | resin | mixture |
| II-15 | $CH_3$ | $CH_3$ | H | 4 | H | H | $—CH_2—CHOCH_3—(CH_2)_3—$ | | $CH_3$ | resin | mixture |
| II-16 | H | $CH_3$ | H | 4 | H | H | $—(CH_2)_5—$ | | $CH_3$ | 137 | — |
| II-17 | $CH_3$ | $CH_3$ | H | 4 | H | H | $—(CH_2)_5—$ | | $CH_3$ | 145 | — |
| II-18 | $CH_3$ | $CH_3$ | $CH_3$ | 4 | H | H | $—(CH_2)_2—O—(CH_2)_2—$ | | $CH_3$ | 158 | — |
| II-19 | $CH_3$ | $CH_3$ | H | 4 | H | H | 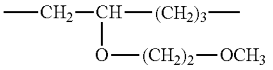 | | $CH_3$ | * 3.23, 3.24 (2S, together 3H, O<u>CH<sub>3</sub></u>), 3.53 (s, 3H, $CO_2$<u>CH<sub>3</sub></u>), 7.02-7.07 (m, 1H, Ar—<u>H</u>). | cis:trans about 2:1 |
| II-20 | H | $CH_3$ | H | 4 | H | H | 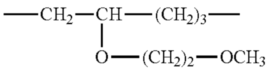 | | $CH_3$ | * 2.27, 2.29 (2s, together 3H, Ar—$CH_3$), 3.21 (2s, together 3H, O $CH_3$), 3.53 (2s, together 3H, $CO_2$ $CH_3$), 7.20-7.26 (m, 3H, Ar<u>H</u>) | cis:trans about 1:1 |

-continued (II)

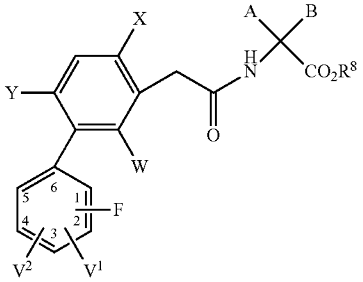

| Ex. No. | W | X | Y | F | $V^1$ | $V^2$ | A | B | $R^8$ | M.p. ° C. | Isomer |
|---|---|---|---|---|---|---|---|---|---|---|---|
| II-21 | H | Cl | H | 4 | H | H | $—CH_2—CH—(CH_2)_3—$<br>$|$<br>$O—(CH_2)_2—OCH_3$ | | $CH_3$ | * 3.22, 3.23 (2S, together 3H, O $\underline{CH_3}$), 3.35-3.49 (m, 4H, O—$\underline{CH_2}$—$\underline{C}H_2$—O), 3.53, 3.54 (2s, together 3H, $CO_2$ $\underline{CH_3}$), 7.25-7.30 (m, 2H, Ar—$\underline{H}$) | cis:trans about 1:1 |
| II-22 | H | Cl | H | 4 | H | H | $—CH_2—O—(CH_2)_3—$ | | $CH_3$ | oil | — |
| II-23 | $CH_3$ | $CH_3$ | H | 4 | H | H | $—CH_2—O—(CH_2)_3—$ | | $CH_3$ | wax | — |
| II-24 | H | $CH_3$ | H | 4 | H | H | $—CH_2—O—(CH_2)_3—$ | | $CH_3$ | 111 | — |
| II-25 | $CH_3$ | $CH_3$ | H | 4 | H | H | $—CH_2—CHOCH_3—(CH_2)_2—$ | | $C_2H_5$ | oil | cis:trans about 1:1 |
| II-26 | H | $CH_3$ | H | 4 | H | H | $—CH_2—CHOCH_3—(CH_2)_2—$ | | $C_2H_5$ | oil | cis:trans about 1:1 |
| II-27 | $CH_3$ | $CH_3$ | H | 4 | H | H | $—CH_2—CH—(CH_2)_2—$<br>$|$<br>$O—(CH_2)_2—OCH_3$ | | $C_2H_5$ | * 3.66 (m, 2H, $\underline{CH_2}$—Ar), 4.03 (m, 1H, C$\underline{H}$O—$(CH_2)_2$), 4.15 (a, 2H, O—$\underline{CH_2}$—$CH_3$) | cis |
| II-28 | $CH_3$ | $CH_3$ | H | 4 | H | H | $—CH_2—CH—(CH_2)_2—$<br>$|$<br>$O—(CH_2)_2—OCH_3$ | | $C_2H_5$ | * 3.66 (m, 2H, $\underline{CH_2}$—Ar), 4.15 (m, 3H, O—$\underline{CH_2}$—$CH_3$, C$\underline{H}$O—$(CH_2)_2$—) | trans |

* $^1$H-NMR (400 MHz, $CDCl_3$): shifts δ in ppm

Example III-1'

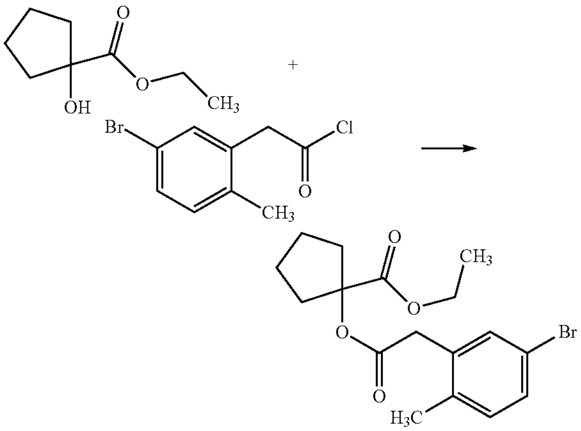

III-1'

17.23 g (108.8 mmol) of ethyl 1-hydroxycyclopentanecarboxylate and 26.95 g (108.8 mmol) of 3-bromo-6-methylphenylacetyl chloride are combined, stirred at an oil bath temperature of 120° C. for 6 h and finally briefly heated to 140° C. and degassed on an oil pump.

Yield: 39.73 g of an oil (99% of theory), log P (acidic) 4.52

Example I-2'-a-1

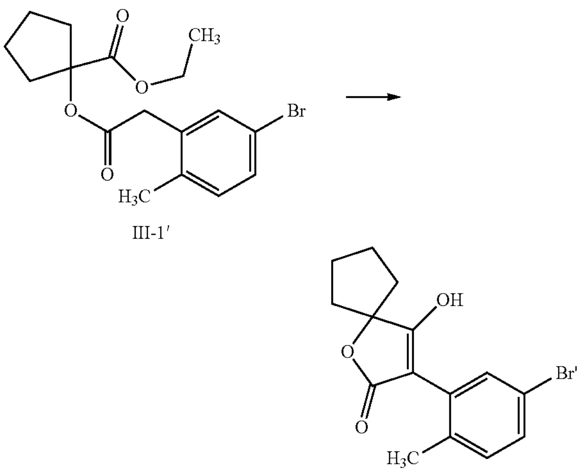

III-1'

I-2'-a-1

14.73 g (131 mmol) of potassium tert-butoxide are initially charged in 50 ml of dimethylformamide (DMF) and cooled to 0° C. 32.32 g (87.5 mmol) of the compound according to Example III-1', dissolved in 200 ml of DMF, are added dropwise at 0-10° C. and stirred overnight at RT. The DMF is distilled off, the residue is added to water and acidified with 10% strength HCl and the precipitate is filtered off with suction and dried in a drying cabinet overnight.

Yield: 27.61 g (93% of theory), log P (acidic) 2.56

Example I-2-a-1 Process C

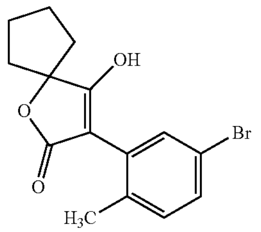

+

I-2'-a-1

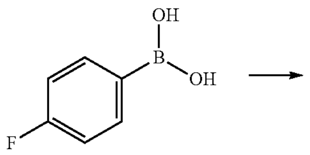

(IV)

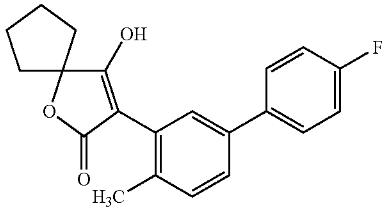

I-2-a-1

1.778 g (5.5 mmol) of the compound according to Example I-2'-a-1 are suspended in 40 ml of dimethoxyethane, 0.923 g (6.6 mmol) of 4-fluoroboronic acid and 0.381 g (0.33 mmol) of tetrakis(triphenylphosphine)palladium are added under argon, the mixture is stirred at RT for 15 min, 27 ml of 20% strength $Na_2CO_3$ solution are added and the mixture is stirred at 80° C. for 4 h. For work-up, 1N NaOH is added, the mixture is extracted 2× with ether and the alkaline phase is filtered and acidified with dilute HCl. The precipitate is filtered off with suction and dried.

Yield: 1.44 g (77% of theory), log P (acidic) 3.12

Example I-2-a-15

Process B

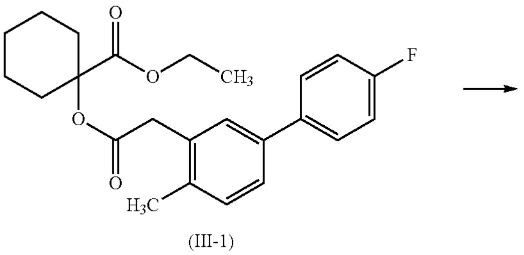

(III-1)

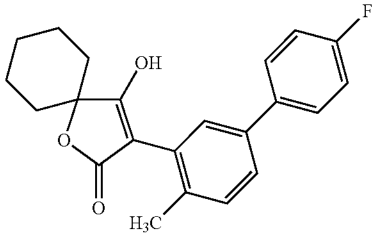

(I-2-a-15)

1.99 g (5 mmol) of the crude product of the compound according to Example III-1 are initially charged in 10 ml of DMF, 0.845 g (7.52 mmol) of potassium tert-butoxide are added, the mixture is stirred at room temperature overnight, the DMF is removed using a rotary evaporator and the residue is partitioned between water and methyl tert-butyl ether. The aqueous phase is acidified with HCl, extracted with $CH_2Cl_2$ and separated, and the organic phase is dried and concentrated.

Yield: 1.58 g (90% of theory), log P (acidic) 3.40

The following compounds of the formula (I-2-a) are obtained analogously to Examples (I-2-a-1) and (I-2-a-15) and in accordance with the general statements on the preparation:

(I-2-a)

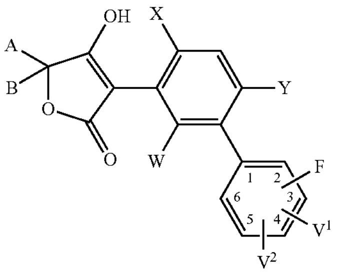

| Ex. No. | W | X | Y | F | $V^1$ | $V^2$ | A | B | logP |
|---|---|---|---|---|---|---|---|---|---|
| I-2-a-2 | H | Cl | H | 4 | 3-F | H | $-(CH_2)_4-$ | | 3.19 |
| I-2-a-3 | H | $CH_3$ | H | 4 | 3-F | H | $-(CH_2)_4-$ | | 3.25 |
| I-2-a-4 | H | $CH_3$ | H | 4 | 3-Cl | H | $-(CH_2)_4-$ | | 3.50 |
| I-2-a-5 | H | Cl | H | 4 | 2-F | H | $-(CH_2)_4-$ | | 3.16 |

-continued (I-2-a)

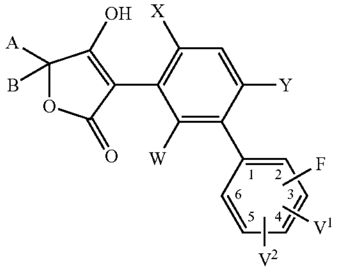

| Ex. No. | W | X | Y | F | $V^1$ | $V^2$ | A B | logP |
|---|---|---|---|---|---|---|---|---|
| I-2-a-6 | H | Cl | H | 4 | 3-F | 5-F | $-(CH_2)_4-$ | 3.35 |
| I-2-a-7 | H | Cl | H | 4 | H | H | $-(CH_2)_4-$ | 3.09 |
| I-2-a-8 | H | Cl | H | 4 | 3-F | H | $-(CH_2)_5-$ | 3.48 |
| I-2-a-9 | H | Cl | H | 4 | 3-F | 5-F | $-(CH_2)_5-$ | 3.65 |
| I-2-a-10 | H | Cl | H | 4 | H | H | $-(CH_2)_5-$ | 3.37 |
| I-2-a-11 | $CH_3$ | $CH_3$ | H | 4 | H | H | $-(CH_2)_2-O-(CH_2)_2-$ | 2.76 |
| I-2-a-12 | H | $CH_3$ | H | 4 | H | H | $-(CH_2)_2-O-(CH_2)_2-$ | 2.62 |
| I-2-a-13 | H | $CH_3$ | H | 4 | 3-F | H | $-(CH_2)_2-O(CH_2)_2-$ | 2.69 |
| I-2-a-14 | H | $CH_3$ | H | 4 | 3-F | 5-F | $-(CH_2)_2-O-(CH_2)_2-$ | 2.87 |
| I-2-a-15 | H | $CH_3$ | H | 4 | H | H | $-(CH_2)_5-$ | 3.4 |
| I-2-a-16 | $CH_3$ | $CH_3$ | H | 4 | 3-F | H | $-(CH_2)_2-O-(CH_2)_2-$ | 2.88 |

Example I-2-b-1

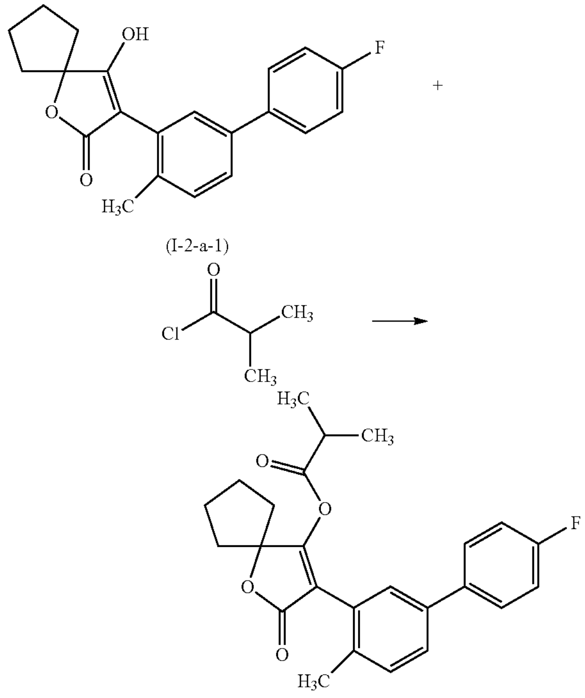

(I-2-a-1)

(I-2-b-1)

0.338 g (1 mmol) of the compound according to Example (I-2-a-1) is initially charged in 20 ml of dichloromethane, 0.111 g (1.1 mmol) of triethylamine is added at room temperature, 0.112 g (1.05 mmol) of isobutyryl chloride is added dropwise at 0-10° C., the mixture is stirred at room temperature overnight and then extracted with dilute citric acid and saturated $NaHCO_3$ solution, the organic phase is dried and the solvent is distilled off.

Yield: 0.35 g (86% of theory), log P (acidic) 4.85

Examples (I-2-b-2) and (I-2-b-3) are obtained analogously to Example (I-2-b-1)

(I-2-b-2)

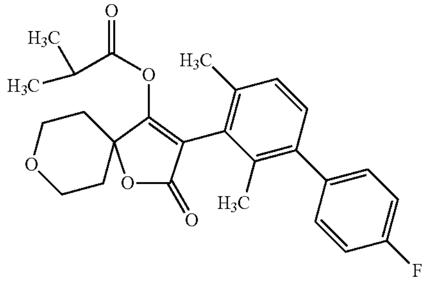

logP 4, 46

(I-2-b-3)

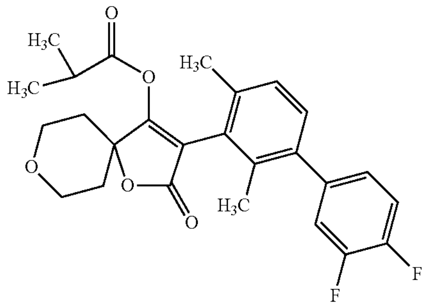

logP 4.56

Example I-2-c-1

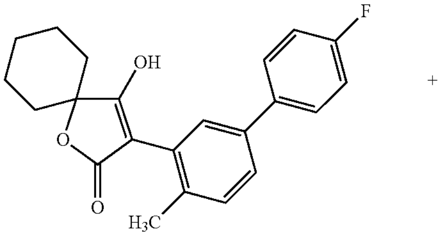

(I-2-a-15)

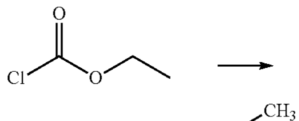

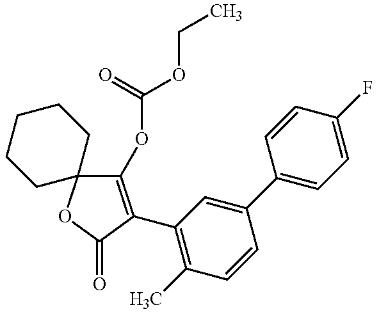

(I-2-c-1)

0.1 g (0.284 mmol) of the compound according to Example I-2-a-15 is initially charged in 5 ml of dichloromethane, 0.034 g (0.341 mmol) of triethylamine and 0.037 g (0.341 mmol) of ethyl chloroformate are added and the mixture is stirred at room temperature overnight, concentrated using a rotary evaporator and purified by preparative HPLC (silica gel RP 18, acetonitrile/water).

Yield: 0.057 g (48% of theory), log P (acidic) 4.84

Example I-2-c-2 is obtained analogously to Example I-2-c-1

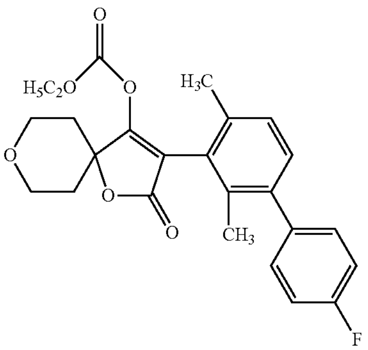

logP (acidic) 4.04

Example (III-1)

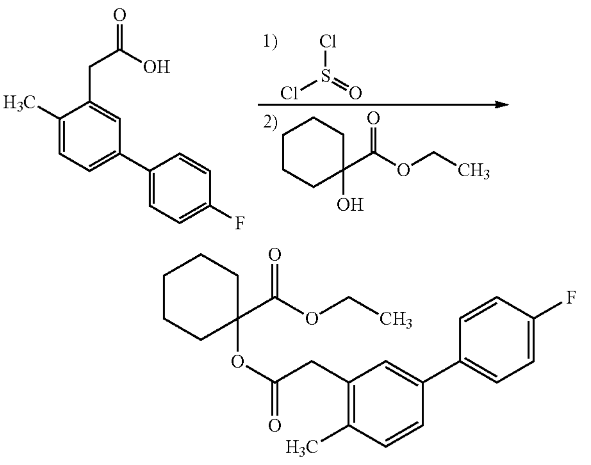

1.221 g (5 mmol) of 2-methyl-5-(4-fluorophenyl)phenylacetic acid are initially charged in 30 ml of toluene, 1.190 g (10 mmol) of thionyl chloride are added, the mixture is boiled under reflux for 1 h, 1 drop of DMF is added and the mixture is boiled for a further 20 min (until the evolution of gas has ceased), cooled and concentrated using a rotary evaporator.

In 30 ml of toluene, this crude acid chloride and 1.435 g (5 mmol) of ethyl 1-hydroxy-cyclohexanecarboxylate are boiled under reflux for 8 h, and the mixture is then cooled and concentrated using a rotary evaporator. The crude product is dissolved in MTB ether and washed with 5% strength NaOH solution, separated, dried and concentrated.

Yield: 1.99 g of an oil (quant), log P (acidic) 5.43

The following novel compounds of the formulae (XIX) and (XXIII) are obtained analogously to the processes described in WO 2005/016873 for preparing compounds of the formulae (XIX) and (XXIII):

(XXIII)

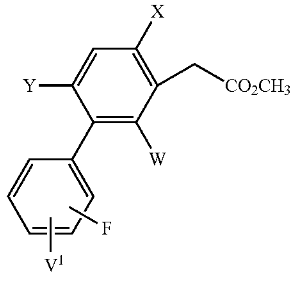

| Ex. No. | W | X | Y | F | $V^1$ | M.p. ° C. |
|---|---|---|---|---|---|---|
| XXIII-1 | H | $CH_3$ | H | 4 | 3-F | * oil |
| XXIII-2 | H | $CH_3$ | H | 3-F | 4-Cl | * oil |
| XXIII-3 | $CH_3$ | $CH_3$ | H | 4-F | 3-F | * oil |
| XXIII-4 | $CH_3$ | $CH_3$ | H | 3-F | 4-Cl | * oil |

* Without further characterization, the compounds were directly hydrolysed to the compounds (XIX).

(XIX)

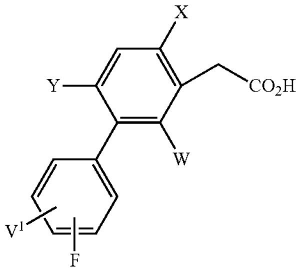

| Ex. No. | W | X | Y | F | $V^1$ | $^1$H NMR |
|---|---|---|---|---|---|---|
| XIX-1 | H | $CH_3$ | H | 4 | 3-F | *2.28 (s, 3H, Ar—$CH_3$)<br>3.65 (s, 2H, $CH_2$)<br>7.25 (d, 1H, Ar—H) |
| XIX-2 | H | $CH_3$ | H | 3 | 4-Cl | *2.28 (s, 3H, Ar—$CH_3$)<br>3.66 (s, 2H, Ar—$CH_2$)<br>7.27 (d, 2H, Ar—H)<br>7.47-7.50 (m, 1H, Ar—H) |
| XIX-3 | $CH_3$ | $CH_3$ | H | 4 | 3-F | *2.13 (s, 3H, Ar—$CH_3$)<br>2.31 (s, 3H, Ar—$CH_3$)<br>3.68 (s, 2H, $CH_2$)<br>6.98 (d, 1H, Ar—H)<br>7.39-7.46 (m, 1H, Ar—H) |
| XIX-4 | $CH_3$ | $CH_3$ | H | 3 | 4-Cl | *2.13 (s, 3H, Ar—$CH_3$)<br>2.31 (s, 3H, Ar—$CH_3$)<br>3.68 (s, 2H, Ar—$CH_2$)<br>7.00 (d, 1H, Ar—H)<br>7.08-7.12 (m, 2H, Ar—H)<br>7.25-7.28 (m, 1H, Ar—H)<br>7.59 (t, 1H, Ar—H) |

*$^1$H-NMR (400 MHz, $d_6$-DMSO): shifts δ in ppm

Determination of the Log P Values

The log P values given in the table were determined in accordance with EEC Directive 79/831 Annex V.A8 by HPLC (High Performance Liquid Chromatography) on a reversed-phase column (C18). Temperature: 43° C.

Mobile phases for the determination in the acidic range (pH 2.3): 0.1% aqueous phosphoric acid, acetonitrile; linear gradient from 10% acetonitrile to 90% acetonitrile The calibration was carried out using unbranched alkan-2-ones (having 3 to 16 carbon atoms) with known log P values (determination of the log P values by the retention times using linear interpolation between two successive alkanones).

The lambda max values were determined in the maxima of the chromatographic signals using the UV spectra from 200 nm to 400 nm.

Use Examples

Example A

Boosting of the penetration into the plant by ammonium salts or phosphonium salts, and synergistic boosting of penetration into the plants by ammonium/phosphonium salts in combination with penetration promoters This test measured the penetration of active compounds through enzymatically isolated cuticles of apple leaves.

The leaves used were cut in the fully developed state from apple trees of the Golden Delicious variety. The cuticles were isolated as follows:

first of all, leaf discs labelled on the underside with dye and formed by punching were filled by means of vacuum infiltration with a pectinase solution (0.2% to 2% strength) buffered to a pH of between 3 and 4, sodium azide was then added and the leaf discs thus treated were left to stand until the original leaf structure broke down and the non-cellular cuticle underwent detachment.

After that, only those cuticles from the top leaf sides that were free from stomata and hairs were used. They were washed a number of times in alternation with water and a buffer solution of pH 7. The clean cuticles obtained were, finally, applied to Teflon plaques, smoothed with a gentle jet of air, and dried.

In the next step the cuticular membranes obtained in this way were placed in stainless steel diffusion cells (=transport chambers) for the purpose of membrane transport investigations. For these investigations the cuticles were placed centrally using tweezers on the edges of the diffusion cells, which were coated with silicone grease, and sealed with a ring, which was likewise greased. The arrangement had to be chosen so that the morphological outer side of the cuticles was directed outwards, in other words facing the air, while the original inner side was facing the inside of the diffusion cell.

The diffusion cells were filled with a 30% strength ethylene glycol/water solution. Penetration was determined by applying 10 μl of the spray liquor of the composition below to the outer side of each of the cuticles. The spray liquor is prepared using local mains water of medium hardness.

After the spray liquors had been applied, the water was evaporated and the chambers were inverted and placed into theromstated troughs, in which the temperature and humidity over the cuticles was adjustable by means of a gentle stream of air onto the cuticles, with the spray coating (20° C., 60% rh). At regular intervals, samples were taken using an autosampler, and the amount of active compound was determined using HPLC.

The results of the experiment are apparent from the table below. The numbers stated represent average values from 8 to 10 measurements. It can clearly be seen that ammonium sulphate, even on its own, significantly improves the penetration, and that together with RME there is a superadditive (synergistic) effect.

TABLE A

| | Penetration after 24 h/% | | |
|---|---|---|---|
| Active compound | EC | EC + RME (1 g/l) | EC + RME (1 g/l) + AS (1 g/l) |
| Example I-1-a-4 500 ppm in DMF/ emulsifier W 7:1 (w/w) | 3 | 8 | 30 |

RME = rapeseed oil methyl ester (formulated for use as 500 EW, concentration figure in g of active compound/l)
AS = ammonium sulphate
EC = emulsifiable concentrate

Example 1

Phaedon Test (PHAECO Spray Treatment)

Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with an active compound preparation of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show, at an application rate of 500 g/ha, an efficacy of ≥80% after 7 d: I-1-a-1, I-1-a-2, I-1-a-3, I-1-a-4, I-1-a-5, I-1-a-6, I-1-a-10, I-1-a-11, I-1-a-21, I-1-a-22, I-1-a-23, I-1-a-24, I-1-a-25, I-1-a-28, I-1-a-27, I-1-a-29, I-1-a-30, I-1-a-31, I-1-a-32, I-1-a-33, I-1-a-34, I-1-a-35, I-1-a-37, I-1-a-38, I-1-a-39, I-1-a-41, I-1-a-52, I-2-a-1, I-1-a-2, I-2-a-3, I-2-a-4, I-2-a-8, I-2-a-9, I-2-a-10, I-2-a-11, I-2-a-15, I-2-a-16, I-2-b-2, I-1-b-5, I-1-b-6, I-1-c-3, I-1-c-4, I-1-c-5, I-2-c-1, I-1-f-1

In this test, for example, the following compounds of the Preparation Examples show, at an application rate of 100 g/ha, an efficacy of ≥80% after 7 d: I-1-a-7, I-2-a-2, I-2-a-5, I-2-a-6, I-2-a-7.

Example 2

*Spodoptera frugiperda* Test (SPODFR Spray Treatment)

Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with water to the desired concentration.

Discs of maize leaves (*Zea mays*) are sprayed with an active compound preparation of the desired concentration and, after drying, populated with caterpillars of the army worm (*Spodoptera frugiperda*).

After the desired period of time, the effect in % is determined. 100% means that all the caterpillars have been killed; 0% means that none of the caterpillars have been killed.

In this test, for example, the following compounds of the Preparation Examples show, at an application rate of 500 g/ha, an efficacy of ≥80% after 7 d: I-1-a-1, I-1-a-3, I-1-a-4, I-1-a-5, I-1-a-6, I-1-a-8, I-1-a-10, I-1-a-11, I-1-a-12, I-1-a-16, I-1-a-17, I-1-a-19, I-1-a-21, I-1-a-25, I-1-a-28, I-1-a-29, I-1-a-30, I-1-a-34, I-1-a-35, I-1-a-38, I-1-a-41, I-1-a-42, I-1-a-50, I-1-a-54, I-1-a-47, I-1-a-51, I-1-a-52, I-1-a-53, I-1-a-55, I-1-b-1, I-1-b-2, I-1-b-3, I-2-a-1, I-2-a-3, I-2-a-4, I-2-a-8, I-2-a-9, I-2-a-10, I-2-a-11, I-2-a-12, I-1-b-4, I-1-b-5, I-1-b-6, I-1-c-2, I-1-c-3, I-1-c-4, I-1-c-5, I-2-b-2, I-2-c-1, I-2-c-2, I-1-f-1.

In this test, for example, the following compounds of the Preparation Example show, at an application rate of 100 g/ha, an efficacy of ≥80% after 7 d: I-2-a-6

Example 3

Myzus Test (MYZUPE Spray Treatment)

Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) which are infested by all stages of the green peach aphid (*Myzus persicae*) are sprayed with an active compound preparation of the desired concentration.

After the desired period of time, the effect in % is determined. 100% means that all aphids have been killed; 0% means that none of the aphids have been killed.

In this test, for example, the following compounds of the Preparation Examples show, at an application rate of 500 g/ha, an efficacy of ≥80% after 6 d: I-1-a-1, I-1-a-2, I-1-a-3, I-1-a-4, I-1-a-5, I-1-a-6, I-1-a-7, I-1-a-8, I-1-a-9, I-1-a-10, I-1-a-15, I-1-a-16, I-1-a-17, I-1-a-18, I-1-a-20, I-1-a-21, I-1-a-22, I-1-a-23, I-1-a-24, I-1-a-25, I-1-a-27, I-1-a-28, I-1-a-29, I-1-a-30, I-1-a-31, I-1-a-32, I-1-a-33, I-1-a-34, I-1-a-35, I-1-a-36, I-1-a-37, I-1-a-38, I-1-a-39, I-1-a-40, I-1-a-41, I-1-a-42, I-1-a-43, I-1-a-44, I-1-a-46, I-1-a-47, I-1-a-48, I-1-a-49, I-1-a-50, I-1-a-51, I-1-a-52, I-1-a-53, I-1-a-54, I-1-a-55, I-1-a-56, I-1-a-11, I-1-a-12, I-1-b-1, I-1-b-2, I-1-b-3, I-1-b-4, I-1-b-5, I-1-b-6, I-1-c-1, I-1-c-2, I-1-c-3, I-1-c-4, I-1-c-5, I-2-a-1, I-2-a-3, I-2-a-4, I-2-a-8, I-2-a-9, I-2-a-10, I-2-a-11, I-2-a-12, I-2-a-13, I-2-a-1, I-2-a-15, I-2-a-16, I-2-b-3, I-2-c-1, I-2-c-2, I-1-f-1.

In this test, for example, the following compounds of the Preparation Examples show, at an application rate of 100 g/ha, an efficacy of ≥80% after 5 d: I-2-a-2, I-2-a-5, I-2-a-7.

Example 4

*Tetranychus* Test, OP-Resistent (TETRUR Spray Treatment)

Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) which are infested by all stages of the greenhouse red spider mite (*Tetranychus urticae*) are sprayed with an active compound preparation of the desired concentration.

After the desired period of time, the effect in % is determined. 100% means that all spider mites have been killed; 0% means that none of the spider mites have been killed.

In this test, for example, the following compounds of the Preparation Examples show, at an application rate of 100 g/ha, an efficacy of ≥80% after 6 d: I-1-a-3, I-1-a-7, I-1-a-8, I-1-a-9, I-1-a-10, I-1-a-12, I-1-a-16, I-1-a-17, I-1-a-21, I-1-a-22, I-1-a-24, I-1-a-25, I-1-a-28, I-1-a-30, I-1-a-34, I-1-a-35, I-1-a-36, I-1-a-37, I-1-a-38, I-1-a-39, I-1-a-40, I-1-a-41, I-1-a-43, I-1-a-45, I-1-a-46, I-1-a-47, I-1-a-48, I-1-a-49, I-1-a-50, I-1-a-51, I-1-a-52, I-1-a-54, I-1-a-56, I-1-b-5, I-1-b-6, I-2-c-1, I-2-a-6, I-2-a-9, I-2-a-16, I-1-b-4, I-1-b-1, I-1-b-2, I-1-b-3, I-1-c-1, I-1-c-2, I-1-c-4, I-1-c-5, I-1-f-1

In this test, for example, the following compounds of the Preparation Examples show, at an application rate of 20 g/ha, an efficacy of ≥80% after 6 d: I-1-a-1, I-1-a-4, I-1-a-5, I-1-a-6.

Example 5

*Meloidogyne* Test (MELON Spray Treatment)

Solvent: 80 parts by weight of acetone

To produce a suitable preparation of active compound, 1 part by weight of active compound is mixed with the stated amount of solvent, and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After the desired period of time, the nematicidal activity is determined in % by the formation of galls. 100% means that no galls are formed; 0% means that the number of galls on the treated plants corresponds to that of the untreated control.

In this test, for example, the following compounds of the Preparation Examples show, at an application rate of 20 ppm, an efficacy of ≥80% after 14 d: I-1-a-22, I-1-a-23, I-1-a-25, I-1-a-28, I-1-a-53, I-1-a-55, I-2-a-1, I-2-a-3, I-2-a-4, I-2-a-9, I-2-a-10, I-2-a-11, I-2-c-1.

Example 6

*Aphis gossypii* Test; (AMIGO G)

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration.

Cotton plants (*Gossypium hirsutum*) which are heavily infested by the cotton aphid (*Aphis gossypii*) are watered with an active compound preparation of the desired concentration.

After the desired period of time, the kill in % is determined. 100% means that all aphids have been killed; 0% means that none of the aphids have been killed.

In this test, for example, the following compounds of the Preparation Examples show, at an application rate of 20 ppm, an efficacy of ≥80% after 10 days:

Examples Nos. I-1-a-4, I-1-a-8, I-1-a-20, I-1-a-21, I-1-a-23, I-1-a-25, I-1-a-33, I-1-a-34, I-1-a-54, I-1-a-55, I-2-a-13, I-2-b-2, I-1-b-1, I-1-b-2, I-1-b-3, I-1-c-1, I-1-c-4, I-1-v-1

Example 7

*Myzus persicae* Test; (MYZUPE G)

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage plants (*Brassica oleracea*) which are heavily infested by the green peach aphid (*Myzus persicae*) are watered with an active compound preparation of the desired concentration.

After the desired period of time, the kill in % is determined. 100% means that all aphids have been killed; 0% means that none of the aphids have been killed.

In this test, for example, the following compounds of the Preparation Examples show, at an application rate of 20 ppm, an efficacy of ≥80% after 10 days:

Example Nos. I-1-a-1, I-1-a-3, I-1-a-4, I-1-a-11, I-1-a-17, I-1-a-20, I-1-a-23, I-1-a-25, I-1-a-33, I-1-a-34, I-1-a-56, I-1-b-2, I-1-b-3, I-1-b-4, I-2-b-3, I-1-c-2, I-2-c-2, I-1-c-3, I-1-c-4, I-2-a-12

Example 8

*Tetranychus* Test; OP-Resistent (TETRUR G)

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are watered with an active compound preparation of the desired concentration.

After the desired period of time, the effect in % is determined. 100% means that all spider mites have been killed; 0% means that none of the spider mites have been killed.

In this test, for example, the following compounds of the Preparation Examples show, at an application rate of 20 ppm, an efficacy of ≥80% after 14 days:

Example Nos. I-1-a-3, I-1-a-5, I-1-a-6, I-1-a-8, I-1-a-11, I-1-a-16, I-1-a-17, I-1-a-20, I-1-a-21, I-1-a-23, I-1-a-25, I-1-a-33, I-1-a-34, I-1-a-50, I-1-a-54, I-1-a-55, I-1-b-1, I-1-b-2, I-1-b-3, I-1-b-4, I-1-b-5, I-1-b-6, I-2-b-2, I-2-b-3, I-1-c-1, I-1-c-2, I-1-c-3, I-1-c-4, I-1-c-5, I-1-f-1, I-2-c-2, I-2-a-12, I-2-a-13

Example 9

*Lucilia cuprina* Test (LUCICU)

Solvent: dimethyl sulphoxide

To produce a suitable preparation of active compound, 1 part by weight of active compound is mixed with the stated amount of water, and the concentrate is diluted with water to the desired concentration.

Containers containing horse meat treated with the active compound preparation of the desired concentration are populated with *Lucilia cuprina* larvae.

After the desired period of time, the kill in % is determined. 100% means that all larvae have been killed; 0% means that none of the larvae have been killed.

In this test, for example, the following compounds of the Preparation Examples show, at an application rate of 100 ppm, an efficacy of ≥80%: I-1-a-3, I-1-a-4, I-1-a-6, I-1-a-12, I-2-a-3, I-2-a-10.

Example 10

*Boophilus microplus* Test (BOOPMI Injection)

Solvent: Dimethyl sulphoxide

To produce a suitable preparation of active compound, 1 part by weight of active compound is mixed with the stated amount of solvent, and the concentrate is diluted with solvent to the desired concentration.

The solution of active compound is injected into the abdomen (*Boophilus microplus*) and the animals are transferred into dishes and stored in a climatized room.

After the desired period of time, the effect in % is determined. In this case 100% means that none of the ticks has laid fertile eggs.

In this test, for example, the following compounds of the Preparation Examples show, at an application rate of 20 µg/animal, an efficacy of ≥80%: I-1-a-3, I-1-a-6, I-1-a-12, I-2-a-1, I-2-a-3, I-2-a-10, I-2-c-1.

Example 11

*Heliothis virescens* Test—Treatment of Transgenic Plants

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trademark of Monsanto Comp. USA) are treated by being dipped into the preparation of active compound of the desired concentration and are populated with the tobacco budworm *Heliothis virescens* while the leaves are still moist.

After the desired period of time, the kill of the insects is determined.

Example 12

Critical Concentration Test/Soil Insects—Treatment of Transgenic Plants

Test insect: *Diabrotica balteata*—larvae in the soil
Solvent: 7 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example 13

Activity Boost Through Ammonium/Phosphonium Salts in Combination with Penetrants

*Myzus persicae* Test
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration. For application with ammonium salts or phosphonium salts and penetration promoters (rapeseed oil methyl ester 500 EW) these are in each case added in a concentration of 1000 ppm to the spray liquor.

Bell pepper plants (*Capsicum annuum*) heavily infested by the green peach aphid (*Myzus persicae*) are sprayed to runoff point with the preparation of active compound at the desired concentration.

After the desired period of time, the kill in % is determined. 100% means that all animals have been killed; 0% means that none of the animals have been killed.

TABLE

| Active compound | Concentration (ppm) | Kill (%) after 6 d | +AS 1000 ppm | +RME 1000 pm | +AS + RME 1000 ppm each |
|---|---|---|---|---|---|
| I-1-a-1 | 4 | 0 | 15 | 70 | 99 |
| | 0.8 | 0 | 0 | 0 | 15 |
| I-1-a-4 | 4 | 15 | 20 | 5 | 98 |
| | 0.8 | 0 | 0 | 0 | 5 |

Example 14

*Aphis gossypii* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration. For application with ammonium salts or phosphonium salts and penetration promoters (rapeseed oil methyl ester 500 EW) these are in each case added in a concentration of 1000 ppm to the spray liquor.

Cotton plants (*Gossypium hirsutum*) which are heavily infested by the cotton aphid (*Aphis gossypii*) are sprayed to runoff point with the preparation of active compound at the desired concentration.

After the desired period of time, the kill in % is determined. 100% means that all aphids have been killed; 0% means that none of the aphids have been killed.

TABLE

| Active compound | Concentration (ppm) | Kill (%) after 6 d | +AS 1000 ppm | +RME 1000 pm | +AS + RME 1000 ppm each |
|---|---|---|---|---|---|
| I-1-a-1 | 20 | 0 | 5 | 15 | 80 |
| | 4 | 0 | 0 | 0 | 60 |

Example 15

Herbicidal Post-Emergence Action

Seeds of monocotyledonous and dicotyledonous weed and crop plants are placed in sandy loam in wood fibre pots and covered with soil. The test compounds, formulated in the form of wettable powders (WP), are then, as an aqueous suspension with a water application rate of 600 l/ha (converted), with 0.2% of wetting agent added, applied to the surface of the covering soil.

After the treatment, the pots are placed in a greenhouse and kept under good growth conditions for the test plants. The visual assessment of the emergence damage on the test plants is carried out after a trial period of 3 weeks by comparison with the untreated controls (herbicidal effect in percent: 100% effect=the plants have died, 0% effect=like control plants).

In addition to the compounds mentioned above, the following compounds, applied by the pre-emergence method at 320 g of a.i./ha, show an efficacy of ≥80% against *Echinocloa*

*crus-galli* and *Setaria viridis*: I-1-a-3, I-1-a-7, I-1-a-46, I-1-a-47, I-1-a-50, I-1-a-51, I-1-a-53, I-1-a-55

Herbicidal Post-Emergence Action

Seeds of monocotyledonous and dicotyledonous weed and crop plants are placed in sandy loam in wood fibre pots, covered with soil and cultivated in the greenhouse under good growth conditions. 2-3 weeks after sowing, the test plants are treated at the one-leaf stage. The test compounds, formulated as wettable powders (WP), are then, at various dosages with a water application rate of 600 l/ha (converted), with 0.2% of wetting agent added, sprayed onto the green parts of the plants. After the test plants have been kept in the greenhouse under optimum growth conditions for about 3 weeks, the effect of the preparations is rated visually in comparison to untreated controls (herbicidal effect in percent: 100% effect=the plants have died, 0% effect=like control plants).

In addition to the compounds mentioned above, the following compounds, applied by the post-emergence method at 80 g/ha, show an efficacy of ≥80% against *Echinocloa crus-galli* and *Setaria viridis*: I-1-a-7, I-1-a-11, I-1-a-16, I-1-a-17, I-1-a-18, I-1-a-50, I-1-a-51, I-1-a-54.

The invention claimed is:

1. A compound of formula (I)

(I)

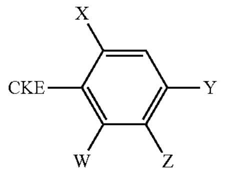

in which

W represents hydrogen or methyl,

X represents fluorine, chlorine, methyl, ethyl, propyl, isopropyl, methoxy, ethoxy, propoxy, isopropoxy, trifluoromethyl, difluoromethoxy or trifluoromethoxy, Y represents hydrogen, methyl, fluorine or chlorine, Z represents the radical

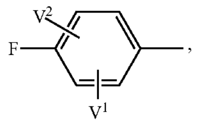

$V^1$ represents hydrogen, fluorine, chlorine, methyl, ethyl, methoxy, ethoxy, trifluoromethyl or trifluoromethoxy, $V^2$ represents hydrogen, fluorine, chlorine, methyl or methoxy, CKE represents one of the groups (1)

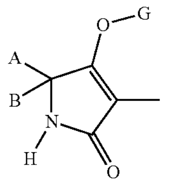

or (2)

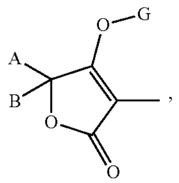

A, B and the carbon atom to which they are attached represent saturated $C_6$-cycloalkyl in which one ring member is replaced by oxygen at 3 or 4 position, G represents hydrogen (a) or represents one of the groups (b)

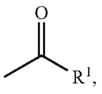

(c)

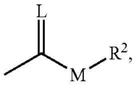

or (f)

E, in which

L represents oxygen or sulphur,

M represents oxygen or sulphur and

E represents a metal ion equivalent or an ammonium ion, $R^1$ represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally monosubstituted by fluorine or chlorine, or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine.

2. A process for preparing compounds of formula (I) according to claim 1, characterized in that, (A) in order to obtain a compound of formula (I-1-a)

(I-1-a)

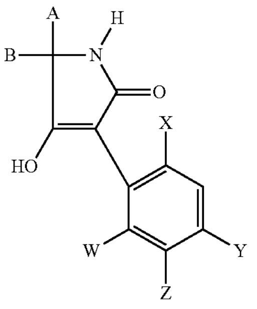

in which

A, B, W, X, Y and Z are as defined in claim 1, an N-acylamino acid ester of formula (II)

(II)

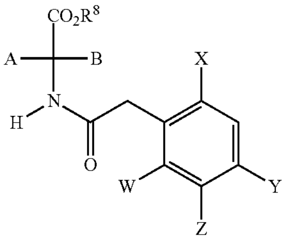

in which

A, B, W, X, Y and Z are as defined in claim 1, and $R^8$ represents alkyl is condensed intramolecularly in the presence of a diluent and in the presence of a base;

(B) in order to obtain a compound of formula (I-2-a)

(I-2-a)

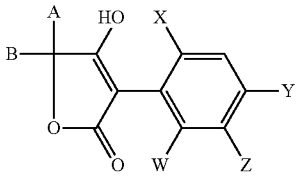

in which

A, B, W, X, Y and Z are as defined in claim 1, a carboxylic ester of the formula (III)

(III)

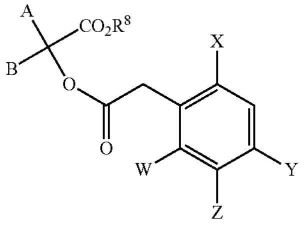

in which

A, B, W, X, Y and Z are as defined in claim 4 and $R^8$ is alkyl, is condensed intramolecularly in the presence of a diluent and in the presence of a base;

(C) in order to obtain a compound of formula (I-1-a), (I-1-b), (I-1-c), (I-1-f), (I-2-a), (I-2-b), (I-2-c), or (I-2-f) shown below, (I-1-a):

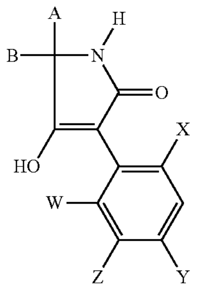

(I-1-b):

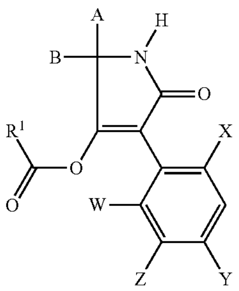

-continued (I-1-c):

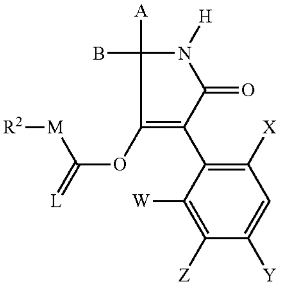

(I-1-f):

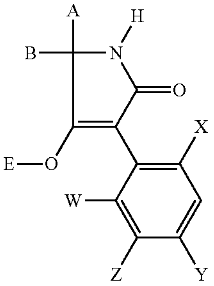

(I-2-a):

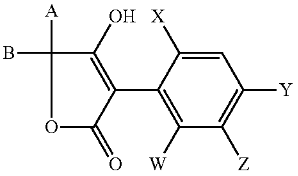

(I-2-b):

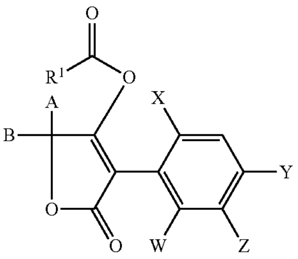

(I-2-c):

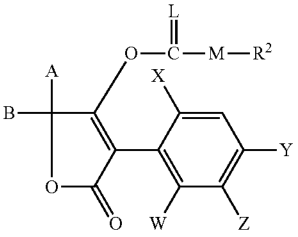

(I-2-f):

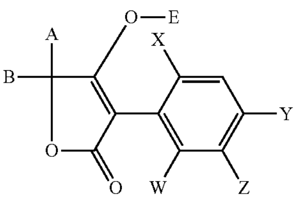

in which

A, B, E, L, M, W, X, Y, Z, $R^1$, and $R^2$, are as defined in claim 1, a corresponding compound of formula (I-1'-a), (I-1'-b), (I-1'-c), (I-1'-f), (I-2'-a), (I-2'-b), (I-2'-c), or (I-2'-f), respectively

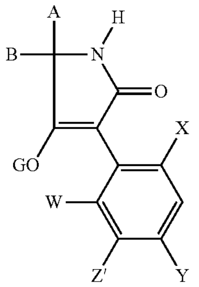

(I-1′-a) (I-1′-b), or (I-1′-c), (I-1′-f)

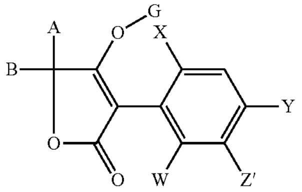

(I-2′-a) (I-2′-b), (I-2′-c), or (I-2′-f)

in which

A, B, G, W, X and Y are as defined in claim 1, and

Z' represents chlorine, bromine, or iodine, is reacted with a boronic acid or a boronic acid derivative of the formula (IV)

(IV)

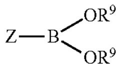

in which $R^9$ represents hydrogen, $C_1$-$C_6$-alkyl or $C_2$-$C_6$-alkanediyl and Z is as defined in claim 1, in the presence of a solvent, a base and a catalyst, wherein the catalyst is a palladium salt or a palladium complex;

(D) in order to obtain a compound of formula (I-1-b) or formula (I-2-b) in which A, B, $R^1$, W, X, Y and Z are as defined in claim 1, a compound of the formula (I-1-a) or (I-2-a) in which A, B, W, X, Y and Z are as defined in claim 1, is in each case reacted (α) with an acid halide of formula (V)

(V)

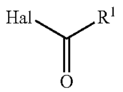

in which $R^1$ is as defined in claim 1, and

Hal represents halogen, or (β) with a carboxylic anhydride of the formula (VI)

$R^1$—CO—O—CO—$R^1$ (VI)

in which $R^1$ is as defined in claim 1, optionally in the presence of a diluent and optionally in the presence of an acid binder;

(E) in order to obtain a compound of formula (I-1-c) or (I-2-c) in which A, B, $R^2$, M, W, X, Y and Z are as defined in claim 1, and L represents oxygen, a compound of the formula (I-1-a) or (I-2-a) in which A, B, W, X, Y and Z are as defined in claim 1, is in each case reacted with a chloroformic ester or a chloroformic thioester of formula (VII)

$R^2$-M-CO—Cl (VII)

in which $R^2$ and M are as defined in claim 1, optionally in the presence of a diluent and optionally in the presence of an acid binder;

(F) in order to obtain a compound of formula (I-1-c) or (I-2-c) in which A, B, $R^2$, M, W, X, Y and Z are as defined in claim 1 and L represents sulphur, a compound of formula (I-1-a) or (I-2-a) in which A, B, W, X, Y and Z are as defined in claim 1, is in each case reacted with a chloromonothioformic ester or a chlorodithioformic ester of formula (VIII)

(VIII)

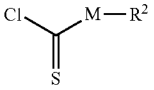

in which

M and $R^2$ are as defined in claim 1, optionally in the presence of a diluent and optionally in the presence of an acid binder; and (G) in order to obtain a compound of formula (I-1-f) or (I-2-f) in which A, B, E, W, X, Y and Z are as defined in claim 1, a compound of formula (I-1-a) or (I-2-a) in which A, B, W, X, Y and Z are as defined in claim 1, is in each case reacted with a metal compound or an amine of formulae (XI) and (XII), respectively, (XI)

$Me(OR^{10})_t$ (XII)

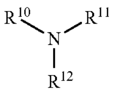

in which

Me represents a mono- or divalent metal, t represents the number 1 or 2 and $R^{10}$, $R^{11}$, $R^{12}$ independently of one another represent hydrogen or alkyl, optionally in the presence of a diluent.

3. A pesticide, herbicide, or a combination thereof, comprising at least one compound of the formula (I) according to claim 1, and an extender, surfactant or combination thereof.

4. A method for controlling animal pests, unwanted vegetation, or combinations thereof, comprising allowing a compound of formula (I) according to claim 1 to act on pests, their habitat, or combinations thereof.

5. A process for preparing pesticides, herbicides, or combinations thereof, comprising mixing a compound of formula (I) according to claim 1 with an extender, a surfactant, or combinations thereof.

6. A compound of formula (I-1-a)

(I-1-a)

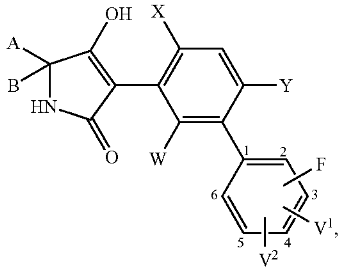

in which

| Compound | W | X | Y | F | $V^1$ | $V^2$ | A | B |
|---|---|---|---|---|---|---|---|---|
| I-1-a-4 | $CH_3$ | $CH_3$ | H | 4 | H | H | $—(CH_2)_2—O—(CH_2)_2—$ | |
| I-1-a-5 | $CH_3$ | $CH_3$ | H | 4 | 3-F | H | $—(CH_2)_2—O—(CH_2)_2—$. | |

7. A compound of formula (I-1-f)

(I-1-f)

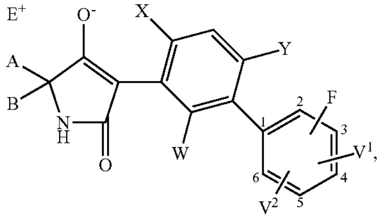

in which

| Compound | W | X | Y | F | $V^1$ | $V^2$ | A | B | E |
|---|---|---|---|---|---|---|---|---|---|
| I-1-f-1 | $CH_3$ | $CH_3$ | H | 4 | H | H | $—(CH_2)_2—O—(CH_2)_2—$ | | $Na^+$ |
| I-1-f-2 | $CH_3$ | $CH_3$ | H | 4 | H | H | $—(CH_2)_2—O—(CH_2)_2—$ | | $K^+$. |

* * * * *